(12) United States Patent
Rohlff et al.

(10) Patent No.: US 10,982,005 B2
(45) Date of Patent: Apr. 20, 2021

(54) ANTIBODIES TO BONE MARROW STROMAL ANTIGEN 1

(71) Applicant: Oxford BioTherapeutics Ltd, Abingdon (GB)

(72) Inventors: Christian Rohlff, Abingdon (GB); Jonathan Alexander Terrett, Sunnyvale, CA (US)

(73) Assignee: Oxford BioTherapeutics Ltd, Abingdon (GB)

(*) Notice: Subject to any disclaimer, the term of this patent is extended or adjusted under 35 U.S.C. 154(b) by 0 days.

(21) Appl. No.: 16/286,363

(22) Filed: Feb. 26, 2019

(65) Prior Publication Data

US 2019/0322764 A1    Oct. 24, 2019

Related U.S. Application Data

(60) Division of application No. 15/645,041, filed on Jul. 10, 2017, now Pat. No. 10,239,956, which is a division of application No. 14/862,850, filed on Sep. 23, 2015, now Pat. No. 9,732,160, which is a division of application No. 13/840,828, filed on Mar. 15, 2013, now Pat. No. 9,175,092, which is a continuation-in-part of application No. PCT/US2012/044703, filed on Jun. 28, 2012.

(60) Provisional application No. 61/502,167, filed on Jun. 28, 2011.

(51) Int. Cl.
| A61K 47/68 | (2017.01) |
| C07K 16/40 | (2006.01) |
| C07K 16/28 | (2006.01) |
| A61K 39/00 | (2006.01) |

(52) U.S. Cl.
CPC .......... *C07K 16/40* (2013.01); *A61K 47/6871* (2017.08); *C07K 16/2896* (2013.01); *A61K 2039/505* (2013.01); *C07K 2317/24* (2013.01); *C07K 2317/30* (2013.01); *C07K 2317/55* (2013.01); *C07K 2317/565* (2013.01); *C07K 2317/732* (2013.01); *C07K 2317/77* (2013.01)

(58) Field of Classification Search
CPC ................................................ A61K 47/6861
See application file for complete search history.

(56) References Cited

U.S. PATENT DOCUMENTS

| 6,414,113 | B1 | 7/2002 | Sato et al. |
| 8,017,121 | B2 | 9/2011 | Kishimoto et al. |
| 9,175,092 | B2 | 11/2015 | Rohlff et al. |
| 9,447,178 | B2 | 9/2016 | Rohlff et al. |
| 9,732,160 | B2 | 8/2017 | Rohlff et al. |
| 10,239,956 | B2 | 3/2019 | Rohlff et al. |
| 2009/0232822 | A1 | 9/2009 | Joseloff et al. |
| 2013/0273068 | A1 | 10/2013 | Rohlff et al. |
| 2014/0193333 | A1 | 7/2014 | Rohlff et al. |
| 2016/0002354 | A1 | 1/2016 | Rohlff et al. |

FOREIGN PATENT DOCUMENTS

| JP | 2005-295921 | 10/2005 |
| WO | 2011/027310 A1 | 3/2011 |

OTHER PUBLICATIONS

Harlow et al., Antibodies, A Laboratory Manual, Cold Spring Harbor Laboratory, 1988, p. 76).*
Rudikoff et al. Proc. Natl. Acad. Sci. USA vol. 79, pp. 1979-1983 (Mar. 1982).*
Janeway et al. Immunology, 3rd ed., 1997, Garland Publications, Inc., pp. 3:1-3:11.*
Vajdos et al. Comprehensive Functional Maps of the Antigen-binding Site of an Anti-ErbB2 Antibody Obtained with Shotgun Scanning Mutagenesis. Journal of Molecular Biology. Jul. 5, 2002; 320(2):415-28.*
Brown et al. Tolerance of single, but not multiple, amino acid replacements in antibody VH CDR 2: a means of minimizing B cell wastage from somatic hypermutation. Journal of Immunology. May 1996;156(9):3285-91.*
Balmana, J. et al., "BRCA in Breast Cancer: ESMO Clinical Recommendations," Annals of Oncology, vol. 20 (Supplement 4):iv19-20 (2009).
Beers & Berkow, The Merck Manual, 17th edition, pp. 986-995 (1999).
Brown et al. "Tolerance of single, but not multiple, amino acid replacements in antibody VH CDR 2: a means of minimizing B cell wastage from somatic hypermutation. Journal of Immunology," vol. 156(9):3285-3291 (1996).
Bruono, Nicola Lo et al., "The CD157-Integrin Partnership Controls Transendothelial Migration and Adhesion of Human Monocytes," The Journal of Biological Chemistry, vol. 286(21):18681-18691 (2011).
Carter, P.J. "Potent Antibody Therapeutics by Design," The Journal of Immunology, Nature Pub. Group, GB. vol. 6, Apr. 7, 2006, pp. 343-357, XP007901440, ISSN:; 1474-1733.;.
Cedarlane Laboratories Limited, "Purified Anti-Mouse CD157 Receptor Monoclonal Antibody," retrieved online at www.cedarlanelabs.com, 3 pages (2008).

(Continued)

*Primary Examiner* — Prema M Mertz
(74) *Attorney, Agent, or Firm* — Nelson Mullins Riley & Scarborough LLP; Jane E. Remillard, Esq.; Jill Gorny Sloper, Esq.

(57) ABSTRACT

The invention provides antibodies which bind to the ADP-ribosyl cyclase 2. Nucleic acid molecules encoding the antibodies, expression vectors, host cells and methods for expressing the antibodies are also provided. The antibodies may be used for the treatment of human cancers, including acute myeloid leukemia (AML), B-cell chronic lymphocytic leukemia, breast cancer, colorectal cancer, kidney cancer, head and neck cancer, lung cancer, ovarian cancer and pancreatic cancer and human inflammatory diseases, including asthma, gout, crohns, lupus, multiple sclerosis, rheumatoid arthritis, psoriasis, diabetes and atherosclerotic.

11 Claims, 10 Drawing Sheets

Specification includes a Sequence Listing.

(56) References Cited

OTHER PUBLICATIONS

Dermer, G., "Another Anniversary for the War on Cancer," Bio/Technology, vol. 12:213-320 (1994).
Freshney. R., "Culture of Animal Cells, A Manual of Basic Technique," Alan R. Liss, Inc., New York, p. 4 (1983).
Funaro, Ada et al., "CD157 is an important mediator of neutrophil adhesion and migration," Blood, vol. 104 (13):4269-4278 (2004).
Gura, T. "Systems for Identifying New Drugs Are Often Faulty," Science, vol. 278:1041-1042 (1997).
Harris, P. et al, "Distinct activities of interferon-gamma, lymphokine and cytokine differentiation-inducing factors acting on the human monoblastic leukemia cell line U937," Cancer Research, vol. 45, pp. 9-13 (1985).
Harris, P., "Human leukemic models of myelomonocytic development: a review of the HL-60 and U937 cell lines," Journal of Leukocyte Biology, vol. 37, pp. 407-422 (1985).
Hu, S. et al., "Activity of the multikinase inhibitor sorafenib in combination with cytarabine in acute myeloid leukemia," JNCI, vol. 103(11), pp. 893-905 (2011).
Hu, S. et al., "Comparison of antitumor effects of multitargeted tyrosine kinase inhibitors in acute myelogenous leukemia," Mol Cancer Therapy, vol. 7(5), pp. 1110-11120 (2008).
International Preliminary Report on Patentability and Written Opinion for Application No. PCT/IB2012/001680, 8 pages, dated Jan. 7, 2014.
International Preliminary Report on Patentability and Written Opinion for Application No. PCT/US2012/044703, 12 pages, dated Jan. 7, 2014.
International Search Report and Written Opinion for Application No. PCT/US2012/044703, 20 pages, dated May 24, 2013.
International Search Report for Application No. PCT/IB2012/001680, 4 pages, dated Mar. 13, 2013.
Ishihara, Katsuhiko et al., "BST-1/CD157 Regulates the Humoral Immune Responses in vivo," Chem. Immunol., vol. 75:235-255 (2000).
Jain, R., "Barriers to Drug Delivery in Solids Tumors," Sci. Am., vol. 271:58-65 (1994).
Kaisho, Tsuneyasu et al., "BST-1, a surface molecule of bone marrow stromal cell lines that facilitates pre-B-cell growth," Proc. Natl. Acad. Sci. USA, vol. 91:5325-5329 (1994).
Kataja et al., "Primary Breast Cancer: ESMO Clinical Recommendations for diagnoses, treatment and follow-up," Annals of Oncology, vol. 20 (Supplement 4):iv10-14 (2009).
Kohls, MD et al., "Mab-ZAP: a tool for evaluating antibody efficacy for use in an immunotoxin," Biotechnique, vol. 28 (1) pp. 162-165 (2000).
Koyama, T. et al, "All-trans retinoic acid upregulates thrombomodulin and downregulates tissue-factor expression in acute promyelocytic leukemia cells: distinct expression of thrombomodulin and tissue factor in human leukemic cells," Blood, vol. 84(9), pp. 001-3009 (1994).
Krzykowska-Petitjean, K. et al., "Tipifarnib and tanespimycin show synergic proapoptotic activity in U937 cells," J Cancer Res Clin Oncol, vol. 138, pp. 537-544 (2012).

Lee et al., "Elevated levels of the soluble form of bone marrow stromal cell antigen 1 in the sera of patients with severe rheumatoid arthritis," Arthritis & Rheumatism, vol. 39(4):629-637 (1996).
Liu, Sue M. et al., "Immune cell transcriptome datasets reveal novel leukocyte subset-specific genes and genes associated with allergic processes," J. Allergy Clin. Immunol., vol. 118:496-503 (2006).
Malavasi, Fabio et al., "Evolution and Function of the ADP Ribosyl Cyclase/CD38 Gene Family in Physiology and Pathology," Physiol. Rev., vol. 88:841-886 (2008).
McNagny, Kelly M. et al., "A Cell Surface Glycoprotein that Marks Early B Lineage Cells and Mature Myeloid Lineage Cells in Mice," The Journal of Immunology, vol. 141(8):2551-2556 (1988).
Nelson et al., Screening for Breast Cancer: An update for the U.S. Preventive Services Task Force,: Ann. Intern Med., vol. 151:727-737 (2009).
Nimmerjahn, F. et al., "Antibodies, Fc receptors and cancer", Current Opinion in Immunology, Elsevier, OX, GB, vol. 19, No. 2, Mar. 8, 2007, pp. 239-245, XP005917726, ISSN: 0952-7915.
Okuyama, Yoshiki et al., "Human BST-1 Expressed on Myeloid Cells Functions as a Receptor Molecule," Biochemical and Biophysical Research Communications, vol. 228:838-845 (1996).
Ortolan, Erika et al., "Functional Role and Prognostic Significance of CD157 in Ovarian Carcinoma," J. Natl. Cancer Inst., vol. 102(15):1160-1177 (2010).
Rudikoff et al., "Single amino acid substitution altering antigen-binding specificity," Proceeding of the National Academy of Sciences, vol. 79(6): 1979-1983 (1982).
Saito, T. et al., "Anticoagulant effects of retinoic acids on leukemia cells," Blood, vol. 87(2), pp. 657-665 (1996).
Sato, A. et al., "Novel Peptide Inhibitor of ecto-ADP-ribosyl cyclase of bone marrow stromal cell antigen-1 (BST-1/CD157)," Biochem. J., vol. 337, 1999, pp. 491-496.
Seki, Mizue et al., "An Immature Rat Lymphocyte Marker CD157: Striking Differences in the Expression between Mice and Rats," Immunbiol., vol. 203:725-742 (2001).
Sposato et al. Tissue Antigens, 7th Workshop and Conference on Human Leucocyte Differentiation Antigens, vol. 55 (Supplement 1): 71, Poster Presentation No. L. 10,2000.
Sposato, P. et al., "Analysis of human CD157 by murine monoclonal antibodies (MoAbs)," Tissue Antigens, 7th Workshop and Conference on Human Leucocyte Differentiation Antigens, vol. 55(Suppl. 1):71, Poster Presentation No. L. 10 (2000).
Todd, Robert F., III et al., "The Modulated Expression of Mo5, a Human Myelomonocytic Plasma Membrane Antigen," Blood, vol. 65(4):964-973 (1985).
Vajdos et al., "Comprehensive Functional Maps of the Antigen-binding Site of an Anti-ErbB2 Antibody Obtained with Shotgun Scanning Mutagenesis," Journal ofMolecular Biology, vol. 320(2): 415-428 (2002).
Winkler K., et al., "Changing the antigen binding specificity by single point mutations of an anti-p24 (HIV-1) antibody", The Journal of Immunology, The American Association of Immunologists, US, vol. 165, No. 8, Oct. 15, 2000, pp. 4505-4514, XP002579393, ISSN: 0022-1767.

* cited by examiner

VH CDR1 Alignments

A1
SEQ ID No: 21        ggctacgcattcagtaactcctggataaactgg
SEQ ID No: 33        ggctacgcattcagtagctactggatgaactgg
                     ************  **** ****

A2
SEQ ID No: 22        ggttactcattcattgagtacaccataaactgg
SEQ ID No: 35        ggttactcattcactgactacaacatgaactgg
                     ********** * ** * ******

A3
SEQ ID No: 62        ggctacacattctctgactactgggtacactgg
SEQ ID No: 68        ggctacaccttcaccagctactggatgcactgg
                     ****** * *   ****** * ******

FIG. 1A

VH CDR2 Alignments

A1
SEQ ID No: 23        ggacagatttatcctggagattatgatactaactacaatggaaaattcaag
SEQ ID No: 34        ggacagatttatcctggagatggtgatactaactacaacggaaagttcaag
                     ******************  ********** * ****

A2
SEQ ID No: 24        ggaaatattgatccttattatggaaccacttattacaatcagatgttcacg
SEQ ID No: 36        ggagtaattaatcctaactatggtactactagctacaatcagaagttcaag
                     *   * ***** * ***  *     ****** ***

A3
SEQ ID No: 63        ggagcgattgatggttctgatacttttaatgactacagtcagaagtttaag
SEQ ID No: 69        ggagagattgatccttctgatagttatactaactacaatcaaaagttcaag
                     ** ***  ****    * * **** * *** *

FIG. 1B

VK CDR1 Alignments

A1
SEQ ID No: 27    actgccagctcacgtgtaagttccagttacttgcac
SEQ ID No: 37    actgccagctcaagtgtaagttccagttacttgcac
                 ******** ***********************

A2
SEQ ID No: 28    agtgccagctcaagtgtaacttacatgtac
SEQ ID No: 40    agtgccagctcaagtgtaagttacatgtac
                 ***************** *******

A3
SEQ ID No: 65    cgagcaagtgaaaacatttacagttatttagca
SEQ ID No: 70    cgagcaagtgagaatatttacagttatttagca
                 ********  *******************

FIG. 2A

VK CDR2 Alignments

A1
SEQ ID No: 29    agtacatccaacctggcttct
SEQ ID No: 38    agcacatccaacctggcttct
                  ****************

A2
SEQ ID No: 30    gacacatccaacctggcttct
SEQ ID No: 41    gacacatccaacctggcttct
                 *********************

A3
SEQ ID No: 66    aatacaaaaaccttaggagaa
SEQ ID No: 71    aatgcaaaaaccttagcagaa
                 * ******** **

FIG. 2B

VK CDR3 Alignments

A1
SEQ ID No: 31    caccagtatcatcgttccccgtacacg
SEQ ID No: 39    caccagtatcatcgttccccaccca--
                 ******************

A2
SEQ ID No: 32    cagcagtggagtaattacccactcacg
SEQ ID No: 42    cagcagtggagtagttacccaccca--
                 *********** ***

A3
SEQ ID No: 67    caacatcattatggtactccattcacg
SEQ ID No: 72    caacatcattatggtactcctcc----
                 *******************

FIG. 2C

```
                       1          2          3          4
              123456789 0123456789 0123456789 0123456789 0123456789
SEQ ID No: 45 QAYLQQSGP  ELVKAGASVK MSCKASGYSF IEYTINWVKQ SHGKSLEWIG
SEQ ID No: 46 QVQLVQSGA  EVKKPGASVK VSCKASGYSF IEYTINWVRQ APGQGLEWIG
SEQ ID No: 47 QVQLVQSGA  EVKKPGASVK VSCKASGYSF TXXXXXWVRQ APGQGLEWMG 5          6          7          8
              0122345678 0123456789 0123456789 0122223456789
SEQ ID No: 45 NIDPYYGTTYY NQMFTGKATL TVDQSSNTAY MQLKSLTSEDSAV
SEQ ID No: 46 NIDPYYGTTYY NQMFTGRATL TVDTSISTAY MELSRLRSDDTAV
SEQ ID No: 47 XXXXXXXXXXX XXXXXXRVTL TRDTSISTAY MELSRLRSDDTAV 1          1
              9          0          1
              0123456789 0123456789 0123
SEQ ID No: 45 YFCARGSAWF -PYWGQGTLV TVSA
SEQ ID No: 46 YYCARGSAWF -PYWGQGTLV TVSS
SEQ ID No: 47 YYCARXXXXX XXXWGQGTLV PVSS
```

FIG. 5

```
                       1          2          3
              123456789 0123456789 0123456789 0123456789
SEQ ID No: 48 DIVMSQSPA  IMSASPGEKV TMTCSAS-SS VTYMYWYQQK
SEQ ID No: 49 DIQMTQSPS  SLSASVGDRV TITCSAS-SS VTYMYWYQQK
SEQ ID No: 50 DIQMTQSPS  SLSASVGDRV TITCXXXXXX XXXXXWYQQK 4          5          6          7
              0123456789 0123456789 0123456789 0123456789
SEQ ID No: 48 PGSSPRLLIY DTSNLASGVP VRFSGSGSGT SYSLTISRME
SEQ ID No: 49 PGKAPKLLIY DTSNLASGVP SRFSGSGSGT DYTLTISSLQ
SEQ ID No: 50 PGKAPKLLIY XXXXXXXGVP SRFSGSGSGT DFTLTISSLQ 1
              8          9          0
              0123456789 0123456789 01234567
SEQ ID No: 48 AEDTATYYCQ QWSNYPLTFG AGTKLELK
SEQ ID No: 49 PEDFATYYCQ QWSNYPLTFG QGTKVEIK
SEQ ID No: 50 PEDFATYYCX XXXXXXXFG  QGTKVEIK
```

FIG. 6

```
SEQ ID No: 12  GNIDPYYGTTYYNQMFT
SEQ ID No: 51  GNIDPYYGTTYYNQMFQ
```

FIG. 7

ANTIBODIES TO BONE MARROW STROMAL ANTIGEN 1

RELATED APPLICATIONS

This application is a divisional of U.S. patent application Ser. No. 15/645,041, filed on Jul. 10, 2017, which is a divisional of U.S. patent application Ser. No. 14/862,850, filed on Sep. 23, 2015, now U.S. Pat. No. 9,732,160, which is a divisional of U.S. patent application Ser. No. 13/840,828, filed on Mar. 15, 2013, now U.S. Pat. No. 9,175,092, which is a continuation-in-part of International Application No. PCT/US2012/044703, filed on Jun. 28, 2012, which claims priority to U.S. Provisional Application No. 61/502,167, filed on Jun. 28, 2011. The contents of the aforementioned applications are hereby incorporated by reference.

INTRODUCTION

The present disclosure relates generally to the fields of immunology and molecular biology. More specifically, provided herein are antibodies and other therapeutic proteins directed against the ADP-ribosyl cyclase 2, nucleic acids encoding such antibodies and therapeutic proteins, methods for preparing monoclonal antibodies and other therapeutic proteins, and methods for the treatment of diseases, such as cancers mediated by the ADP-ribosyl cyclase 2 expression/activity and/or associated with abnormal expression/activity of ligands therefore.

BACKGROUND OF THE INVENTION

ADP-ribosyl cyclase 2 (also known as Bone marrow stromal antigen 1 (BST1) or CD157) is a lipid-anchored, bi-functional ectoenzyme that catalyses ribonucleotide cyclisation and hydrolysis. It generates the nucleotide second messengers cyclic ADP-ribose and ADP-ribose that are capable of activating calcium release and protein phosphorylation (FEBS Lett. 1994, 356(2-3):244-8). It is able to support growth of pre-B cells in a paracrine fashion, possibly through generation of NAD+ metabolites (Proc. Natl. Acad. Sci. USA 1994, 91:5325-5329; J Biol Chem. 2005, 280:5343-5349).

ADP-ribosyl cyclase 2 and its homolog, CD38, appear to act as receptors, generating second messenger metabolites that induce intracellular Ca2+ release via the ryanodine receptor (Biochem Biophys Res Commun. 1996, 228(3): 838-45). It may also act via CD11b integrin to effect Ca2+ release through the PI-3 Kinase pathway (J Biol Regul Homeost Agents. 2007; 21(1-2):5-11). BST1 has not been previously reported to originate from acute myeloid leukemia (AML), breast cancer, colorectal cancer, kidney cancer, lung cancer or pancreatic cancer cell membranes and represents a protein of new therapeutic and diagnostic value. BST1 is also shown to be expressed on monocytes and granulocytes, both of which can be associated with and activated in diseases such as asthma, gout, crohns, lupus and diabetes. Monocytes are also implicated in the development of atherosclerotic plaques.

SUMMARY OF THE INVENTION

The present disclosure provides antibodies directed against the BST1, nucleic acids encoding such antibodies and therapeutic proteins, methods for preparing anti-BST1 antibodies and other therapeutic proteins, and methods for the treatment of diseases, such as the BST1 mediated disorders, e.g. human cancers, including acute myeloid leukemia (AML), B-cell chronic lymphocytic leukemia, breast cancer, colorectal cancer, kidney cancer, head and neck cancer, lung cancer, ovarian cancer, pancreatic cancer and human inflammatory diseases, including asthma, gout, crohns, lupus, multiple sclerosis, rheumatoid arthritis, psoriasis, diabetes and atherosclerotic, hereinafter referred to as 'the diseases of the invention'.

Thus, the present disclosure provides isolated antibodies, in particular murine, chimeric, humanized and fully-human monoclonal antibodies that bind to the BST1 and exhibit one or more desirable functional property. Such properties include, for example, high affinity specific binding to the BST1. Also provided are methods for treating a variety of the BST1-mediated diseases using the antibodies, proteins and compositions of the present invention.

In one embodiment, the isolated anti-BST1 antibody possesses:
a) a heavy chain variable region comprising:
  i) a first CDR comprising a sequence at least 80% identical to SEQ ID NO: 10;
  ii) a second CDR comprising a sequence at least 80% identical to SEQ ID NO: 12 or SEQ ID NO: 51;
  iii) a third CDR comprising a sequence at least 80% identical to SEQ ID NO: 14; and
b) a light chain variable region comprising:
  i) a first CDR comprising a sequence at least 80% identical to SEQ ID NO: 16;
  ii) a second CDR comprising a sequence at least 80% identical to SEQ ID NO: 18;
  iii) a third CDR comprising a sequence at least 80% identical to SEQ ID NO: 20.

In a further embodiment, the isolated anti-BST1 antibody possesses:
a) a heavy chain variable region comprising:
  i) a first CDR comprising a sequence at least 80% identical to SEQ ID NO: 9;
  ii) a second CDR comprising a sequence at least 80% identical to SEQ ID NO: 11;
  iii) a third CDR comprising a sequence at least 80% identical to SEQ ID NO: 13; and
b) a light chain variable region comprising:
  i) a first CDR comprising a sequence at least 80% identical to SEQ ID NO: 15;
  ii) a second CDR comprising a sequence at least 80% identical to SEQ ID NO: 17;
  iii) a third CDR comprising a sequence at least 80% identical to SEQ ID NO: 19.

In a further embodiment, the isolated anti-BST1 antibody possesses:
a) a heavy chain variable region comprising:
  i) a first CDR comprising a sequence at least 80% identical to SEQ ID NO: 56;
  ii) a second CDR comprising a sequence at least 80% identical to SEQ ID NO: 57;
  iii) a third CDR comprising a sequence at least 80% identical to SEQ ID NO: 58; and
b) a light chain variable region comprising:
  i) a first CDR comprising a sequence at least 80% identical to SEQ ID NO: 59;
  ii) a second CDR comprising a sequence at least 80% identical to SEQ ID NO: 60;
  iii) a third CDR comprising a sequence at least 80% identical to SEQ ID NO: 61.

The epitope(s) recognized by the antibodies of the invention is found within the polypeptide sequence of SEQ ID NO: 44.

In a further embodiment, the antibodies of the invention comprise variable CDRs as compared to the parent antibodies described herein. Thus, the invention provides variant antibodies comprising variant variable regions of a parent antibody, wherein the parent antibody comprises a first vhCDR comprising SEQ ID NO:10, a second vhCDR comprising a sequence selected from the group consisting of SEQ ID NO: 12 and SEQ ID NO: 51, a third vhCDR comprising SEQ ID NO:14, a first vlCDR comprising SEQ ID NO:16, a second vlCDR comprising SEQ ID NO: 18; and a third vlCDR comprising a SEQ ID NO:20, and wherein the variant antibody has 1, 2, 3, 4, 5 or 6 amino acid substitutions collectively in the set of the first vhCDR, the second vhCDR, the third vhCDR, the first vlCDR, the second vlCDR and the third vlCDR, with from 1 to 4 substitutions of particular use, and wherein the antibody retains specific binding to BST1. Similarly, the parent antibody can comprise a first vhCDR comprising SEQ ID NO:9, a second vhCDR comprising SEQ ID NO:11, a third vhCDR comprising SEQ ID NO:13; a first vlCDR comprising SEQ ID NO:15, a second vlCDR comprising SEQ ID NO: 17 and a third vlCDR comprising a SEQ ID NO:19. Furthermore, the parent antibody can comprise a first vhCDR comprising SEQ ID NO:56, a second vhCDR comprising SEQ ID NO: 57, a third vhCDR comprising SEQ ID NO:58, a first vlCDR comprising SEQ ID NO:59, a second vlCDR comprising SEQ ID NO:60 and a third vlCDR comprising a SEQ ID NO:61.

In a further embodiment, the isolated anti-BST1 antibody possesses the heavy chain variable region sequence as represented by SEQ ID NO: 2 and the light chain variable region sequence as represented by SED ID NO: 4.

In another embodiment, the isolated anti-BST1 antibody possesses the heavy chain variable region sequence as represented by SEQ ID NO: 45 and the light chain variable region sequence as represented by SED ID NO: 49.

In another embodiment, the isolated anti-BST1 antibody possesses the heavy chain variable region sequence as represented by SEQ ID NO: 1 and the light chain variable region sequence as represented by SED ID NO: 3.

In a further embodiment, the isolated anti-BST1 antibody possesses the heavy chain variable region sequence as represented by SEQ ID NO: 52 and the light chain variable region sequence as represented by SED ID NO: 53.

In one embodiment, any of the preceding antibodies possesses an Fc domain. In some embodiments the Fc domain is human. In other embodiments, the Fc domain is a variant human Fc domain.

In another embodiment, any of the preceding described antibodies are monoclonal antibodies.

In one embodiment, any of the preceding described antibodies further possesses a conjugated agent. In some embodiments the conjugated agent is a cytotoxic agent. In other embodiments the conjugated agent is a polmer. In another embodiment, the polymer is a polyethylene glycol (PEG). In another embodiment, the PEG is a PEG derivative.

In one embodiment, the isolated antibody is an antibody that competes with any of the preceding antibodies for binding to BST1.

In another embodiment, a method for preparing any of the preceding antibodies is describe, the method being obtaining a host cell that contains one or more nucleic acid molecules encoding the preceding antibodies, growing the host cell in a host cell culture, providing host cell culture conditions wherein the one or more nucleic acid molecules are expressed, and recovering the antibody from the host cell or the host cell culture.

In one embodiment, any of the described anti-BST1 antibodies is provided in a pharmaceutical composition.

In another embodiment, a method for treating or preventing a disease associated with BST1, the method being administering to a subject in need thereof any of the preceding antibodies in an effective amount.

The present invention provides an isolated monoclonal antibody, or an antigen-binding portion thereof, an antibody fragment, or an antibody mimetic which binds an epitope on the human BST1 recognized by an antibody comprising a heavy chain variable region comprising an amino acid sequence set forth in a SEQ ID NO: selected from the group consisting of 2, 1 and 52 and a light chain variable region comprising an amino acid sequence set forth in a SEQ ID NO: selected from the group consisting of 4, 3 54 and 55. In some embodiments the isolated antibody is a full-length antibody of an IgG1, IgG2, IgG3, or IgG4 isotype.

In some embodiments, the antibody of the present invention is selected from the group consisting of: a whole antibody, an antibody fragment, a humanized antibody, a single chain antibody, an immunoconjugate, a defucosylated antibody, and a bispecific antibody. The antibody fragment may be selected from the group consisting of: a UniBody, a domain antibody and a Nanobody. In some embodiments, the immunoconjugates of the invention comprise a therapeutic agent. In another aspect of the invention, the therapeutic agent is a cytotoxin or a radioactive isotope.

In some embodiments, the antibody of the present invention is selected from the group consisting of: an Affibody, a DARPin, an Anticalin, an Avimer, a Versabody and a Duocalin.

In alternative embodiments, compositions of the present invention comprise an isolated antibody or antigen-binding portion and a pharmaceutically acceptable carrier.

In other aspects, the antibody of the present invention is a composition comprising the isolated antibody or antigen-binding portion according to the invention and a pharmaceutically acceptable carrier.

In some embodiments, the invention comprises an isolated nucleic acid molecule encoding the heavy or light chain of the isolated antibody or antigen-binding portion which binds to an epitope on the human BST1. Other aspects of the invention comprise expression vectors comprising such nucleic acid molecules, and host cells comprising such expression vectors.

In some embodiments, the present invention provides a method for preparing an anti-BST1 antibody, said method comprising the steps of: obtaining a host cell that contains one or more nucleic acid molecules encoding the antibody of the invention; growing the host cell in a host cell culture; providing host cell culture conditions wherein the one or more nucleic acid molecules are expressed; and recovering the antibody from the host cell or from the host cell culture.

In other embodiments, the invention is directed to methods for treating or preventing a disease associated with target cells expressing the BST1, said method comprising the step of administering to a subject an anti-BST1 antibody, or antigen-binding portion thereof, in an amount effective to treat or prevent the disease. In some aspects, the disease treated or prevented by the antibodies or antigen-binding portion thereof of the invention, is human cancer. In some embodiments, the diseases treated or prevented by the antibodies of the present invention include the diseases of the invention.

In other embodiments, the invention is directed to methods for treating or preventing a disease associated with target cells expressing the BST1, said method comprising the step of administering to a subject an anti-BST1 antibody, or antigen-binding portion thereof, in an amount effective to treat or prevent the disease. In some aspects, the disease treated or prevented by the antibodies or antigen-binding portion thereof of the invention, is human cancer. In some embodiments, the diseases treated or prevented by the antibodies of the present invention are the diseases of the invention.

In other embodiments, the invention is directed to an anti-BST1 antibody, or antigen-binding portion thereof, for use in treating or preventing a disease associated with target cells expressing the BST1. In some aspects, the disease treated or prevented by the antibodies or antigen-binding portion thereof of the invention is human cancer. In some embodiments, the diseases treated or prevented by the antibodies of the present invention are the diseases of the invention.

In other embodiments, the invention is directed to the use of an anti-BST1 antibody, or antigen-binding portion thereof, for the manufacture of a medicament for use in treating or preventing a disease associated with target cells expressing the BST1. In some aspects, the disease treated or prevented by the medicament of the invention is human cancer. In some embodiments, the diseases treated or prevented by the medicament of the present invention are the diseases of the invention.

In other embodiments, the present invention is an isolated monoclonal antibody or an antigen binding portion thereof, an antibody fragment, or an antibody mimetic which binds an epitope on the human BST1 recognized by an antibody comprising a heavy chain variable region and a light chain variable region selected from the group consisting of the heavy chain variable region amino acid sequence set forth in SEQ ID NO: 2 and the light chain variable region amino acid sequence set forth in SEQ ID NO: 4; heavy chain variable region amino acid sequence set forth in SEQ ID NO: 1 and the light chain variable region amino acid sequence set forth in SEQ ID NO: 3; heavy chain variable region amino acid sequence set forth in SEQ ID NO: 52 and the light chain variable region amino acid sequence set forth in SEQ ID NO: 53. In further aspects, the antibody is selected from the group consisting of: a whole antibody, an antibody fragment, a humanized antibody, a single chain antibody, an immunoconjugate, a defucosylated antibody, and a bispecific antibody. In further aspects of the invention, the antibody fragment is selected from the group consisting of: a UniBody, a domain antibody, and a Nanobody. In some embodiments, the antibody mimetic is selected from the group consisting of: an Affibody, a DARPin, an Anticalin, an Avimer, a Versabody, and a Duocalin. In further embodiments, the composition comprises the isolated antibody or antigen binding portion thereof and a pharmaceutically acceptable carrier.

In some embodiments, the present invention is an isolated nucleic acid molecule encoding the heavy or light chain of the isolated antibody or antigen binding portion thereof of antibody of the invention, and in further aspects may include an expression vector comprising such nucleic acids, and host cells comprising such expression vectors.

Another embodiment of the present invention is a hybridoma expressing the antibody or antigen binding portion thereof of any one of antibodies of the invention.

Other aspects of the invention are directed to methods of making the antibodies of the invention, comprising the steps of:
  immunizing an animal with an BST1 peptide;
  recovering mRNA from the B cells of said animal;
  converting said mRNA to cDNA;
  expressing said cDNA in phages such that anti-BST1 antibodies encoded by said cDNA are presented on the surface of said phages;
  selecting phages that present anti-BST1 antibodies;
  recovering nucleic acid molecules from said selected phages that encode said anti-BST1 immunoglobulins;
  expressing said recovered nucleic acid molecules in a host cell; and
  recovering antibodies from said host cell that bind to the BST1.

In some aspects of the invention, the isolated monoclonal antibody, or an antigen binding portion thereof, binds an epitope on the BST1 polypeptide having an amino acid sequence of SEQ ID NO: 44 recognized by an antibody comprising a heavy chain variable region comprising an amino acid sequence set forth in a SEQ ID NO: selected from the group consisting of 2, 1 or 52, and a light chain variable region comprising an amino acid sequence set forth in a SEQ ID NO: selected from the group consisting of 4, 3 or 53.

Other features and advantages of the instant invention will be apparent from the following detailed description and examples which should not be construed as limiting. The contents of all references, Genbank entries, patents and published patent applications cited throughout this application are expressly incorporated herein by reference.

BRIEF DESCRIPTION OF THE FIGURES

FIG. 1A shows the alignment of the nucleotide sequences of the heavy chain CDR1 regions of A1 (SEQ ID NO:21) with nucleotides 138392-138424 of the mouse germline $V_H$ 1-80 nucleotide sequence (SEQ ID NO:33); the alignment of the nucleotide sequences of the heavy chain CDR1 regions of A2 (SEQ ID NO:22) with nucleotides 153362-153394 of the mouse germline $V_H$ 1-39 nucleotide sequence (SEQ ID NO:35).

FIG. 1B shows the alignment of the nucleotide sequences of the heavy chain CDR2 regions of A1 (SEQ ID NO:23) with nucleotides 138461-138511 of the mouse germline $V_H$ 1-80 nucleotide sequence (SEQ ID NO:34); the alignment of the nucleotide sequences of the heavy chain CDR2 regions of A2 (SEQ ID NO:24) with nucleotides 153431-153481 of the mouse germline $V_H$ 1-39 nucleotide sequence (SEQ ID NO:36).

FIG. 2A shows the alignment of the nucleotide sequences of the light chain CDR1 regions of A1 (SEQ ID NO:27) with nucleotides 496-531 of the mouse germline $V_K$ 4-74 nucleotide sequence (SEQ ID NO:37); the alignment of the nucleotide sequences of the light chain CDR1 regions of A2 (SEQ ID NO:28) with nucleotides 523-552 of the mouse germline $V_K$ 4-55 nucleotide sequence (SEQ ID NO:40).

FIG. 2B shows the alignment of the nucleotide sequences of the light chain CDR2 regions of A1 (SEQ ID NO:29) with nucleotides 577-597 of the mouse germline $V_K$ 4-74 nucleotide sequence (SEQ ID NO:38); the alignment of the nucleotide sequences of the light chain CDR2 regions of A2 (SEQ ID NO:30) with nucleotides 598-618 of the mouse germline $V_K$ 4-55 nucleotide sequence (SEQ ID NO:41).

FIG. 2C shows the alignment of the nucleotide sequences of the light chain CDR3 regions of A1 (SEQ ID NO:31) with nucleotides 691-718 of the mouse germline $V_K$ 4-74 nucleotide sequence (SEQ ID NO:39); the alignment of the nucleotide sequences of the light chain CDR3 regions of A2 (SEQ ID NO:32) with nucleotides 715-739 of the mouse germline $V_K$ 4-55 nucleotide sequence (SEQ ID NO:42).

FIG. 5 shows the alignment of residues 21-137 of SEQ ID NO: 2 (SEQ ID NO: 45), humanized VH chain with the CDR regions (highlighted in bold) of SEQ ID NO: 2 transferred to the corresponding positions of the human germline BF238102 VH (SEQ ID NO: 46), with human germline BF238102 VH (SEQ ID NO: 47). Residues showing significant contact with CDR regions substituted for the corresponding human residues. These substitutions (underlined) were performed at positions 30, 48, 67, 71 and 100.

FIG. 6 shows the alignment of residues 22-128 of SEQ ID NO: 4 (SEQ ID NO: 48), humanized VL chain with the CDR regions (highlighted in bold) of SEQ ID NO: 4 transferred to the corresponding positions of the human germline X72441 VL (SEQ ID NO: 49) with human germline X72441 VL (SEQ ID NO: 50). Residues showing significant contact with CDR regions substituted for the corresponding human residues. One substitution (underlined) was performed at position 71.

FIG. 7 shows the alignment of CDR2 region of A2 heavy chain (SEQ ID NO: 12) with possible amino acid substitutions (SEQ ID NO: 51) without losing the antigen-binding affinity.

DETAILED DESCRIPTION OF THE INVENTION

Figure 3A:
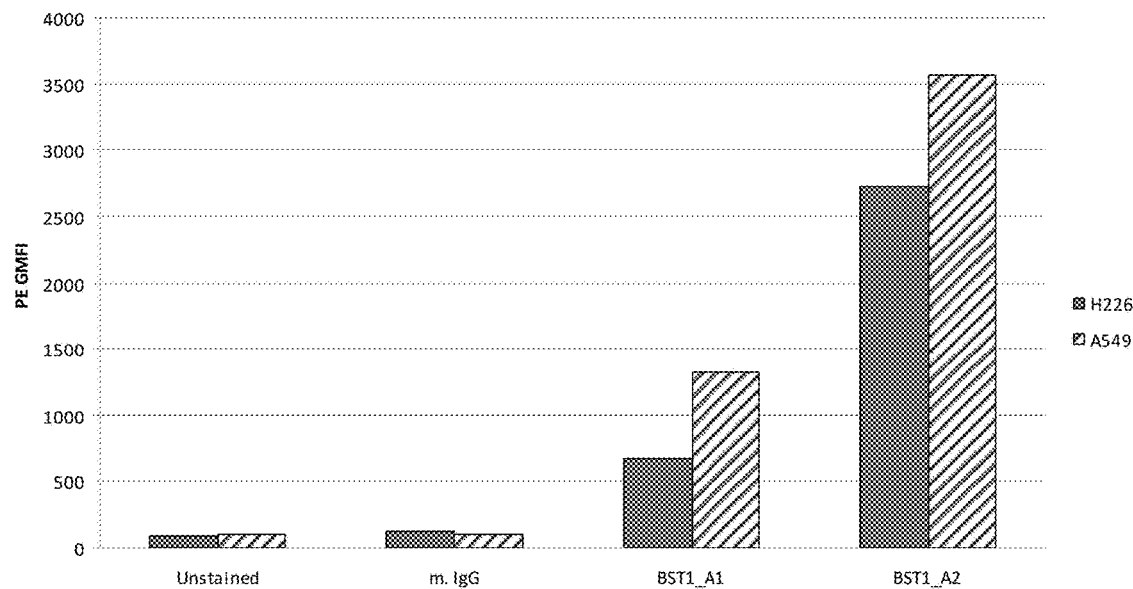
FIGS. 3A and 3B show results of flow cytometric anaysis of BST1 on A549 and H226 cells.

The present disclosure relates to isolated antibodies, including, but not limited to monoclonal antibodies, for example, which bind specifically to the BST1 with high affinity as outlined herein. In certain embodiments, the antibodies provided possess particular structural features such as CDR regions with particular amino acid sequences. This disclosure provides isolated antibodies (which, as outlined below, includes a wide variety of well known structures, derivatives, mimetics and conjugates) methods of making said molecules, and pharmaceutical compositions comprising said molecules and a pharmaceutical carrier. This disclosure also relates to methods of using the molecules, such as to detect the BST1, as well as to treat diseases associated with expression of the BST1, such as the BST1 expressed on tumors and inflammatory diseases, including the diseases of the invention.

In order that the present disclosure may be more readily understood, certain terms are first defined. Additional definitions are set forth throughout the detailed description.

Humanized and murine antibodies of this disclosure may, in certain cases, cross-react with the BST1 from species other than human. In certain embodiments, the antibodies may be completely specific for one or more human BST1 and may not exhibit species or other types of non-human cross-reactivity.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" refers to the biochemical relationship between various signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell. An example of a "cell surface receptor" is the BST1.

The term "antibody" as referred to herein includes, at a minimum, an antigen binding fragment (i.e. "antigen-binding portion") of an immunoglobulin.

The definition of "antibody" includes, but is not limited to, full length antibodies, antibody fragments, single chain antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates") and fragments and/or derivatives of each, respectively. In general, a full length antibody (sometimes referred to herein as "whole antibodies") refers to a glycoprotein which may comprise at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, $C_H1$, $C_H2$ and $C_H3$. Each light chain is comprised of a light chain variable region (abbreviated herein as $V_L$ or $V_K$) and a light chain constant region. The light chain constant region is comprised of one domain, $C_L$. The $V_H$ and $V_L/V_K$ regions can be further subdivided into regions of hypervariability, termed complementarity determining regions (CDR), interspersed with regions that are more conserved, termed framework regions (FR). Each $V_H$ and $V_L/V_K$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g. effector cells) and the first component (Clq) of the classical complement system.

In one embodiment, the antibody is an antibody fragment. Specific antibody fragments include, but are not limited to, (i) the Fab fragment consisting of $V_L$, $V_H$, CL and $C_H1$ domains, (ii) the Fd fragment consisting of the $V_H$ and $C_H1$ domains, (iii) the Fv fragment consisting of the $V_L$ and $V_H$ domains of a single antibody, (iv) the dAb fragment, which consists of a single variable domain, (v) isolated CDR regions, (vi) F(ab')2 fragments, a bivalent fragment comprising two linked Fab fragments (vii) single chain Fv molecules (scFv), wherein a $V_H$ domain and a $V_L$ domain are linked by a peptide linker which allows the two domains to associate to form an antigen binding site, (viii) bispecific single chain Fv dimers, and (ix) "diabodies" or "triabodies", multivalent or multispecific fragments constructed by gene fusion. The antibody fragments may be modified. For example, the molecules may be stabilized by the incorporation of disulfide bridges linking the $V_H$ and $V_L$ domains. Examples of antibody formats and architectures are described in Holliger & Hudson (2006) Nature Biotechnology 23(9):1126-1136, and Carter (2006) Nature Reviews Immunology 6:343-357, and references cited therein, all expressly incorporated by reference.

The present disclosure provides antibody analogs. Such analogs may comprise a variety of structures, including, but not limited to full length antibodies, antibody fragments, bispecific antibodies, minibodies, domain antibodies, synthetic antibodies (sometimes referred to herein as "antibody mimetics"), antibody fusions, antibody conjugates, and fragments of each, respectively.

In one embodiment, the immunogloublin comprises an antibody fragment. Specific antibody fragments include, but are not limited to (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment, which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site, (viii) bispecific single chain Fv dimers, and (ix) "diabodies" or "triabodies", multivalent or multispecific fragments constructed by gene fusion. The antibody fragments may be modified. For example, the molecules may be stabilized by the incorporation of disulphide bridges linking the VH and VL domains. Examples of antibody formats and architectures are described in Holliger & Hudson, 2006, Nature Biotechnology 23(9):1126-1136, and Carter 2006, Nature Reviews Immunology 6:343-357 and references cited therein, all expressly incorporated by reference.

The recognized immunoglobulin genes, for example in humans, include the kappa (κ), lambda (λ), and heavy chain genetic loci, which together comprise the myriad variable region genes, and the constant region genes mu (υ), delta (δ), gamma (γ), sigma (σ), and alpha (α) which encode the IgM, IgD, IgG (IgG1, IgG2, IgG3, and IgG4), IgE, and IgA (IgA1 and IgA2) isotypes respectively. Antibody herein is meant to include full length antibodies and antibody fragments, and may refer to a natural antibody from any organism, an engineered antibody, or an antibody generated recombinantly for experimental, therapeutic, or other purposes.

In one embodiment, an antibody disclosed herein may be a multispecific antibody, and notably a bispecific antibody, also sometimes referred to as "diabodies". These are antibodies that bind to two (or more) different antigens. Diabodies can be manufactured in a variety of ways known in the art, e.g. prepared chemically or from hybrid hybridomas. In one embodiment, the antibody is a minibody. Minibodies are minimized antibody-like proteins comprising a scFv joined to a $C_H3$ domain. In some cases, the scFv can be joined to the Fc region, and may include some or all of the hinge regions. For a description of multispecific antibodies, see Holliger and Hudson (2006) Nature Biotechnology 23(9):1126-1136 and references cited therein, all expressly incorporated by reference.

By "CDR" as used herein is meant a "complementarity determining region" of an antibody variable domain. Systematic identification of residues included in the CDRs have been developed by Kabat (Kabat et al. (1991) Sequences of Proteins of Immunological Interest, 5th Ed., United States Public Health Service, National Institutes of Health, Bethesda) and alternately by Chothia [Chothia and Lesk (1987) J. Mol. Biol. 196: 901-917; Chothia et al. (1989) Nature 342: 877-883; A1-Lazikani et al. (1997) J. Mol. Biol. 273: 927-948]. For the purposes of the present invention, CDRs are defined as a slightly smaller set of residues than the CDRs defined by Chothia. $V_L$ CDRs are herein defined to include residues at positions 27-32 (CDR1), 50-56 (CDR2), and 91-97 (CDR3), wherein the numbering is according to Chothia. Because the $V_L$ CDRs as defined by Chothia and Kabat are identical, the numbering of these $V_L$ CDR positions is also according to Kabat. $V_H$ CDRs are herein defined to include residues at positions 27-33 (CDR1), 52-56 (CDR2), and 95-102 (CDR3), wherein the numbering is according to Chothia. These $V_H$ CDR positions correspond to Kabat positions 27-35 (CDR1), 52-56 (CDR2), and 95-102 (CDR3).

As will be appreciated by those in the art, the CDRs disclosed herein may also include variants, for example, when backmutating the CDRs disclosed herein into different framework regions. Generally, the nucleic acid identity between individual variant CDRs are at least 80% to the sequences depicted herein, and more typically with preferably increasing identities of at least 85%, 90%, 91%, 92%, 93%, 94%, 95%, 96%, 97%, 98%, 99% and almost 100%. In a similar manner, "percent (%) nucleic acid sequence identity" with respect to the nucleic acid sequence of the binding proteins identified herein is defined as the percentage of nucleotide residues in a candidate sequence that are identical with the nucleotide residues in the coding sequence of the antigen binding protein. A specific method utilizes the BLASTN module of WU-BLAST-2 set to the default parameters, with overlap span and overlap fraction set to 1 and 0.125, respectively and no filters selected.

Generally, the nucleic acid sequence identity between the nucleotide sequences encoding individual variant CDRs and the nucleotide sequences depicted herein are at least 80%, and more typically with preferably increasing identities of at least 80%, 81%, 82%, 83%, 84%, 85%, 86%, 87%, 88%, 89%, 90%, 91%, 92%, 93%, 94%, 95%, 96%, 97%, 98%, or 99% and almost 100%.

Thus, a "variant CDR" is one with the specified homology, similarity, or identity to the parent CDR of the invention, and shares biological function, including, but not limited to, at least 80%, 81%, 82%, 83%, 84%, 85%, 86%, 87%, 88%, 89%, 90%, 91%, 92%, 93%, 94%, 95%, 96%, 97%, 98%, or 99% of the specificity and/or activity of the parent CDR.

While the site or region for introducing an amino acid sequence variation is predetermined, the mutation per se need not be predetermined. For example, in order to optimize the performance of a mutation at a given site, random mutagenesis may be conducted at the target codon or region and the expressed antigen binding protein CDR variants screened for the optimal combination of desired activity. Techniques for making substitution mutations at predetermined sites in DNA having a known sequence are well known, for example, M13 primer mutagenesis and PCR mutagenesis. Screening of the mutants is done using assays of antigen binding protein activities as described herein.

Amino acid substitutions are typically of single residues; insertions usually will be on the order of from about one (1) to about twenty (20) amino acid residues, although considerably larger insertions may be tolerated. Deletions range from about one (1) to about twenty (20) amino acid residues, although in some cases deletions may be much larger.

Substitutions, deletions, insertions or any combination thereof may be used to arrive at a final derivative or variant. Generally these changes are done on a few amino acids to minimize the alteration of the molecule, particularly the immunogenicity and specificity of the antigen binding protein. However, larger changes may be tolerated in certain circumstances.

By "Fab" or "Fab region" as used herein is meant the polypeptide that comprises the $V_H$, $C_H1$, $V_L$, and $C_L$ immunoglobulin domains. Fab may refer to this region in isolation, or this region in the context of a full length antibody, antibody fragment or Fab fusion protein, or any other antibody embodiments as outlined herein.

By "Fv" or "Fv fragment" or "Fv region" as used herein is meant a polypeptide that comprises the $V_L$ and $V_H$ domains of a single antibody.

By "framework" as used herein is meant the region of an antibody variable domain exclusive of those regions defined as CDRs. Each antibody variable domain framework can be further subdivided into the contiguous regions separated by the CDRs (FR1, FR2, FR3 and FR4).

The term "antigen-binding portion" of an antibody (or simply "antibody portion"), as used herein, refers to one or more fragments of an antibody that retain the ability to specifically bind to an antigen (e.g. BST1). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L/V_K$, $V_H$, $C_L$ and $C_H1$ domains; (ii) a F(ab')2 fragment, a bivalent fragment comprising two Fab fragments linked by a disulfide bridge at the hinge region; (iii) a Fab' fragment, which is essentially an Fab with part of the hinge region (see, FUNDAMENTAL IMMUNOLOGY (Paul ed., 3.sup.rd ed. 1993); (iv) a Fd fragment consisting of the $V_H$ and $C_H1$ domains; (v) a Fv fragment consisting of the $V_L$ and $V_H$ domains of a single arm of an antibody; (vi) a dAb fragment [Ward et al. (1989) Nature 341:544-546], which consists of a $V_H$ domain; (vii) an isolated complementarity determining region (CDR); and (viii) a Nanobody, a heavy chain variable region containing a single variable domain and two constant domains. Furthermore, although the two domains of the Fv fragment, $V_L/V_K$ and $V_H$, are coded for by separate genes, they can be joined, using recombinant methods, by a synthetic linker that enables them to be made as a single protein chain in which the $V_L/V_K$ and $V_H$ regions pair to form monovalent molecules (known as single chain Fv (scFv); see e.g. Bird et al. (1988) Science 242:423-426; and Huston et al. (1988) Proc. Natl. Acad. Sci. USA 85:5879-5883. Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody" as used herein, is intended to refer to an antibody that is substantially free of other antibodies having different antigenic specificities (e.g. an isolated antibody that specifically binds to the BST1 is substantially free of antibodies that specifically bind antigens other than the BST1). An isolated antibody that specifically binds to the BST1 may, however, have cross-reactivity to other antigens, such as BST1 molecules from other species. Moreover, and/or alternatively an isolated antibody may be substantially free of other cellular material and/or chemicals, that is in a form not normally found in nature.

In some embodiments, the antibodies of the invention are recombinant proteins, isolated proteins or substantially pure proteins. An "isolated" protein is unaccompanied by at least some of the material with which it is normally associated in its natural state, for example constituting at least about 5%, or at least about 50% by weight of the total protein in a given sample. It is understood that the isolated protein may constitute from 5 to 99.9% by weight of the total protein content depending on the circumstances. For example, the protein may be made at a significantly higher concentration through the use of an inducible promoter or high expression promoter, such that the protein is made at increased concentration levels. In the case of recombinant proteins, the definition includes the production of an antibody in a wide variety of organisms and/or host cells that are known in the art in which it is not naturally produced.

The terms "monoclonal antibody" or "monoclonal antibody composition" as used herein refer to a preparation of antibody molecules of single molecular composition. A monoclonal antibody composition displays a single binding specificity and affinity for a particular epitope. As used herein, a "polyclonal antibody" refers to antibodies produced by several clones of B-lymphocytes as would be the case in a whole animal.

As used herein, "isotype" refers to the antibody class (e.g. IgM or IgG1) that is encoded by the heavy chain constant region genes.

The phrases "an antibody recognizing an antigen" and "an antibody specific for an antigen" are used interchangeably herein with the term "an antibody which binds specifically to an antigen".

The term "antibody derivatives" refers to any modified form of the antibody, e.g. a conjugate (generally a chemical linkage) of the antibody and another agent or antibody. For example, antibodies of the present invention may be conjugated to agents, including, but not limited to, polymers (e.g. PEG) toxins, labels, etc. as is more fully described below. The antibodies of the present invention may be nonhuman, chimeric, humanized, or fully human. For a description of the concepts of chimeric and humanized antibodies, see Clark et al. (2000) and references cited therein (Clark, 2000, Immunol Today 21:397-402). Chimeric antibodies comprise the variable region of a nonhuman antibody, for example $V_H$ and $V_L$ domains of mouse or rat origin, operably linked to the constant region of a human antibody (see for example U.S. Pat. No. 4,816,567). In a preferred embodiment, the antibodies of the present invention are humanized. By "humanized" antibody as used herein is meant an antibody comprising a human framework region (FR) and one or more complementarity determining regions (CDR's) from a non-human (usually mouse or rat) antibody. The non-human antibody providing the CDR's is called the "donor" and the human immunoglobulin providing the framework is called the "acceptor". Humanization relies principally on the grafting of donor CDRs onto acceptor (human) $V_L$ and $V_H$ frameworks (U.S. Pat. No. 5,225,539). This strategy is referred to as "CDR grafting". "Backmutation" of selected acceptor framework residues to the corresponding donor residues is often required to regain affinity that is lost in the initial grafted construct (U.S. Pat. Nos. 5,530,101; 5,585,089; 5,693,761; 5,693,762; 6,180,370; 5,859,205; 5,821,337; 6,054,297; 6,407,213). The humanized antibody optimally also will comprise at least a portion of an immunoglobulin constant region, typically that of a human immunoglobulin, and thus will typically comprise a human Fc region. Methods for humanizing non-human antibodies are well known in the art, and can be essentially performed following the method of Winter and co-workers [Jones et al. (1986) Nature 321:522-525; Riechmann et al. (1988) Nature 332:323-329; Verhoeyen et al. (1988) Science, 239:1534-1536]. Additional examples of humanized murine monoclonal antibodies are also known in the art, for example antibodies binding human protein C (O'Connor et al., 1998, Protein Eng 11:321-8), interleukin 2 receptor [Queen et al. (1989) Proc Natl Acad Sci, USA 86:10029-33], and human epidermal growth factor receptor 2 [Carter et al. (1992) Proc Natl Acad Sci USA 89:4285-9]. In an alternate embodiment, the antibodies of the present invention may be fully human, that is the sequences of the antibodies are completely or substantially human. A number of methods are known in the art for generating fully human antibodies, including the use of transgenic mice [Bruggemann et al. (1997) Curr Opin Biotechnol 8:455-458] or human antibody libraries coupled with selection methods [Griffiths et al. (1998) Curr Opin Biotechnol 9:102-108].

The term "humanized antibody" is intended to include antibodies in which CDR sequences derived from the germline of another mammalian species, such as a mouse, have been grafted onto human framework sequences. Additional framework region modifications may be made within the human framework sequences, such as Fc domain amino acid modifications, as is described herein.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

The term "specifically binds" (or "immunospecifically binds") is not intended to indicate that an antibody binds exclusively to its intended target, although in many embodiments this will be true; that is, an antibody "specifically binds" to its target and does not detectably or substantially bind to other components in the sample, cell or patient. However, in some embodiments, an antibody "specifically binds" if its affinity for its intended target is about 5-fold greater when compared to its affinity for a non-target molecule. Suitably there is no significant cross-reaction or cross-binding with undesired substances, especially naturally occurring proteins or tissues of a healthy person or animal. The affinity of the antibody will, for example, be at least about 5-fold, such as 10-fold, such as 25-fold, especially 50-fold, and particularly 100-fold or more, greater for a target molecule than its affinity for a non-target molecule. In some embodiments, specific binding between an antibody or other binding agent and an antigen means a binding affinity of at least $10^6$ M$^{-1}$. Antibodies may, for example, bind with affinities of at least about $10^7$ M$^{-1}$, such as between about $10^8$ M$^{-1}$ to about $10^9$ M$^{-1}$, about $10^9$ M$^{-1}$ to about $10^{10}$ M$^{-1}$, or about $10^{10}$ M$^{-1}$ to about $10^{11}$ M$^{-1}$. Antibodies may, for example, bind with an $EC_{50}$ of 50 nM or less, 10 nM or less, 1 nM or less, 100 pM or less, or more preferably 10 pM or less.

The term "does not substantially bind" to a protein or cells, as used herein, means does not bind or does not bind with a high affinity to the protein or cells, i.e. binds to the protein or cells with a $K_D$ of $1 \times 10^{-6}$ M or more, more preferably $1 \times 10^{-5}$ M or more, more preferably $1 \times 10^4$ M or more, more preferably $1 \times 10^{-3}$ M or more, even more preferably $1 \times 10^{-2}$ M or more.

The term "$EC_{50}$" as used herein, is intended to refer to the potency of a compound by quantifying the concentration that leads to 50% maximal response/effect. $EC_{50}$ may be determined by Scratchard or FACS.

The term "$K_{assoc}$" or "$K_a$," as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$," as used herein, is intended to refer to the affinity constant, which is obtained from the ratio of $K_d$ to $K_a$ (i.e. $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

As used herein, the term "high affinity" for an IgG antibody refers to an antibody having a $K_D$ of $1 \times 10^{-7}$ M or less, more preferably $5 \times 10^{-8}$ M or less, even more preferably $1 \times 10^{-8}$ M or less, even more preferably $5 \times 10^{-9}$ M or less and even more preferably $1 \times 10^{-9}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

The term "epitope" or "antigenic determinant" refers to a site on an antigen to which an immunoglobulin or antibody specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art and those described herein, for example, x-ray crystallography and 2-dimensional nuclear magnetic resonance [see, e.g. Epitope Mapping Protocols in Methods in Molecular Biology, Vol. 66, G. E. Morris, Ed. (1996)].

Accordingly, also encompassed by the present invention are antibodies that bind to (i.e. recognize) the same epitope as the antibodies described herein (i.e. BST1_A2, BST1_A1 and BST1_A3). Antibodies that bind to the same epitope can be identified by their ability to cross-compete with (i.e. competitively inhibit binding of) a reference antibody to a target antigen in a statistically significant manner. Competitive inhibition can occur, for example, if the antibodies bind to identical or structurally similar epitopes (e.g. overlapping epitopes), or spatially proximal epitopes which, when bound, causes steric hindrance between the antibodies.

Competitive inhibition can be determined using routine assays in which the immunoglobulin under test inhibits specific binding of a reference antibody to a common antigen. Numerous types of competitive binding assays are known, for example: solid phase direct or indirect radioimmunoassay (RIA), solid phase direct or indirect enzyme immunoassay (EIA), sandwich competition assay [see Stahl et al. (1983) *Methods in Enzymology* 9:242]; solid phase direct biotin-avidin EIA [see Kirkland et al. (1986) *J. Immunol.* 137:3614]; solid phase direct labeled assay, solid phase direct labeled sandwich assay [see Harlow and Lane (1988) *Antibodies: A Laboratory Manual*, Cold Spring Harbor Press]; solid phase direct label RIA using I-125 label [see Morel et al. (1988) *Mol. Immunol.* 25(1):7)]; solid phase direct biotin-avidin EIA [Cheung et al. (1990) *Virology* 176:546]; and direct labeled RIA. [Moldenhauer et al. (1990) *Scand. J. Immunol.* 32:77]. Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

Other techniques include, for example, epitope mapping methods, such as x-ray analyses of crystals of antigen: antibody complexes which provides atomic resolution of the epitope. Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. The peptides are then regarded as leads for the definition of the epitope corresponding to the antibody used to screen the peptide library. For epitope mapping, computational algorithms have also been developed which have been shown to map conformational discontinuous epitopes.

As used herein, the term "subject" includes any human or nonhuman animal. The term "nonhuman animal" includes all vertebrates, e.g. mammals and non-mammals, such as nonhuman primates, sheep, dogs, cats, horses, cows, chickens, amphibians, reptiles, etc.

Various aspects of the disclosure are described in further detail in the following subsections.

Anti-BST1 Antibodies

The antibodies of the invention are characterized by particular functional features or properties of the antibodies. For example, the antibodies bind specifically to the human BST1. Preferably, an antibody of the invention binds to the BST1 with high affinity, for example, with a $K_D$ of $8 \times 10^{-7}$ M or less, even more typically $1 \times 10^{-8}$ M or less. The anti-BST1 antibodies of the invention preferably exhibit one or more of the following characteristics, with antibodies exhibiting both finding particular use:

binds to the human BST1 with a $EC_{50}$ of 50 nM or less, 10 nM or less, 1 nM or less, 100 pM or less, or more preferably 10 pM or less;

binds to human cells expressing the BST1.

In one embodiment, the antibodies preferably bind to an antigenic epitope present in the BST1, which epitope is not present in other proteins. Preferably, the antibodies do not bind to related proteins, for example, the antibodies do not substantially bind to other cell adhesion molecules. In one embodiment, the antibody may be internalized into a cell expressing the BST1. Standard assays to evaluate antibody internalization are known in the art, including, for example, MabZap or HumZap internalization assays.

Standard assays to evaluate the binding ability of the antibodies toward the BST1 can be done on the protein or cellular level and are known in the art, including for example, ELISAs, Western blots, RIAs, BIAcore® assays and flow cytometry analysis. Suitable assays are described in detail in the Examples. The binding kinetics (e.g. binding affinity) of the antibodies also can be assessed by standard assays known in the art, such as by Biacore® system analysis. To assess binding to Raji or Daudi B cell tumor cells, Raji (ATCC Deposit No. CCL-86) or Daudi (ATCC Deposit No. CCL-213) cells can be obtained from publicly available sources, such as the American Type Culture Collection, and used in standard assays, such as flow cytometric analysis.

Monoclonal Antibodies of the Invention

Preferred antibodies of the invention are the monoclonal antibodies BST1_A2 and BST1_A1 isolated and structurally characterized as described in Examples 1-4. The $V_H$ amino acid sequences BST1_A2, BST1_A1 and BST1_A3 are shown in SEQ ID NOs: 2, 1 and 52, respectively. The $V_K$ amino acid sequences BST1_A2, BST1_A1 and BST1_A3 are shown in SEQ ID NOs: 4, 3 and 53, respectively.

Given that each of these antibodies can bind to the BST1, the $V_H$ and $V_K$ sequences can be "mixed and matched" to create other anti-BST1 binding molecules of the invention. The BST1 binding of such "mixed and matched" antibodies can be tested using the binding assays described above and in the Examples (e.g. ELISAs). Preferably, when $V_H$ and $V_K$ chains are mixed and matched, a $V_H$ sequence from a particular $V_H/V_K$ pairing is replaced with a structurally similar $V_H$ sequence. Likewise, preferably a $V_K$ sequence from a particular $V_H/V_K$ pairing is replaced with a structurally similar $V_K$ sequence.

Accordingly, in one aspect, the invention provides an antibody, comprising: a heavy chain variable region comprising an amino acid sequence set forth in a SEQ ID NO: selected from the group consisting of 2, 1 and 52 and a light chain variable region comprising an amino acid sequence set forth in a SEQ ID NO: selected from the group consisting 4, 3 and 53; wherein the antibody specifically binds to the BST1, preferably the human BST1.

Preferred heavy and light chain combinations include:
a heavy chain variable region comprising the amino acid sequence of SEQ ID NO: 2 and a light chain variable region comprising the amino acid sequence of SEQ ID NO: 4; or
a heavy chain variable region comprising the amino acid sequence of SEQ ID NO: 1 and a light chain variable region comprising the amino acid sequence of SEQ ID NO: 3; or
a heavy chain variable region comprising the amino acid sequence of SEQ ID NO: 52 and a light chain variable region comprising the amino acid sequence of SEQ ID NO: 53.

In another aspect, the invention provides antibodies that comprise the heavy chain and light chain CDR1s, CDR2s and CDR3s of BST1_A2, BST1_A1 and BST1_A3, or combinations thereof. The amino acid sequences of the $V_H$ CDR1s of BST1_A2, BST1_A1 and BST1_A3 are shown in SEQ ID NOs: 10, 9 and 56, respectively. The amino acid sequences of the $V_H$ CDR2s of BST1_A2, BST1_A1 and BST1_A3 are shown in SEQ ID NOs: 12 or 51, 11 and 57, respectively. The amino acid sequences of the $V_H$ CDR3s of BST1_A2, BST1_A1 and BST1_A3 are shown in SEQ ID NOs: 14, 13 and 58, respectively. The amino acid sequences of the $V_K$ CDR1s of BST1_A2, BST1_A1 and BST1_A3 are shown in SEQ ID NOs: 16, 15 and 59, respectively. The amino acid sequences of the $V_K$ CDR2s of BST1_A2, BST1_A1 and BST1_A3 are shown in SEQ ID NOs: 18, 17 and 60, respectively. The amino acid sequences of the $V_K$ CDR3 s of BST1_A2, BST1_A1 and BST1_A3 are shown in SEQ ID NOs: 20, 19 and 61, respectively. The CDR regions are delineated using the Kabat system [Kabat, E. A. et al. (1991) Sequences of Proteins of Immunological Interest, Fifth Edition, US Department of Health and Human Services, NIH Publication No. 91-3242].

Given that each of these antibodies can bind to the BST1 and that antigen-binding specificity is provided primarily by the CDR1, CDR2, and CDR3 regions, the $V_H$ CDR1, CDR2, and CDR3 sequences and $V_K$ CDR1, CDR2, and CDR3 sequences can be "mixed and matched" (i.e. CDRs from different antibodies can be mixed and matched, although each antibody generally contains a $V_H$ CDR1, CDR2, and CDR3 and a $V_K$ CDR1, CDR2, and CDR3) to create other anti-BST1 binding molecules of the invention. Accordingly, the invention specifically includes every possible combination of CDRs of the heavy and light chains.

The BST1 binding of such "mixed and matched" antibodies can be tested using the binding assays described above and in the Examples (e.g. ELISAs, Biacore® analysis). Preferably, when $V_H$ CDR sequences are mixed and matched, the CDR1, CDR2 and/or CDR3 sequence from a particular $V_H$ sequence is replaced with a structurally similar CDR sequence(s). Likewise, when $V_K$ CDR sequences are mixed and matched, the CDR1, CDR2 and/or CDR3 sequence from a particular $V_K$ sequence preferably is replaced with a structurally similar CDR sequence(s). It will be readily apparent to the ordinarily skilled artisan that novel $V_H$ and $V_K$ sequences can be created by substituting one or more $V_H$ and/or $V_L/V_K$ CDR region sequences with structurally similar sequences from the CDR sequences disclosed herein for monoclonal antibodies BST1_A2, BST1_A1 and BST1_A3.

Accordingly, in another aspect, the invention provides an isolated monoclonal antibody, or antigen binding portion thereof comprising:
a heavy chain variable region CDR1 comprising an amino acid sequence selected from the group consisting of SEQ ID NOs: 10, 9 and 56;
a heavy chain variable region CDR2 comprising an amino acid sequence selected from the group consisting of SEQ ID NOs: 12 or 51, 11 and 57;
a heavy chain variable region CDR3 comprising an amino acid sequence selected from the group consisting of SEQ ID NOs: 14, 13 and 58;
a light chain variable region CDR1 comprising an amino acid sequence selected from the group consisting of SEQ ID NOs: 16, 15 and 59;
a light chain variable region CDR2 comprising an amino acid sequence selected from the group consisting of SEQ ID NOs: 18, 17 and 60; and
a light chain variable region CDR3 comprising an amino acid sequence selected from the group consisting of SEQ ID NOs: 20, 19 and 61;
with all possible combinations being possible, wherein the antibody specifically binds to the BST1, preferably the human BST1.

In another preferred embodiment, the antibody possesses:
a heavy chain variable region CDR1 comprising SEQ ID NO: 10;
a heavy chain variable region CDR2 comprising SEQ ID NO: 12 or SEQ ID NO: 51;
a heavy chain variable region CDR3 comprising SEQ ID NO: 14; and
a light chain variable region CDR1 comprising SEQ ID NO: 16;
a light chain variable region CDR2 comprising SEQ ID NO: 18;
a light chain variable region CDR3 comprising SEQ ID NO: 20.

In another preferred embodiment, the antibody possesses:
a heavy chain variable region CDR1 comprising SEQ ID NO: 9;
a heavy chain variable region CDR2 comprising SEQ ID NO: 11;
a heavy chain variable region CDR3 comprising SEQ ID NO: 13; and
a light chain variable region CDR1 comprising SEQ ID NO: 15;
a light chain variable region CDR2 comprising SEQ ID NO: 17;
a light chain variable region CDR3 comprising SEQ ID NO: 19.

In another preferred embodiment, the antibody possesses:
a heavy chain variable region CDR1 comprising SEQ ID NO: 56;
a heavy chain variable region CDR2 comprising SEQ ID NO: 57;
a heavy chain variable region CDR3 comprising SEQ ID NO: 58; and
a light chain variable region CDR1 comprising SEQ ID NO: 59;
a light chain variable region CDR2 comprising SEQ ID NO: 60;
a light chain variable region CDR3 comprising SEQ ID NO: 61.

It is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, for example, Klimka et al. (2000) *British J. of Cancer* 83(2):252-260 (describing the production of a humanized anti-CD30 antibody using only the heavy chain variable domain CDR3 of murine anti-CD30 antibody Ki-4); Beiboer et al. (2000) *J. Mol. Biol.* 296:833-849 (describing recombinant epithelial glycoprotein-2 (EGP-2) antibodies using only the heavy chain CDR3 sequence of the parental murine MOC-31 anti-EGP-2 antibody); Rader et al. (1998) *Proc. Natl. Acad. Sci. USA.* 95:8910-8915 (describing a panel of humanized anti-integrin $\alpha_v\beta3$ antibodies using a heavy and light chain variable CDR3 domain of a murine anti-integrin $\alpha_v\beta3$ antibody LM609 wherein each member antibody comprises a distinct sequence outside the CDR3 domain and capable of binding the same epitope as the parent murine antibody with affinities as high or higher than the parent murine antibody); Barbas et al. (1994) *J. Am. Chem. Soc.* 116:2161-2162

(disclosing that the CDR3 domain provides the most significant contribution to antigen binding); Barbas et al. (1995) *Proc. Natl. Acad. Sci. USA*. 92:2529-2533 (describing the grafting of heavy chain CDR3 sequences of three Fabs (SI-1, SI-40, and SI-32) against human placental DNA onto the heavy chain of an anti-tetanus toxoid Fab thereby replacing the existing heavy chain CDR3 and demonstrating that the CDR3 domain alone conferred binding specificity); and Ditzel et al. (1996) *J. Immunol*. 157:739-749 (describing grafting studies wherein transfer of only the heavy chain CDR3 of a parent polyspecific Fab LNA3 to a heavy chain of a monospecific IgG tetanus toxoid-binding Fab p313 antibody was sufficient to retain binding specificity of the parent Fab). Each of these references is hereby incorporated by reference in its entirety.

Accordingly, the present invention provides monoclonal antibodies comprising one or more heavy and/or light chain CDR3 domains from an antibody derived from a human or non-human animal, wherein the monoclonal antibody is capable of specifically binding to the BST1. Within certain aspects, the present invention provides monoclonal antibodies comprising one or more heavy and/or light chain CDR3 domain from a non-human antibody, such as a mouse or rat antibody, wherein the monoclonal antibody is capable of specifically binding to the BST1. Within some embodiments, such inventive antibodies comprising one or more heavy and/or light chain CDR3 domain from a non-human antibody (a) are capable of competing for binding with; (b) retain the functional characteristics; (c) bind to the same epitope; and/or (d) have a similar binding affinity as the corresponding parental non-human antibody.

Within other aspects, the present invention provides monoclonal antibodies comprising one or more heavy and/or light chain CDR3 domains from a human antibody, such as, for example, a human antibody obtained from a non-human animal, wherein the human antibody is capable of specifically binding to the BST1. Within other aspects, the present invention provides monoclonal antibodies comprising one or more heavy and/or light chain CDR3 domain from a first human antibody, such as, for example, a human antibody obtained from a non-human animal, wherein the first human antibody is capable of specifically binding to the BST1 and wherein the CDR3 domain from the first human antibody replaces a CDR3 domain in a human antibody that is lacking binding specificity for the BST1 to generate a second human antibody that is capable of specifically binding to the BST1. Within some embodiments, such inventive antibodies comprising one or more heavy and/or light chain CDR3 domain from the first human antibody (a) are capable of competing for binding with; (b) retain the functional characteristics; (c) bind to the same epitope; and/or (d) have a similar binding affinity as the corresponding parental first human antibody.

Antibodies Having Particular Germline Sequences

In certain embodiments, an antibody of the invention comprises a heavy chain variable region from a particular germline heavy chain immunoglobulin gene and/or a light chain variable region from a particular germline light chain immunoglobulin gene.

For example, in a preferred embodiment, the invention provides an isolated monoclonal antibody, or an antigen-binding portion thereof, comprising a heavy chain variable region that is the product of or derived from a murine$V_H$ 1-39 gene, murine$V_H$ 1-80 gene or a murine $V_H$ 69-1 gene, wherein the antibody specifically binds to the BST1. In yet another preferred embodiment, the invention provides an isolated monoclonal antibody, or an antigen-binding portion thereof, comprising a light chain variable region that is the product of or derived from a murine $V_K$ 4-55 gene, murine $V_K$ 4-74 gene or a murine $V_K$ 44-1 gene, wherein the antibody specifically binds to the BST1.

In yet another preferred embodiment, the invention provides an isolated monoclonal antibody, or antigen-binding portion thereof, wherein the antibody:
  comprises a heavy chain variable region that is the product of or derived from a murine $V_H$ 1-39 gene (which gene includes the nucleotide sequence set forth in SEQ ID NOs: 35 and 36); comprises a light chain variable region that is the product of or derived from a murine $V_K$ 4-55 gene (which gene includes the nucleotide sequences set forth in SEQ ID NOs: 40, 41 and 42); and specifically binds to the BST1, preferably the human BST1. Examples of antibodies having $V_H$ 1-39 and $V_K$ 4-55 genes, with sequences described above, are BST1_A2.

In yet another preferred embodiment, the invention provides an isolated monoclonal antibody, or antigen-binding portion thereof, wherein the antibody:
  comprises a heavy chain variable region that is the product of or derived from a murine $V_H$ 1-80 gene (which gene includes the nucleotide sequence set forth in SEQ ID NOs: 33 and 34);
comprises a light chain variable region that is the product of or derived from a murine $V_K$ 4-74 gene (which gene includes the nucleotide sequences set forth in SEQ ID NOs: 37, 38 and 39); and specifically binds to the BST1, preferably the human BST1. An example of an antibody having $V_H$ 1-80 and $V_K$ 4-74 genes, with sequences described above, is BST1_A1.

In yet another preferred embodiment, the invention provides an isolated monoclonal antibody, or antigen-binding portion thereof, wherein the antibody:
  comprises a heavy chain variable region that is the product of or derived from a murine $V_H$ 69-1 gene (which gene includes the nucleotide sequence set forth in SEQ ID NOs: 68 and 69);
comprises a light chain variable region that is the product of or derived from a murine $V_K$ 44-1 gene (which gene includes the nucleotide sequences set forth in SEQ ID NOs: 70, 71 and 72); and specifically binds to the BST1, preferably the human BST1. An example of an antibody having $V_H$ and $V_K$ genes, with sequences described above, is BST1_A3.

As used herein, an antibody comprises heavy or light chain variable regions that is "the product of" or "derived from" a particular germline sequence if the variable regions of the antibody are obtained from a system that uses murine germline immunoglobulin genes. Such systems include screening a murine immunoglobulin gene library displayed on phage with the antigen of interest. An antibody that is "the product of" or "derived from" a murine germline immunoglobulin sequence can be identified as such by comparing the nucleotide or amino acid sequence of the antibody to the nucleotide or amino acid sequences of murine germline immunoglobulins and selecting the murine germline immunoglobulin sequence that is closest in sequence (i.e. greatest % identity) to the sequence of the antibody. An antibody that is "the product of" or "derived from" a particular murine germline immunoglobulin sequence may contain amino acid differences as compared to the germline sequence, due to, for example, naturally-occurring somatic mutations or intentional introduction of site-directed mutation. However, a selected antibody typically is at least 90% identical in amino acids sequence to an amino acid sequence encoded by a murine germline immunoglobulin gene and contains amino acid residues that identify the antibody as being murine when compared to the germline immunoglobulin amino acid sequences of other species (e.g. human germline sequences). In certain cases, an antibody may be at least 95%, or even at least 96%, 97%, 98%, or 99% identical in amino acid sequence to the amino acid sequence encoded by the germline immunoglobulin gene. Typically, an antibody derived from a particular murine germline sequence will display no more than 10 amino acid differences from the amino acid sequence encoded by the murine germline immunoglobulin gene. In certain cases, the antibody may display no more than 5, or even no more than 4, 3, 2, or 1 amino acid difference from the amino acid sequence encoded by the germline immunoglobulin gene.

Homologous Antibodies

In yet another embodiment, an antibody of the invention comprises heavy and light chain variable regions comprising amino acid sequences that are homologous to the amino acid sequences of the preferred antibodies described herein, and wherein the antibodies retain the desired functional properties of the anti-BST1 antibodies of the invention.

For example, the invention provides an isolated monoclonal antibody, or antigen binding portion thereof, comprising a heavy chain variable region and a light chain variable region, wherein: the heavy chain variable region comprises an amino acid sequence that is at least 80% identical to an amino acid sequence selected from the group consisting of SEQ ID NOs: 2, 1 and 52; the light chain variable region comprises an amino acid sequence that is at least 80% identical to an amino acid sequence selected from the group consisting of SEQ ID NOs: 4, 3 and 53; and the antibody binds to human BST1. Such antibodies may bind to human BST1 with an $EC_{50}$ of 50 nM or less, 10 nM or less, 1 nM or less, 100 pM or less, or more preferably 10 pM or less.

The antibody may also bind to CHO cells transfected with the human BST1.

In various embodiments, the antibody can be, for example, a human antibody, a humanized antibody or a chimeric antibody.

In other embodiments, the $V_H$ and/or $V_K$ amino acid sequences may be 85%, 90%, 95%, 96%, 97%, 98% or 99% homologous to the sequences set forth above. An antibody having $V_H$ and $V_K$ regions having high (i.e. 80% or greater) identical to the $V_H$ and $V_K$ regions of the sequences set forth above, can be obtained by mutagenesis (e.g. site-directed or PCR-mediated mutagenesis) of nucleic acid molecules encoding SEQ ID NOs: 6, 5, 8, 7, 54 and 55 followed by testing of the encoded altered antibody for retained function using the functional assays described herein.

The percent identity between the two sequences is a function of the number of identical positions shared by the sequences (i.e. % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller [*Comput. Appl. Biosci.* (1988) 4:11-17] which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch [*J. Mol. Biol.* (1970) 48:444-453] algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al. (1990) *J. Mol. Biol.* 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g. XBLAST and NBLAST) can be used. See www.ncbi.nlm.nih.gov.

Antibodies with Conservative Modifications

In certain embodiments, an antibody of the invention comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein (e.g. BST1_A2, BST1_A1 and BST1_A3), or conservative modifications thereof, and wherein the antibodies retain the desired functional properties of the anti-BST1 antibodies of the invention. Accordingly, the invention provides an isolated monoclonal antibody, or antigen binding portion thereof, comprising a heavy chain variable region comprising CDR1, CDR2, and CDR3 sequences and a light chain variable region comprising CDR1, CDR2, and CDR3 sequences, wherein: the heavy chain variable region CDR3 sequence comprises an amino acid sequence selected from the group consisting of amino acid sequences of SEQ ID NOs: 14, 13 and 58, and conservative modifications thereof; the light chain variable region CDR3 sequence comprises an amino acid sequence selected from the group consisting of amino acid sequence of SEQ ID NOs: 20, 19 and 61, and conservative modifications thereof; and the antibody binds to human BST1 with a $EC_{50}$ of 50 nM or less, 10 nM or less, 1 nM or less, 100 pM or less, or more preferably 10 pM or less.

The antibody may also bind to CHO cells transfected with human BST1.

In a preferred embodiment, the heavy chain variable region CDR2 sequence comprises an amino acid sequence selected from the group consisting of amino acid sequences of SEQ ID NOs: 12 or 51, 11 and 57, and conservative modifications thereof; and the light chain variable region CDR2 sequence comprises an amino acid sequence selected from the group consisting of amino acid sequences of SEQ ID NOs: 18, 17 and 60, and conservative modifications thereof. In another preferred embodiment, the heavy chain variable region CDR1 sequence comprises an amino acid sequence selected from the group consisting of amino acid sequences of SEQ ID NOs: 10, 9 and 56, and conservative modifications thereof; and the light chain variable region CDR1 sequence comprises an amino acid sequence selected from the group consisting of amino acid sequences of SEQ ID NOs: 16, 15 and 59, and conservative modifications thereof. In another preferred embodiment, the heavy chain variable region CDR3 sequence comprises an amino acid sequence selected from the group consisting of amino acid sequences of SEQ ID NOs: 14, 13 and 58, and conservative modifications thereof; and the light chain variable region CDR3 sequence comprises an amino acid sequence selected from the group consisting of amino acid sequences of SEQ ID NOs: 20, 19 and 61, and conservative modifications thereof.

In a preferred embodiment, the heavy chain variable region CDR2 sequence comprises an amino acid sequence selected from the group consisting of amino acid sequences of SEQ ID NOs: 12 or 51, 11 and 57, and conservative modifications thereof; and the light chain variable region CDR2 sequence comprises an amino acid sequence selected from the group consisting of amino acid sequences of SEQ ID NOs: 18, 17 and 60, and conservative modifications thereof. In another preferred embodiment, the heavy chain variable region CDR1 sequence comprises an amino acid sequence selected from the group consisting of amino acid sequences of SEQ ID NOs: 10, 9 and 56, and conservative modifications thereof; and the light chain variable region CDR1 sequence comprises an amino acid sequence selected from the group consisting of amino acid sequences of SEQ ID NOs: 16, 15 and 59, and conservative modifications thereof.

In various embodiments, the antibody can be, for example, human antibodies, humanized antibodies or chimeric antibodies.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g. lysine, arginine, histidine), acidic side chains (e.g. aspartic acid, glutamic acid), uncharged polar side chains (e.g. glycine, asparagine, glutamine, serine, threonine, tyrosine, cysteine, tryptophan), nonpolar side chains (e.g. alanine, valine, leucine, isoleucine, proline, phenylalanine, methionine), beta-branched side chains (e.g. threonine, valine, isoleucine) and aromatic side chains (e.g. tyrosine, phenylalanine, tryptophan, histidine). Thus, one or more amino acid residues within the CDR regions of an antibody of the invention can be replaced with other amino acid residues from the same side chain family and the altered antibody can be tested for retained function using the functional assays described herein.

The heavy chain CDR1 sequences of SEQ ID NOs: 10, 9 and 56 may comprise one or more conservative sequence modification, such as one, two, three, four, five or more amino acid substitutions, additions or deletions; the light chain CDR1 sequences of SEQ ID NOs: 16, 15 and 59 may comprise one or more conservative sequence modification, such as one, two, three, four, five or more amino acid substitutions, additions or deletions; the heavy chain CDR2 sequences shown in SEQ ID NO: 12 or 51, 11 and 57 may comprise one or more conservative sequence modification, such as one, two, three, four, five or more amino acid substitutions, additions or deletions; the light chain CDR2 sequences shown in SEQ ID NOs: 18, 17 and 60 may comprise one or more conservative sequence modification, such as one, two, three, four, five or more amino acid substitutions, additions or deletions; the heavy chain CDR3 sequences shown in SEQ ID NOs: 14, 13 and 58 may comprise one or more conservative sequence modification, such as one, two, three, four, five or more amino acid substitutions, additions or deletions; and/or the light chain CDR3 sequences shown in SEQ ID NOs: 20, 19 and 61 may comprise one or more conservative sequence modification, such as one, two, three, four, five or more amino acid substitutions, additions or deletions.

Antibodies that Bind to the Same Epitope as Anti-BST1 Antibodies of the Invention In another embodiment, the invention provides antibodies that bind to the same epitope on the human BST1 as any of the BST1 monoclonal antibodies of the invention (i.e. antibodies that have the ability to cross-compete for binding to the BST1 with any of the monoclonal antibodies of the invention). In preferred embodiments, the reference antibody for cross-competition studies can be the monoclonal antibody BST1_A2 (having $V_H$ and $V_K$ sequences as shown in SEQ ID NOs: 2 and 4, respectively), the monoclonal antibody BST1_A1 (having $V_H$ and $V_K$ sequences as shown in SEQ ID NOs: 1 and 3, respectively), the monoclonal antibody BST1_A3 (having $V_H$ and $V_K$ sequences as shown in SEQ ID NOs: 52 and 53, respectively).

Such cross-competing antibodies can be identified based on their ability to cross-compete with BST1_A2, BST1_A1 and BST1_A3 in standard BST1 binding assays. For example, BIAcore analysis, ELISA assays or flow cytometry may be used to demonstrate cross-competition with the antibodies of the current invention. The ability of a test antibody to inhibit the binding of, for example, BST1_A2, BST1_A1 and BST1_A3, to human BST1 demonstrates that the test antibody can compete with BST1_A2, BST1_A1 or BST1_A3 for binding to human BST1 and thus binds to the same epitope on human BST1_A2, BST1_A1 or BST1_A3.

Engineered and Modified Antibodies

An antibody of the invention can be prepared using an antibody having one or more of the $V_H$ and/or $V_L$ sequences disclosed herein which can be used as starting material to engineer a modified antibody, which modified antibody may have altered properties as compared to the starting antibody. An antibody can be engineered by modifying one or more amino acids within one or both variable regions (i.e. $V_H$ and/or $V_L$), for example, within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g. Riechmann, L. et al. (1998) *Nature* 332:323-327; Jones, P. et al. (1986) *Nature* 321:522-525; Queen, C. et al. (1989) *Proc. Natl. Acad. See. USA*. 86:10029-10033; U.S. Pat. No. 5,225, 539 to Winter, and U.S. Pat. Nos. 5,530,101; 5,585,089; 5,693,762 and 6,180,370 to Queen et al.).

Accordingly, another embodiment of the invention pertains to an isolated monoclonal antibody, or antigen binding portion thereof, comprising a heavy chain variable region comprising CDR1, CDR2, and CDR3 sequences comprising an amino acid sequence selected from the group consisting of SEQ ID NOs 10, 9 and 56; 12 or 51, 11 and 57; and 14, 13 and 58, respectively, and a light chain variable region comprising CDR1, CDR2, and CDR3 sequences comprising an amino acid sequence selected from the group consisting of SEQ ID NOs: 16, 15 and 59; 18, 17 and 60; and 20, 19 and 61, respectively. Thus, such antibodies contain the $V_H$ and $V_K$ CDR sequences of monoclonal antibodies BST1_A2, BST1_A1 and BST1_A3, yet may contain different framework sequences from these antibodies.

Such framework sequences can be obtained from public DNA databases or published references that include germline antibody gene sequences. For example, germline DNA sequences for murine heavy and light chain variable region genes can be found in the IMGT (international ImMunoGeneTics) murine germline sequence database (available at hypertext transfer protocol//www.imgt.cines.fr/?), as well as in Kabat, E. A., et al. (1991) Sequences of Proteins of Immunological Interest, Fifth Edition, US Department of Health and Human Services, NIH Publication No. 91-3242; the contents of each of which are expressly incorporated herein by reference. As another example, the germline DNA sequences for murine heavy and light chain variable region genes can be found in the Genbank database.

Antibody protein sequences are compared against a compiled protein sequence database using one of the sequence similarity searching methods called the Gapped BLAST [Altschul et al. (1997) *Nucleic Acids Research* 25:3389-3402], which is well known to those skilled in the art. BLAST is a heuristic algorithm in that a statistically significant alignment between the antibody sequence and the database sequence is likely to contain high-scoring segment pairs (HSP) of aligned words. Segment pairs whose scores cannot be improved by extension or trimming is called a hit. Briefly, the nucleotide sequences in the database are translated and the region between and including FR1 through FR3 framework region is retained. The database sequences have an average length of 98 residues. Duplicate sequences which are exact matches over the entire length of the protein are removed. A BLAST search for proteins using the program blastp with default, standard parameters except the low complexity filter, which is turned off, and the substitution matrix of BLOSUM62, filters for top 5 hits yielding sequence matches. The nucleotide sequences are translated in all six frames and the frame with no stop codons in the matching segment of the database sequence is considered the potential hit. This is in turn confirmed using the BLAST program tblastx, which translates the antibody sequence in all six frames and compares those translations to the nucleotide sequences in the database dynamically translated in all six frames.

The identities are exact amino acid matches between the antibody sequence and the protein database over the entire length of the sequence. The positives (identities+substitution match) are not identical but amino acid substitutions guided by the BLOSUM62 substitution matrix. If the antibody sequence matches two of the database sequences with same identity, the hit with most positives would be decided to be the matching sequence hit.

Preferred framework sequences for use in the antibodies of the invention are those that are structurally similar to the framework sequences used by selected antibodies of the invention, e.g., similar to the $V_H$ 1-80 framework sequence, the $V_H$ 1-39 framework sequence, the $V_K$ 4-74 framework sequence and/or the $V_K$ 4-55 framework sequences used by preferred monoclonal antibodies of the invention. The $V_H$ CDR1, CDR2, and CDR3 sequences, and the $V_K$ CDR1, CDR2, and CDR3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see, e.g., U.S. Pat. Nos. 5,530,101; 5,585,089; 5,693,762 and 6,180,370 to Queen et al.).

Another type of variable region modification is to mutate amino acid residues within the $V_H$ and/or $V_K$ CDR1, CDR2 and/or CDR3 regions to thereby improve one or more binding properties (e.g. affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. In some embodiments, conservative modifications (as discussed above) are introduced. Alternatively, non-conservative modifications can be made. The mutations may be amino acid substitutions, additions or deletions, but are preferably substitutions. Moreover, typically no more than one, two, three, four or five residues within a CDR region are altered, although as will be appreciated by those in the art, variants in other areas (framework regions for example) can be greater.

Accordingly, in another embodiment, the instant disclosure provides isolated anti-BST1 monoclonal antibodies, or antigen binding portions thereof, comprising a heavy chain variable region comprising: (a) a $V_H$ CDR1 region comprising an amino acid sequence selected from the group consisting of SEQ ID NOs: 10, 9 and 56 or an amino acid sequence having one, two, three, four or five amino acid substitutions, deletions or additions as compared to SEQ ID NOs: 10, 9 and 56; (b) a $V_H$ CDR2 region comprising an amino acid sequence selected from the group consisting of SEQ ID NOs: 12 or 51, 11 and 57, or an amino acid sequence having one, two, three, four or five amino acid substitutions, deletions or additions as compared to SEQ ID NOs: 12 or 51, 11 and 57; (c) a $V_H$ CDR3 region comprising an amino acid sequence selected from the group consisting of SEQ ID NOs: 14, 13 and 58, or an amino acid sequence having one, two, three, four or five amino acid substitutions, deletions or additions as compared to SEQ ID NOs: 14, 13 and 58; (d) a $V_K$ CDR1 region comprising an amino acid sequence selected from the group consisting of SEQ ID NOs: 16, 15 and 59, or an amino acid sequence having one, two, three, four or five amino acid substitutions, deletions or additions as compared to SEQ ID NOs: 16, 15 and 59; (e) a $V_K$ CDR2 region comprising an amino acid sequence selected from the group consisting of SEQ ID NOs: 18, 17 and 60, or an amino acid sequence having one, two, three, four or five amino acid substitutions, deletions or additions as compared to SEQ ID NOs: 18, 17 and 60; and (f) a $V_K$ CDR3 region comprising an amino acid sequence selected from the group consisting of SEQ ID NOs: 20, 19 and 61, or an amino acid sequence having one, two, three, four or five amino acid substitutions, deletions or additions as compared to SEQ ID NOs: 20, 19 and 61.

Engineered antibodies of the disclosure include those in which modifications have been made to framework residues within $V_H$ and/or $V_K$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in US Patent Publication No. 2003/0153043.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g. one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of $C_H1$ is modified such that the number of cysteine residues in the hinge region is altered, e.g. increased or decreased. This approach is described further in U.S. Pat. No. 5,677,425. The number of cysteine residues in the hinge region of $C_H1$ is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the $C_H2$-$C_H3$ domain interface region of the Fc-hinge fragment such that the antibody has impaired Staphylococcal protein A (SpA) binding relative to native Fc-hinge domain SpA binding. This approach is described in further detail in U.S. Pat. No. 6,165,745.

In another embodiment, the antibody is modified to increase its biological half life. Various approaches are possible. For example, one or more of the following mutations can be introduced: T252L, T254S, T256F, as described in U.S. Pat. No. 6,277,375. Alternatively, to increase the biological half life, the antibody can be altered within the $C_H1$ or $C_L$ region to contain a salvage receptor binding epitope taken from two loops of a $C_H2$ domain of an Fc region of an IgG, as described in U.S. Pat. Nos. 5,869,046 and 6,121,022.

In another embodiment, the antibody is produced as a UniBody as described in WO2007/059782 which is incorporated herein by reference in its entirety.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551.

In another example, one or more amino acid residues within amino acid positions 231 and 239 are altered to thereby alter the ability of the antibody to fix complement. This approach is described further in PCT Publication WO 94/29351.

In yet another example, the Fc region is modified to increase the ability of the antibody to mediate antibody dependent cellular cytotoxicity (ADCC) and/or to increase the affinity of the antibody for an Fcy receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγR1, FcγRII, FcγRIII and FcRn have been mapped and variants with improved binding have been described (see Shields, R. L. et al. (2001) *J. Biol. Chem.* 276:6591-6604). Specific mutations at positions 256, 290, 298, 333, 334 and 339 were shown to improve binding to FcγRIII Additionally, the following combination mutants were shown to improve FcγRIII binding: T256A/S298A, S298A/E333A, S298A/K224A and S298A/E333A/K334A. Further ADCC variants are described for example in WO2006/019447.

In yet another example, the Fc region is modified to increase the half-life of the antibody, generally by increasing binding to the FcRn receptor, as described for example in PCT/US2008/088053, U.S. Pat. Nos. 7,371,826, 7,670,600 and WO 97/34631. In another embodiment, the antibody is modified to increase its biological half life. Various approaches are possible. For example, one or more of the following mutations can be introduced: T252L, T254S, T256F, as described in U.S. Pat. No. 6,277,375 by Ward. Alternatively, to increase the biological half life, the antibody can be altered within the $C_H1$ or $C_L$ region to contain a salvage receptor binding epitope taken from two loops of a $C_H2$ domain of an Fc region of an IgG, as described in U.S. Pat. Nos. 5,869,046 and 6,121,022.

In still another embodiment, the glycosylation of an antibody is modified. For example, an aglycoslated antibody can be made (i.e. the antibody that lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al., and can be accomplished by removing the asparagine at position 297.

Additionally or alternatively, an antibody can be made that has an altered type of glycosylation, such as a hypofucosylated antibody having reduced amounts of fucosyl residues or an antibody having increased bisecting GlcNac structures. This is sometimes referred to in the art as an "engineered glycoform". Such altered glycosylation patterns have been demonstrated to increase the ADCC ability of antibodies. Such carbohydrate modifications can generally be accomplished in two ways; for example, in some embodiments, the antibody is expressed in a host cell with altered glycosylation machinery. Cells with altered glycosylation machinery have been described in the art and can be used as host cells in which to express recombinant antibodies of the invention to thereby produce an antibody with altered glycosylation. Reference is made to the POTELLIGENT® technology. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their carbohydrates. The Ms704, Ms705, and Ms709 FUT8$^{-/-}$ cell lines were created by the targeted disruption of the FUT8 gene in CHO/DG44 cells using two replacement vectors [see US Patent Publication No. 2004/0110704, U.S. Pat. No. 7,517,670 and Yamane-Ohnuki et al. (2004) *Biotechnol. Bioeng.* 87:614-22]. As another example, EP 1,176,195 by Hanai et al. describes a cell line with a functionally disrupted FUT8 gene, which encodes a fucosyl transferase, such that antibodies expressed in such a cell line exhibit hypofucosylation by reducing or eliminating the alpha 1,6 bond-related enzyme. Hanai et al. also describe cell lines which have a low enzyme activity for adding fucose to the N-acetylglucosamine that binds to the Fc region of the antibody or does not have the enzyme activity, for example the rat myeloma cell line YB2/0 (ATCC CRL 1662). Alternatively, engineered glycoforms, particularly afucosylation, can be done using small molecule inhibitors of glycosylation pathway enzymes [see, for example, Rothman et al. (1989) *Mol. Immunol.* 26(12):113-1123; Elbein (1991) *FASEB J.* 5:3055; PCT/US2009/042610 and U.S. Pat. No. 7,700,321]. PCT Publication WO 03/035835 describes a variant CHO cell line, Lec13 cells, with reduced ability to attach fucose to Asn(297)-linked carbohydrates, also resulting in hypofucosylation of antibodies expressed in that host cell [see also Shields, R. L. et al. (2002) *J. Biol. Chem.* 277:26733-26740]. PCT Publication WO 99/54342 describes cell lines engineered to express glycoprotein-modifying glycosyl transferases (e.g. beta(1,4)-N-acetylglucosaminyltransferase III (GnTIII)) such that antibodies expressed in the engineered cell lines exhibit increased bisecting GlcNac structures which results in increased ADCC activity of the antibodies [see also Umana et al. (1999) *Nat. Biotech.* 17:176-180].

Alternatively, the fucose residues of the antibody may be cleaved off using a fucosidase enzyme. For example, the fucosidase alpha-L-fucosidase removes fucosyl residues from antibodies [Tarentino, A. L. et al. (1975) *Biochem.* 14:5516-23].

Another modification of the antibodies herein that is contemplated by the invention is pegylation. An antibody can be pegylated to, for example, increase the biological (e.g. serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See, for example, EP 0154316 and EP 0401384.

In additional embodiments, for example in the use of the antibodies of the invention for diagnostic or detection purposes, the antibodies may comprise a label. By "labeled" herein is meant that a compound has at least one element, isotope or chemical compound attached to enable the detection of the compound. In general, labels fall into three classes: a) isotopic labels, which may be radioactive or heavy isotopes; b) magnetic, electrical, thermal; and c) colored or luminescent dyes; although labels include enzymes and particles such as magnetic particles as well. Preferred labels include, but are not limited to, fluorescent lanthanide complexes (including those of Europium and Terbium), and fluorescent labels including, but not limited to, quantum dots, fluorescein, rhodamine, tetramethylrhodamine, eosin, erythrosin, coumarin, methyl-coumarins, pyrene, Malacite green, stilbene, Lucifer Yellow, Cascade Blue, Texas Red, the Alexa dyes, the Cy dyes, and others described in the 6th Edition of the Molecular Probes Handbook by Richard P. Haugland, hereby expressly incorporated by reference.

Linkers

The present invention provides antibody-partner conjugates where the antibody is linked to the partner through a chemical linker. In some embodiments, the linker is a peptidyl linker, other linkers include hydrazine and disulfide linkers. In addition to the linkers as being attached to the partner, the present disclosure also provides cleavable linker arms that are appropriate for attachment to essentially any molecular species. The linker arm aspect of the invention is exemplified herein by reference to their attachment to a therapeutic moiety. It will, however, be readily apparent to those of skill in the art that the linkers can be attached to diverse species including, but not limited to, diagnostic agents, analytical agents, biomolecules, targeting agents, detectable labels and the like.

The use of peptidyl and other linkers in antibody-partner conjugates is described in U.S. Provisional Patent Application Ser. Nos. 60/295,196; 60/295,259; 60/295,342; 60/304,908; 60/572,667; 60/661,174; 60/669,871; 60/720,499; 60/730,804; and 60/735,657 and U.S. patent application Ser. Nos. 10/160,972; 10/161,234; 11/134,685; 11/134,826; and 11/398,854 and U.S. Pat. No. 6,989,452 and PCT Patent Application No. PCT/US2006/37793, all of which are incorporated herein by reference. Additional linkers are described in U.S. Pat. No. 6,214,345, US Patent Application 2003/0096743 and US Patent Application 2003/0130189, de Groot et al, J. Med. Chem. 42, 5277 (1999); de Groot et al. J. Org. Chem. 43, 3093 (2000); de Groot et al., J. Med. Chem. 66, 8815, (2001); WO 02/083180; Carl et al., J. Med. Chem. Lett. 24, 479, (1981); Dubowchik et al., Bioorg & Med. Chem. Lett. 8, 3347 (1998); and U.S. Provisional Patent Application Ser. No. 60/891,028.

In one aspect, the present disclosure relates to linkers that are useful to attach targeting groups to therapeutic agents and markers. In another aspect, this disclosure provides linkers that impart stability to compounds, reduce their in vivo toxicity, or otherwise favorably affect their pharmacokinetics, bioavailability and/or pharmacodynamics. It is generally preferred that in such embodiments, the linker is cleaved, releasing the active drug, once the drug is delivered to its site of action. Thus, in one embodiment, the linkers of the present invention are traceless, such that once removed from the therapeutic agent or marker (such as during activation), no trace of the linker's presence remains. In another embodiment, the linkers are characterized by their ability to be cleaved at a site in or near the target cell such as at the site of therapeutic action or marker activity. Such cleavage can be enzymatic in nature. This feature aids in reducing systemic activation of the therapeutic agent or marker, reducing toxicity and systemic side effects. Preferred cleavable groups for enzymatic cleavage include peptide bonds, ester linkages, and disulfide linkages. In other embodiments, the linkers are sensitive to pH and are cleaved through changes in pH.

An aspect of the current disclosure is the ability to control the speed with which the linkers cleave. Often a linker that cleaves quickly is desired. In some embodiments, however, a linker that cleaves more slowly may be preferred. For example, in a sustained release formulation or in a formulation with both a quick release and a slow release component, it may be useful to provide a linker which cleaves more slowly. WO 02/096910 provides several specific ligand-drug complexes having a hydrazine linker. However, there is no way to "tune" the linker composition dependent upon the rate of cyclization required, and the particular compounds described cleave the ligand from the drug at a slower rate than is preferred for many drug-linker conjugates. In contrast, the hydrazine linkers of the current invention provide for a range of cyclization rates, from very fast to very slow, thereby allowing for the selection of a particular hydrazine linker based on the desired rate of cyclization.

For example, very fast cyclization can be achieved with hydrazine linkers that produce a single 5-membered ring upon cleavage. Preferred cyclization rates for targeted delivery of a cytotoxic agent to cells are achieved using hydrazine linkers that produce, upon cleavage, either two 5-membered rings or a single 6-membered ring resulting from a linker having two methyls at the geminal position. The gem-dimethyl effect has been shown to accelerate the rate of the cyclization reaction as compared to a single 6-membered ring without the two methyls at the geminal position. This results from the strain being relieved in the ring. Sometimes, however, substitutents may slow down the reaction instead of making it faster. Often the reasons for the retardation can be traced to steric hindrance. For example, the gem dimethyl substitution allows for a much faster cyclization reaction to occur compared to when the geminal carbon is a CH2.

It is important to note, however, that in some embodiments, a linker that cleaves more slowly may be preferred. For example, in a sustained release formulation or in a formulation with both a quick release and a slow release component, it may be useful to provide a linker which cleaves more slowly. In certain embodiments, a slow rate of cyclization is achieved using a hydrazine linker that produces, upon cleavage, either a single 6-membered ring, without the gem-dimethyl substitution, or a single 7-membered ring. The linkers also serve to stabilize the therapeutic agent or marker against degradation while in circulation. This feature provides a significant benefit since such stabilization results in prolonging the circulation half-life of the attached agent or marker. The linker also serves to attenuate the activity of the attached agent or marker so that the conjugate is relatively benign while in circulation and has the desired effect, for example is toxic, after activation at the desired site of action. For therapeutic agent conjugates, this feature of the linker serves to improve the therapeutic index of the agent.

The stabilizing groups are preferably selected to limit clearance and metabolism of the therapeutic agent or marker by enzymes that may be present in blood or non-target tissue and are further selected to limit transport of the agent or marker into the cells. The stabilizing groups serve to block degradation of the agent or marker and may also act in providing other physical characteristics of the agent or marker. The stabilizing group may also improve the agent or marker's stability during storage in either a formulated or non-formulated form.

Ideally, the stabilizing group is useful to stabilize a therapeutic agent or marker if it serves to protect the agent or marker from degradation when tested by storage of the agent or marker in human blood at 37° C. for 2 hours and results in less than 20%, preferably less than 10%, more preferably less than 5% and even more preferably less than 2%, cleavage of the agent or marker by the enzymes present in the human blood under the given assay conditions. The present invention also relates to conjugates containing these linkers. More particularly, the invention relates to the use of prodrugs that may be used for the treatment of disease, especially for cancer chemotherapy. Specifically, use of the linkers described herein provide for prodrugs that display a high specificity of action, a reduced toxicity, and an improved stability in blood relative to prodrugs of similar structure. The linkers of the present disclosure as described herein may be present at a variety of positions within the partner molecule.

Thus, there is provided a linker that may contain any of a variety of groups as part of its chain that will cleave in vivo, e.g. in the blood stream, at a rate which is enhanced relative to that of constructs that lack such groups. Also provided are conjugates of the linker arms with therapeutic and diagnostic agents. The linkers are useful to form prodrug analogs of therapeutic agents and to reversibly link a therapeutic or diagnostic agent to a targeting agent, a detectable label, or a solid support. The linkers may be incorporated into complexes that include cytotoxins.

The attachment of a prodrug to an antibody may give additional safety advantages over conventional antibody conjugates of cytotoxic drugs. Activation of a prodrug may be achieved by an esterase, both within tumor cells and in several normal tissues, including plasma. The level of relevant esterase activity in humans has been shown to be very similar to that observed in rats and non-human primates, although less than that observed in mice. Activation of a prodrug may also be achieved by cleavage by glucuronidase. In addition to the cleavable peptide, hydrazine, or disulfide group, one or more self-immolative linker groups are optionally introduced between the cytotoxin and the targeting agent. These linker groups may also be described as spacer groups and contain at least two reactive functional groups. Typically, one chemical functionality of the spacer group bonds to a chemical functionality of the therapeutic agent, e.g. cytotoxin, while the other chemical functionality of the spacer group is used to bond to a chemical functionality of the targeting agent or the cleavable linker. Examples of chemical functionalities of spacer groups include hydroxy, mercapto, carbonyl, carboxy, amino, ketone, and mercapto groups.

The self-immolative linkers are generally a substituted or unsubstituted alkyl, substituted or unsubstituted aryl, substituted or unsubstituted heteroaryl or substituted or unsubstituted heteroalkyl group. In one embodiment, the alkyl or aryl groups may comprise between 1 and 20 carbon atoms. They may also comprise a polyethylene glycol moiety.

Exemplary spacer groups include, for example, 6-aminohexanol, 6-mercaptohexanol, 10-hydroxydecanoic acid, glycine and other amino acids, 1,6-hexanediol, β-alanine, 2-ammoethanol, cysteamine (2-aminoethanethiol), 5-aminopentanoic acid, 6-aminohexanoic acid, 3-maleimidobenzoic acid, phthalide, α-substituted phthalies, the carbonyl group, animal esters, nucleic acids, peptides and the like.

The spacer can serve to introduce additional molecular mass and chemical functionality into the cytotoxin-targeting agent complex. Generally, the additional mass and functionality will affect the serum half-life and other properties of the complex. Thus, through careful selection of spacer groups, cytotoxin complexes with a range of serum half-lives can be produced.

When multiple spacers are present, either identical or different spacers may be used.

Additional linker moiety may be used that preferably imparts increased solubility or decreased aggregation properties to conjugates utilizing a linker that contains the moiety or modifies the hydrolysis rate of the conjugate, such linkers do not have to be self immolative. In one embodiment, the linking moiety is substituted alkyl, unsubstituted alkyl, substituted aryl, unsubstituted aryl, substituted heteroalkyl, or unsubstituted heteroalkyl, any of which may be straight, branched, or cyclic. The substitutions may be, for example, a lower ($C_1$-$C_6$) alkyl, alkoxy, aklylthio, alkylamino, or dialkylamino. In certain embodiments, linkers comprise a non-cyclic moiety. In another embodiment, linkers comprise any positively or negatively charged amino acid polymer, such as polylysine or polyargenine. Linkers can comprise a polymer such as a polyethylene glycol moiety. Additionally the linker can comprise, for example, both a polymer component and a small chemical moiety. In a preferred embodiment, such linkers comprise a polyethylene glycol (PEG) moiety.

The PEG portion may be between 1 and 50 units long. Preferably, the PEG will have 1-12 repeat units, more preferably 3-12 repeat units, more preferably 2-6 repeat units, or even more preferably 3-5 repeat units and most preferably 4 repeat units. A linker may consist solely of the PEG moiety, or it may also contain an additional substituted or unsubstituted alkyl or heteroalkyl. It is useful to combine PEG as part of the moiety to enhance the water solubility of the complex. Additionally, the PEG moiety reduces the degree of aggregation that may occur during the conjugation of the drug to the antibody.

For further discussion of types of cytotoxins, linkers and other methods for conjugating therapeutic agents to antibodies, see also PCT Publication WO 2007/059404 to Gangwar et al. and entitled "Cytotoxic Compounds And Conjugates," Saito, G. et al. (2003) Adv. Drug Deliv. Rev. 55:199-215; Trail, P. A. et al. (2003) Cancer Immunol. Immunother. 52:328-337; Payne, G. (2003) Cancer Cell 3:207-212; Allen, T. M. (2002) Nat. Rev. Cancer 2:750-763; Pastan, I. and Kreitman, R. J. (2002) Curr. Opin. Investig. Drugs 3:1089-1091; Senter, P. D. and Springer, CJ. (2001) Adv. Drag Deliv. Rev. 53:247-264, each of which is hereby incorporated by reference in their entirety.

Partner Molecules

The present invention includes an antibody conjugated to a partner molecule, such as a cytotoxin, a drug (e.g. an immunosuppressant) or a radiotoxin. Such conjugates are also referred to herein as "immunoconjugates." Immunoconjugates that include one or more cytotoxins are referred to as "immunotoxins." A cytotoxin or cytotoxic agent includes any agent that is detrimental to (e.g. kills) cells.

Examples of partner molecules of the present disclosure include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Examples of partner molecules also include, for example, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, and anthramycin (AMC)), and anti-mitotic agents (e.g. vincristine and vinblastine).

Other preferred examples of partner molecules that can be conjugated to an antibody of the invention include duocarmycins, calicheamicins, maytansines and auristatins, and derivatives thereof. An example of a calicheamicin antibody conjugate is commercially available (Mylotarg®; American Home Products).

Preferred examples of partner molecule are CC-1065 and the duocarmycins. CC-1065 was first isolated from *Streptomyces zelensis* in 1981 by the Upjohn Company (Hanka et al, J. Antibiot. 31: 1211 (1978); Martin et al., J. Antibiot. 33: 902 (1980); Martin et al., J. Antibiot. 34: 1119 (1981)) and was found to have potent antitumor and antimicrobial activity both in vitro and in experimental animals (Li et al., Cancer Res. 42: 999 (1982)). CC-1065 binds to double-stranded B-DNA within the minor groove (Swenson et al., Cancer Res. 42: 2821 (1982)) with the sequence preference of 5'-d(A/GNTTA)-3' and 5'-d(AAAAA)-3' and alkylates the N3 position of the 3'-adenine by its CPI left-hand unit present in the molecule (Hurley et al., Science 226: 843 (1984)).

Despite its potent and broad antitumor activity, CC-1065 cannot be used in humans because it causes delayed death in experimental animals. Many analogues and derivatives of CC-1065 and the duocarmycins are known in the art. The research into the structure, synthesis and properties of many of the compounds has been reviewed. See, for example, Boger et al., Angew. Chem. Int. Ed. Engl. 35: 1438 (1996); and Boger et al., Chem. Rev. 97: 787 (1997). A group at Kyowa Hakko Kogya Co., Ltd. has prepared a number of CC-1065 derivatives. See, for example, U.S. Pat. Nos. 5,101,038; 5,641,780; 5,187,186; 5,070,092; 5,703,080; 5,070,092; 5,641,780; 5,101,038; and 5,084,468; and published PCT application, WO 96/10405 and published European application 0 537 575 A1. The Upjohn Company (Pharmacia Upjohn) has also been active in preparing derivatives of CC-1065. See, for example, U.S. Pat. Nos. 5,739,350; 4,978,757, 5,332, 837 and 4,912,227.

Antibody Physical Properties

The antibodies of the present invention may be further characterized by the various physical properties of the anti-BST1 antibodies. Various assays may be used to detect and/or differentiate different classes of antibodies based on these physical properties.

In some embodiments, antibodies of the present invention may contain one or more glycosylation sites in either the light or heavy chain variable region. The presence of one or more glycosylation sites in the variable region may result in increased immunogenicity of the antibody or an alteration of the pK of the antibody due to altered antigen binding [Marshall et al (1972) *Annu Rev Biochem* 41:673-702; Gala F A and Morrison S L (2004) *J Immunol* 172:5489-94; Wallick et al (1988) *J Exp Med* 168:1099-109; Spiro R G (2002) *Glycobiology* 12:43R-56R; Parekh et al (1985) *Nature* 316:452-7; Mimura et al. (2000) *Mol Immunol* 37:697-706]. Glycosylation has been known to occur at motifs containing an N—X-S/T sequence. Variable region glycosylation may be tested using a glycoblot assay, which cleaves the antibody to produce a Fab, and then tests for glycosylation using an assay that measures periodate oxidation and Schiff base formation. Alternatively, variable region glycosylation may be tested using Dionex light chromatography (Dionex-LC), which cleaves saccharides from a Fab into monosaccharides and analyzes the individual saccharide content. In some instances, it is preferred to have an anti-BST1 antibody that does not contain variable region glycosylation. This can be achieved either by selecting antibodies that do not contain the glycosylation motif in the variable region or by mutating residues within the glycosylation motif using standard techniques well known in the art.

In a preferred embodiment, the antibodies of the present invention do not contain asparagine isomerism sites. A deamidation or isoaspartic acid effect may occur on N-G or D-G sequences, respectively. The deamidation or isoaspartic acid effect results in the creation of isoaspartic acid which decreases the stability of an antibody by creating a kinked structure off a side chain carboxy terminus rather than the main chain. The creation of isoaspartic acid can be measured using an iso-quant assay, which uses a reverse-phase HPLC to test for isoaspartic acid.

Each antibody will have a unique isoelectric point (pI), but generally antibodies will fall in the pH range of between 6 and 9.5. The pI for an IgG1 antibody typically falls within the pH range of 7-9.5 and the pI for an IgG4 antibody typically falls within the pH range of 6-8. Antibodies may have a pI that is outside this range. Although the effects are generally unknown, there is speculation that antibodies with a pI outside the normal range may have some unfolding and instability under in vivo conditions. The isoelectric point may be tested using a capillary isoelectric focusing assay, which creates a pH gradient and may utilize laser focusing for increased accuracy [Janini et al (2002) *Electrophoresis* 23:1605-11; Ma et al. (2001) *Chromatographia* 53:S75-89; Hunt et al (1998) *J Chromatogr A* 800:355-67]. In some instances, it is preferred to have an anti-BST1 antibody that contains a pI value that falls in the normal range. This can be achieved either by selecting antibodies with a pI in the normal range, or by mutating charged surface residues using standard techniques well known in the art.

Each antibody will have a melting temperature that is indicative of thermal stability [Krishnamurthy R and Manning M C (2002) *Curr Pharm Biotechnol* 3:361-71]. A higher thermal stability indicates greater overall antibody stability in vivo. The melting point of an antibody may be measured using techniques such as differential scanning calorimetry [Chen et al. (2003) *Pharm Res* 20:1952-60; Ghirlando et al. (1999) *Immunol Lett* 68:47-52]. $T_{M1}$ indicates the temperature of the initial unfolding of the antibody. $T_{M2}$ indicates the temperature of complete unfolding of the antibody. Generally, it is preferred that the $T_{M1}$ of an antibody of the present invention is greater than 60° C., preferably greater than 65° C., even more preferably greater than 70° C. Alternatively, the thermal stability of an antibody may be measure using circular dichroism [Murray et al. (2002) *J. Chromatogr Sci* 40:343-9].

In a preferred embodiment, antibodies are selected that do not rapidly degrade. Fragmentation of an anti-BST1 antibody may be measured using capillary electrophoresis (CE) and MALDI-MS, as is well understood in the art [Alexander A J and Hughes D E (1995) *Anal. Chem.* 67:3626-32].

In another preferred embodiment, antibodies are selected that have minimal aggregation effects. Aggregation may lead to triggering of an unwanted immune response and/or altered or unfavorable pharmacokinetic properties. Generally, antibodies are acceptable with aggregation of 25% or less, preferably 20% or less, even more preferably 15% or less, even more preferably 10% or less and even more preferably 5% or less. Aggregation may be measured by several techniques well known in the art, including size-exclusion column (SEC) high performance liquid chromatography (HPLC), and light scattering to identify monomers, dimers, trimers or multimers.

Methods of Engineering Antibodies

As discussed above, the anti-BST1 antibodies having $V_H$ and $V_K$ sequences disclosed herein can be used to create new anti-BST1 antibodies by modifying the $V_H$ and/or $V_K$ sequences, or the constant region(s) attached thereto. Thus, in another aspect of the invention, the structural features of an anti-BST1 antibody of the invention, e.g. BST1_A2, BST1_A1 or BST1_A3, are used to create structurally related anti-BST1 antibodies that retain at least one functional property of the antibodies of the invention, such as binding to the human BST1. For example, one or more CDR regions of BST1_A2, BST1_A1 or BST1_A3, or mutations thereof, can be combined recombinantly with known framework regions and/or other CDRs to create additional, recombinantly-engineered, anti-BST1 antibodies of the invention, as discussed above. Other types of modifications include those described in the previous section. The starting material for the engineering method is one or more of the $V_H$ and/or $V_K$ sequences provided herein, or one or more CDR regions thereof. To create the engineered antibody, it is not necessary to actually prepare (i.e. express as a protein) an antibody having one or more of the $V_H$ and/or $V_K$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the invention provides a method for preparing an anti-BST1 antibody comprising: providing: (i) a heavy chain variable region antibody sequence comprising a CDR1 sequence selected from the group consisting of SEQ ID NOs: 10, 9 and 56, a CDR2 sequence selected from the group consisting of SEQ ID NOs: 12 or 51, 11 and 57, and/or a CDR3 sequence selected from the group consisting of SEQ ID NOs: 14, 13 and 58; and/or (ii) a light chain variable region antibody sequence comprising a CDR1 sequence selected from the group consisting of SEQ ID NOs: 16, 15 and 59, a CDR2 sequence selected from the group consisting of SEQ ID NOs: 18, 17 and 60 and/or a CDR3 sequence selected from the group consisting of SEQ ID NOs: 20, 19 and 61, altering at least one amino acid residue within the heavy chain variable region antibody sequence and/or the light chain variable region antibody sequence to create at least one altered antibody sequence; and expressing the altered antibody sequence as a protein.

Standard molecular biology techniques can be used to prepare and express the altered antibody sequence.

Preferably, the antibody encoded by the altered antibody sequence(s) is one that retains one, some or all of the functional properties of the anti-BST1 antibodies described herein, which functional properties include, but are not limited to: (a) binds to the human BST1 with a $K_D$ of $1\times10^{-7}$ M or less; (b) binds to human CHO cells transfected with the BST1.

The functional properties of the altered antibodies can be assessed using standard assays available in the art and/or described herein, such as those set forth in the Examples (e.g. flow cytometry, binding assays).

In certain embodiments of the methods of engineering antibodies of the invention, mutations can be introduced randomly or selectively along all or part of an anti-BST1 antibody coding sequence and the resulting modified anti-BST1 antibodies can be screened for binding activity and/or other functional properties as described herein. Mutational methods have been described in the art. For example, PCT Publication WO 02/092780 describes methods for creating and screening antibody mutations using saturation mutagenesis, synthetic ligation assembly, or a combination thereof. Alternatively, PCT Publication WO 03/074679 describes methods of using computational screening methods to optimize physiochemical properties of antibodies.

Nucleic Acid Molecules Encoding Antibodies of the Invention

Another aspect of the invention pertains to nucleic acid molecules that encode the antibodies of the invention. The nucleic acids may be present in whole cells, in a cell lysate, or in a partially purified or substantially pure form. A nucleic acid is "isolated" or "rendered substantially pure" when purified away from other cellular components or other contaminants, e.g. other cellular nucleic acids or proteins, by standard techniques, including alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, N. Y. A nucleic acid of the invention can be, for example, DNA or RNA and may or may not contain intronic sequences. In a preferred embodiment, the nucleic acid is a cDNA molecule.

Nucleic acids of the invention can be obtained using standard molecular biology techniques. For antibodies expressed by hybridomas, cDNAs encoding the light and heavy chains of the antibody made by the hybridoma can be obtained by standard PCR amplification or cDNA cloning techniques. For antibodies obtained from an immunoglobulin gene library (e.g. using phage display techniques), nucleic acids encoding the antibody can be recovered from the library.

Preferred nucleic acids molecules of the invention are those encoding the $V_H$ and $V_K$ sequences of the BST1_A2, BST1_A1 or BST1_A3 monoclonal antibodies. DNA sequences encoding the $V_H$ sequences of BST1_A2, BST1_A1 or BST1_A3 are shown in SEQ ID NOs: 6, 5 and 54, respectively. DNA sequences encoding the $V_K$ sequences of BST1_A2, BST1_A1 or BST1_A3 are shown in SEQ ID NOs: 8, 7 and 55, respectively.

Other preferred nucleic acids of the invention are nucleic acids having at least 80% sequence identity, such as at least 85%, at least 90%, at least 95%, at least 98% or at least 99% sequence identity, with one of the sequences shown in SEQ ID NOs: 6, 5, 8, 7, 54 and 55, which nucleic acids encode an antibody of the invention, or an antigen-binding portion thereof.

The percent identity between two nucleic acid sequences is the number of positions in the sequence in which the nucleotide is identical, taking into account the number of gaps and the length of each gap, which need to be introduced for optimal alignment of the two sequences. The comparison of sequences and determination of percent identity between two sequences can be accomplished using a mathematical algorithm, such as the algorithm of Meyers and Miller or the XBLAST program of Altschul described above.

Still further, preferred nucleic acids of the invention comprise one or more CDR-encoding portions of the nucleic acid sequences shown in SEQ ID NOs: 6, 5, 8, 7, 54 and 55. In this embodiment, the nucleic acid may encode the heavy and light chain CDR1, CDR2 and/or CDR3 sequence of BST1_A2, BST1_A1 or BST1_A3.

Nucleic acids which have at least 80%, such as at least 85%, at least 90%, at least 95%, at least 98% or at least 99% sequence identity, with such a CDR-encoding portion of SEQ ID NOs: 6, 5, 8, 7, 54 and 55 ($V_H$ and $V_K$ segs) are also preferred nucleic acids of the invention. Such nucleic acids may differ from the corresponding portion of SEQ ID NOs: 6, 5, 8, 7, 54 and 55 in a non-CDR coding region and/or in a CDR-coding region. Where the difference is in a CDR-coding region, the nucleic acid CDR region encoded by the nucleic acid typically comprises one or more conservative sequence modifications as defined herein compared to the corresponding CDR sequence of BST1_A2, BST1_A1 or BST1_A3.

Once DNA fragments encoding $V_H$ and $V_K$ segments are obtained, these DNA fragments can be further manipulated by standard recombinant DNA techniques, for example, to convert the variable region genes to full-length antibody chain genes, to Fab fragment genes, or to a scFv gene. In these manipulations, a $V_K$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($C_H1$, $C_H2$ and $C_H3$). The sequences of murine heavy chain constant region genes are known in the art [see e.g. Kabat, E. A., et al. (1991) Sequences of Proteins of Immunological Interest, Fifth Edition, US Department of Health and Human Services, NIH Publication No. 91-3242] and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain $C_H1$ constant region.

The isolated DNA encoding the VL/VK region can be converted to a full-length light chain gene (as well as a Fab light chain gene) by operatively linking the $V_L$-encoding DNA to another DNA molecule encoding the light chain constant region, $C_L$. The sequences of murine light chain constant region genes are known in the art [see, e.g. Kabat, E. A., et al. (1991) Sequences of Proteins of Immunological Interest, Fifth Edition, US Department of Health and Human Services, NIH Publication No. 91-3242] and DNA fragments encompassing these regions can be obtained by standard PCR amplification. In preferred embodiments, the light chain constant region can be a kappa or lambda constant region.

To create a scFv gene, the $V_H$- and $V_L/V_K$-encoding DNA fragments are operatively linked to another fragment encoding a flexible linker, e.g. encoding the amino acid sequence $(Gly_4\text{-}Ser)_3$, such that the $V_H$ and $V_L/V_K$ sequences can be expressed as a contiguous single-chain protein, with the $V_L/V_K$ and $V_H$ regions joined by the flexible linker [see e.g. Bird et al. (1988) *Science* 242:423-426; Huston et al. (1988) *Proc. Natl. Acad. Sci. USA* 85:5879-5883; McCafferty et al., (1990) *Nature* 348:552-554].

Production of Monoclonal Antibodies

According to the invention the BST1 or a fragment or derivative thereof may be used as an immunogen to generate antibodies which immunospecifically bind such an immunogen. Such immunogens can be isolated by any convenient means. One skilled in the art will recognize that many procedures are available for the production of antibodies, for example, as described in Antibodies, A Laboratory Manual, Ed Harlow and David Lane, Cold Spring Harbor Laboratory (1988), Cold Spring Harbor, N.Y. One skilled in the art will also appreciate that binding fragments or Fab fragments which mimic antibodies can also be prepared from genetic information by various procedures [Antibody Engineering: A Practical Approach (Borrebaeck, C., ed.), 1995, Oxford University Press, Oxford; *J. Immunol.* 149, 3914-3920 (1992)].

In one embodiment of the invention, antibodies to a specific domain of the BST1 are produced. In a specific embodiment, hydrophilic fragments of the BST1 are used as immunogens for antibody production.

In the production of antibodies, screening for the desired antibody can be accomplished by techniques known in the art, e.g. ELISA (enzyme-linked immunosorbent assay). For example, to select antibodies which recognize a specific domain of the BST1, one may assay generated hybridomas for a product which binds to an BST1 fragment containing such a domain. For selection of an antibody that specifically binds a first BST1 homolog but which does not specifically bind to (or binds less avidly to) a second BST1 homolog, one can select on the basis of positive binding to the first BST1 homolog and a lack of binding to (or reduced binding to) the second BST1 homolog. Similarly, for selection of an antibody that specifically binds the BST1 but which does not specifically bind to (or binds less avidly to) a different isoform of the same protein (such as a different glycoform having the same core peptide as the BST1), one can select on the basis of positive binding to the BST1 and a lack of binding to (or reduced binding to) the different isoform (e.g. a different glycoform). Thus, the present invention provides an antibody (such as a monoclonal antibody) that binds with greater affinity (for example at least 2-fold, such as at least 5-fold, particularly at least 10-fold greater affinity) to the BST1 than to a different isoform or isoforms (e.g. glycoforms) of the BST1.

Polyclonal antibodies which may be used in the methods of the invention are heterogeneous populations of antibody molecules derived from the sera of immunized animals. Unfractionated immune serum can also be used. Various procedures known in the art may be used for the production of polyclonal antibodies to the BST1, a fragment of the BST1, an BST1-related polypeptide, or a fragment of an BST1-related polypeptide. For example, one way is to purify polypeptides of interest or to synthesize the polypeptides of interest using, e.g. solid phase peptide synthesis methods well known in the art. See, e.g. Guide to Protein Purification, Murray P. Deutcher, ed., *Meth. Enzymol.* Vol 182 (1990); Solid Phase Peptide Synthesis, Greg B. Fields ed., *Meth. Enzymol.* Vol 289 (1997); Kiso et al., *Chem. Pharm. Bull.* (Tokyo) 38: 1192-99, 1990; Mostafavi et al., *Biomed. Pept. Proteins Nucleic Acids* 1: 255-60, 1995; Fujiwara et al., *Chem. Pharm. Bull.* (Tokyo) 44: 1326-31, 1996. The selected polypeptides may then be used to immunize by injection various host animals, including but not limited to rabbits, mice, rats, etc., to generate polyclonal or monoclonal antibodies. Various adjuvants (i.e. immunostimulants) may be used to enhance the immunological response, depending on the host species, including, but not limited to, complete or incomplete Freund's adjuvant, a mineral gel such as aluminum hydroxide, surface active substance such as lysolecithin, pluronic polyol, a polyanion, a peptide, an oil emulsion, keyhole limpet hemocyanin, dinitrophenol, and an adjuvant such as BCG (bacille Calmette-Guerin) or *Corynebacterium parvum*. Additional adjuvants are also well known in the art.

For preparation of monoclonal antibodies (mAbs) directed toward the BST1, any technique which provides for the production of antibody molecules by continuous cell lines in culture may be used. For example, the hybridoma technique originally developed by Kohler and Milstein (1975, *Nature* 256:495-497), as well as the trioma technique, the human B-cell hybridoma technique [Kozbor et al. (1983) *Immunology Today* 4:72], and the EBV-hybridoma technique to produce human monoclonal antibodies [Cole et al. (1985) in *Monoclonal Antibodies and Cancer Therapy*, Alan R. Liss, Inc., pp. 77-96]. Such antibodies may be of any immunoglobulin class including IgG, IgM, IgE, IgA, IgD and any subclass thereof. The hybridoma producing the monoclonal antibodies may be cultivated in vitro or in vivo. In an additional embodiment of the invention, monoclonal antibodies can be produced in germ-free animals utilizing known technology (PCT/US90/02545, incorporated herein by reference).

The preferred animal system for preparing hybridomas is the murine system. Hybridoma production in the mouse is a very well-established procedure. Immunization protocols and techniques for isolation of immunized splenocytes for fusion are known in the art. Fusion partners (e.g. murine myeloma cells) and fusion procedures are also known.

The monoclonal antibodies include but are not limited to human monoclonal antibodies and chimeric monoclonal antibodies (e.g. human-mouse chimeras).

Chimeric or humanized antibodies of the present invention can be prepared based on the sequence of a non-human monoclonal antibody prepared as described above. DNA encoding the heavy and light chain immunoglobulins can be obtained from the non-human hybridoma of interest and engineered to contain non-murine (e.g. human) immunoglobulin sequences using standard molecular biology techniques. For example, to create a chimeric antibody, murine variable regions can be linked to human constant regions using methods known in the art (see e.g. U.S. Pat. No. 4,816,567 to Cabilly et al.). To create a humanized antibody, murine CDR regions can be inserted into a human framework using methods known in the art (see e.g. U.S. Pat. No. 5,225,539 to Winter, and U.S. Pat. Nos. 5,530,101; 5,585,089; 5,693,762 and 6,180,370 to Queen et al.).

Completely human antibodies can be produced using transgenic or transchromosomic mice which are incapable of expressing endogenous immunoglobulin heavy and light chain genes, but which can express human heavy and light chain genes. The transgenic mice are immunized in the normal fashion with a selected antigen, e.g. all or a portion of the BST1. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. These transgenic and transchromosomic mice include mice of the HuMAb Mouse® (Medarex®, Inc.) and KM Mouse® strains. The HuMAb Mouse® strain (Medarex®, Inc.) is described in Lonberg and Huszar (1995, *Int. Rev. Immunol.* 13:65-93). For a detailed discussion of this technology for producing human antibodies and human monoclonal antibodies and protocols for producing such antibodies, see, e.g. U.S. Pat. Nos. 5,625,126; 5,633,425; 5,569,825; 5,661,016; and 5,545,806. The KM Mouse® strain refers to a mouse that carries a human heavy chain transgene and a human light chain transchromosome and is described in detail in PCT Publication WO 02/43478 to Ishida et al.

Still further, alternative transgenic animal systems expressing human immunoglobulin genes are available in the art and can be used to raise anti-BST1 antibodies of the invention. For example, an alternative transgenic system referred to as the Xenomouse (Amgen, Inc.) can be used; such mice are described in, for example, U.S. Pat. Nos. 5,939,598; 6,075,181; 6,114,598; 6,150,584 and 6,162,963 to Kucherlapati et al.

Completely human antibodies which recognize a selected epitope can be generated using a technique referred to as "guided selection". In this approach a selected non-human monoclonal antibody, e.g. a mouse antibody, is used to guide the selection of a completely human antibody recognizing the same epitope [Jespers et al. (1994) *Biotechnology* 12:899-903].

Moreover, alternative transchromosomic animal systems expressing human immunoglobulin genes are available in the art and can be used to raise anti-BST1 antibodies. For example, mice carrying both a human heavy chain transchromosome and a human light chain tranchromosome, referred to as "TC mice" can be used; such mice are described in Tomizuka et al. (2000) *Proc. Natl. Acad. Sci. USA* 97:722-727. Furthermore, cows carrying human heavy and light chain transchromosomes have been described in the art [Kuroiwa et al. (2002) *Nature Biotechnology* 20:889-894] and PCT publication No. WO2002/092812 and can be used to raise anti-BST1 antibodies.

Human monoclonal antibodies of the invention can also be prepared using SCID mice into which human immune cells have been reconstituted such that a human antibody response can be generated upon immunization. Such mice are described in, for example, U.S. Pat. Nos. 5,476,994 and 3,698,767.

The antibodies of the present invention can be generated by the use of phage display technology to produce and screen libraries of polypeptides for binding to a selected target [see, e.g. Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698]. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phages can be determined from their respective genomes. Using these methods a polypeptide identified as having a binding affinity for a desired target can then be synthesized in bulk by conventional means. See, e.g. U.S. Pat. No. 6,057,098, which is hereby incorporated in its entirety, including all tables, figures, and claims. In particular, such phage can be utilized to display antigen binding domains expressed from a repertoire or combinatorial antibody library (e.g. human or murine). Phage expressing an antigen binding domain that binds the antigen of interest can be selected or identified with antigen, e.g. using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Phage display methods that can be used to make the antibodies of the present invention include those disclosed in Brinkman et al. (1995) *J. Immunol. Methods* 182:41-50; Ames et al. (1995) *J. Immunol. Methods* 184:177-186; Kettleborough et al., *Eur. J. Immunol.* 24:952-958 (1994); Persic et al. (1997) *Gene* 187 9-18; Burton et al. (1994) *Advances in Immunology* 57:191-280; PCT Application No. PCT/GB91/01134; PCT Publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g. as described in detail below. For example, techniques to recombinantly produce Fab, Fab' and F(ab')2 fragments can also be employed using methods known in the art such as those disclosed in PCT publication WO 92/22324; Mullinax et al. (1992) *BioTechniques* 12(6):864-869; and Sawai et al. (1995) *AJRI* 34:26-34; and Better et al. (1988) *Science* 240:1041-1043 (said references incorporated by reference in their entireties).

Examples of techniques which can be used to produce single-chain Fvs and antibodies include those described in U.S. Pat. Nos. 4,946,778 and 5,258,498; Huston et al. (1991), *Methods in Enzymology* 203:46-88; Shu et al. (1993) *PNAS* 90:7995-7999; and Skerra et al. (1988) *Science* 240:1038-1040.

The invention provides functionally active fragments, derivatives or analogs of the anti-BST1 immunoglobulin molecules. Functionally active means that the fragment, derivative or analog is able to elicit anti-anti-idiotype antibodies (i.e. tertiary antibodies) that recognize the same antigen that is recognized by the antibody from which the fragment, derivative or analog is derived. Specifically, in a particular embodiment the antigenicity of the idiotype of the immunoglobulin molecule may be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art.

The present invention provides antibody fragments such as, but not limited to, F(ab')2 fragments and Fab fragments. Antibody fragments which recognize specific epitopes may be generated by known techniques. F(ab')2 fragments consist of the variable region, the light chain constant region and the $C_H1$ domain of the heavy chain and are generated by pepsin digestion of the antibody molecule. Fab fragments are generated by reducing the disulfide bridges of the $F(ab')_2$ fragments. The invention also provides heavy chain and light chain dimers of the antibodies of the invention, or any minimal fragment thereof such as Fvs or single chain antibodies (SCAs) [e.g. as described in U.S. Pat. No. 4,946,778; Bird, (1988) Science 242:423-42; Huston et al. (1988) Proc. Natl. Acad. Sci. USA 85:5879-5883; and Ward et al. (1989) Nature 334:544-5], or any other molecule with the same specificity as the antibody of the invention. Single chain antibodies are formed by linking the heavy and light chain fragments of the Fv region via an amino acid bridge, resulting in a single chain polypeptide. Techniques for the assembly of functional Fv fragments in E. coli may be used [Skerra et al. (1988) Science 242:1038-1041].

In other embodiments, the invention provides fusion proteins of the immunoglobulins of the invention (or functionally active fragments thereof), for example in which the immunoglobulin is fused via a covalent bond (e.g. a peptide bond), at either the N-terminus or the C-terminus to an amino acid sequence of another protein (or portion thereof, preferably at least 10, 20 or 50 amino acid portion of the protein) that is not the immunoglobulin. Preferably the immunoglobulin, or fragment thereof, is covalently linked to the other protein at the N-terminus of the constant domain. As stated above, such fusion proteins may facilitate purification, increase half-life in vivo, and enhance the delivery of an antigen across an epithelial barrier to the immune system.

The immunoglobulins of the invention include analogs and derivatives that are modified, i.e. by the covalent attachment of any type of molecule as long as such covalent attachment does not impair immunospecific binding. For example, but not by way of limitation, the derivatives and analogs of the immunoglobulins include those that have been further modified, e.g. by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the analog or derivative may contain one or more non-classical amino acids.

Immunization of Mice

Mice can be immunized with a purified or enriched preparation of the BST1 antigen and/or recombinant BST1, or cells expressing BST1. Preferably, the mice will be 6-16 weeks of age upon the first infusion. For example, a purified or recombinant preparation (100 μg) of the BST1 antigen can be used to immunize the mice intraperitoneally.

Cumulative experience with various antigens has shown that the mice respond when immunized intraperitoneally (IP) with antigen in complete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA (as described below) to test for satisfactory titres. Mice can be boosted intravenously with antigen on 3 consecutive days with sacrifice and removal of the spleen taking place 5 days later. In one embodiment, A/J mouse strains (Jackson Laboratories, Bar Harbor, Me.) may be used.

Generation of Transfectomas Producing Monoclonal Antibodies

Antibodies of the invention can be produced in a host cell transfectoma using, for example, a combination of recombinant DNA techniques and gene transfection methods as is well known in the art [e.g. Morrison, S. (1985) Science 229:1202].

For example, to express the antibodies, or antibody fragments thereof, DNAs encoding partial or full-length light and heavy chains, can be obtained by standard molecular biology techniques (e.g. PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain [Proudfoot (1986) Nature 322:52; Kohler (1980) Proc. Natl. Acad. Sci. USA 77:2197]. The coding sequences for the heavy and light chains may comprise cDNA or genomic DNA.

The antibody genes are inserted into the expression vector by standard methods (e.g. ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_K$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e. a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g. polyadenylation signals) that control the transcription or translation of the antibody chain genes. Such regulatory sequences are described, for example, in Goeddel (Gene Expression Technology, *Methods in Enzymology* 185, Academic Press, San Diego, Calif. (1990). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g. the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 [Takebe, Y. et al. (1988) *Mol. Cell. Biol.* 8:466-472].

In addition to the antibody chain genes and regulatory sequences, the recombinant expression vectors of the invention may carry additional sequences, such as sequences that regulate replication of the vector in host cells (e.g. origins of replication) and selectable marker genes. The selectable marker gene facilitates selection of host cells into which the vector has been introduced (see, e.g. U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g. electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody [Boss, M. A. and Wood, C. R. (1985) *Immunology Today* 6:12-13].

Preferred mammalian host cells for expressing the recombinant antibodies of the invention include Chinese hamster ovary cells (CHO), in conjunction with a vector such as the major intermediate early gene promoter element from human cytomegalovirus [Foecking et al., 1986, *Gene* 45:101; Cockett et al. (1990) *BioTechnology* 8:2], dhfr-CHO cells, described in Urlaub and Chasin (1980) *Proc. Natl. Acad. Sci. USA* 77:4216-4220, used with a DHFR selectable marker, e.g. as described in R. J. Kaufman and P. A. Sharp (1982) *J. Mol. Biol.* 159:601-621), NSO myeloma cells, COS cells and SP2 cells. In particular, for use with NSO myeloma cells, another preferred expression system is the GS gene expression system disclosed in WO 87/04462 (to Wilson), WO 89/01036 (to Bebbington) and EP 338,841 (to Bebbington).

A variety of host expression vector systems may be utilized to express an antibody molecule of the invention. Such host-expression systems represent vehicles by which the coding sequences of interest may be produced and subsequently purified, but also represent cells which may, when transformed or transfected with the appropriate nucleotide coding sequences, express the antibody molecule of the invention in situ. These include but are not limited to microorganisms such as bacteria (e.g. *E. coli, B. subtilis*) transformed with recombinant bacteriophage DNA, plasmid DNA or cosmid DNA expression vectors containing antibody coding sequences; yeast (e.g. *Saccharomyces, Pichia*) transformed with recombinant yeast expression vectors containing antibody coding sequences; insect cell systems infected with recombinant virus expression vectors (e.g. baculovirus) containing the antibody coding sequences; plant cell systems infected with recombinant virus expression vectors (e.g. cauliflower mosaic virus, CaMV; tobacco mosaic virus, TMV) or transformed with recombinant plasmid expression vectors (e.g. Ti plasmid) containing antibody coding sequences; or mammalian cell systems (e.g. COS, CHO, BHK, 293, 3T3 cells) harboring recombinant expression constructs containing promoters derived from the genome of mammalian cells (e.g. metallothionein promoter) or from mammalian viruses (e.g. the adenovirus late promoter; the vaccinia virus 7.5K promoter).

In bacterial systems, a number of expression vectors may be advantageously selected depending upon the use intended for the antibody molecule being expressed. For example, when a large quantity of such a protein is to be produced, for the generation of pharmaceutical compositions comprising an antibody molecule, vectors which direct the expression of high levels of fusion protein products that are readily purified may be desirable. Such vectors include, but are not limited, to the *E. coli* expression vector pUR278 (Ruther et al. (1983) *EMBO J.* 2:1791), in which the antibody coding sequence may be ligated individually into the vector in frame with the lac Z coding region so that a fusion protein is produced; pIN vectors [Inouye & Inouye (1985) *Nucleic Acids Res.* 13:3101-3109; Van Heeke & Schuster (1989) *J. Biol. Chem.* 24:5503-5509]; and the similar pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter). In mammalian host cells, a number of viral-based expression systems (e.g. an adenovirus expression system) may be utilized.

As discussed above, a host cell strain may be chosen which modulates the expression of the inserted sequences, or modifies and processes the gene product in the specific fashion desired. Such modifications (e.g. glycosylation) and processing (e.g. cleavage) of protein products may be important for the function of the protein.

For long-term, high-yield production of recombinant antibodies, stable expression is preferred. For example, cell lines that stably express an antibody of interest can be produced by transfecting the cells with an expression vector comprising the nucleotide sequence of the antibody and the nucleotide sequence of a selectable (e.g. neomycin or hygromycin), and selecting for expression of the selectable marker. Such engineered cell lines may be particularly useful in screening and evaluation of compounds that interact directly or indirectly with the antibody molecule.

The expression levels of the antibody molecule can be increased by vector amplification [for a review, see Bebbington and Hentschel, The use of vectors based on gene amplification for the expression of cloned genes in mammalian cells in DNA cloning, Vol. 3. (Academic Press, New York, 1987)]. When a marker in the vector system expressing antibody is amplifiable, increase in the level of inhibitor present in culture of host cell will increase the number of copies of the marker gene. Since the amplified region is associated with the antibody gene, production of the antibody will also increase [Crouse et al., 1983, *Mol. Cell. Biol.* 3:257].

When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Once the antibody molecule of the invention has been recombinantly expressed, it may be purified by any method known in the art for purification of an antibody molecule, for example, by chromatography (e.g. ion exchange chromatography, affinity chromatography such as with protein A or specific antigen, and sizing column chromatography), centrifugation, differential solubility, or by any other standard technique for the purification of proteins.

Alternatively, any fusion protein may be readily purified by utilizing an antibody specific for the fusion protein being expressed. For example, a system described by Janknecht et al. allows for the ready purification of non-denatured fusion proteins expressed in human cell lines [Janknecht et al., 1991, *Proc. Natl. Acad. Sci. USA* 88:8972-897]. In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with recombinant vaccinia virus are loaded onto $Ni^{2+}$ nitriloacetic acid-agarose columns and histidine-tagged proteins are selectively eluted with imidazole-containing buffers.

Characterization of Antibody Binding to Antigen

The antibodies that are generated by these methods may then be selected by first screening for affinity and specificity with the purified polypeptide of interest and, if required, comparing the results to the affinity and specificity of the antibodies with polypeptides that are desired to be excluded from binding. The antibodies can be tested for binding to the BST1 by, for example, standard ELISA. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) is present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ, certain antibody pairs (e.g. in sandwich assays) may interfere with one another sterically, etc., assay performance of an antibody may be a more important measure than absolute affinity and specificity of an antibody.

Those skilled in the art will recognize that many approaches can be taken in producing antibodies or binding fragments and screening and selecting for affinity and specificity for the various polypeptides, but these approaches do not change the scope of the invention.

To determine if the selected anti-BST1 monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using the BST1 coated-ELISA plates. Biotinylated mAb binding can be detected with a streptavidin-alkaline phosphatase probe.

To determine the isotype of purified antibodies, isotype ELISAs can be performed using reagents specific for antibodies of a particular isotype.

Anti-BST1 antibodies can be further tested for reactivity with the BST1 antigen by Western blotting. Briefly, BST1 can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested.

The binding specificity of an antibody of the invention may also be determined by monitoring binding of the antibody to cells expressing BST1, for example, by flow cytometry. Typically, a cell line, such as a CHO cell line, may be transfected with an expression vector encoding BST1. The transfected protein may comprise a tag, such as a myc-tag, preferably at the N-terminus, for detection using an antibody to the tag. Binding of an antibody of the invention to BST1 may be determined by incubating the transfected cells with the antibody, and detecting bound antibody. Binding of an antibody to the tag on the transfected protein may be used as a positive control.

The specificity of an antibody of the invention for BST1 may be further studied by determining whether or not the antibody binds to other proteins, such as another member of the Eph family using the same methods by which binding to BST1 is determined.

Immunoconjugates

In another aspect, the present invention features an anti-BST1 antibody, or a fragment thereof, conjugated to a therapeutic moiety, such as a cytotoxin, a drug (e.g. an immunosuppressant) or a radiotoxin. Such conjugates are referred to herein as "immunoconjugates". Immunoconjugates that include one or more cytotoxins are referred to as "immunotoxins". A cytotoxin or cytotoxic agent includes any agent that is detrimental to (e.g. kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, and anthramycin (AMC)), and antimitotic agents (e.g. vincristine and vinblastine).

Other preferred examples of therapeutic cytotoxins that can be conjugated to an antibody of the invention include duocarmycins, calicheamicins, maytansines and auristatins, and derivatives thereof. An example of a calicheamicin antibody conjugate is commercially available (Mylotarg®; American Home Products).

Cytotoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g. cathepsins B, C, D).

Examples of cytotoxins are described, for example, in U.S. Pat. Nos. 6,989,452, 7,087,600, and 7,129,261, and in PCT Application Nos. PCT/US2002/17210, PCT/US2005/017804, PCT/US2006/37793, PCT/US2006/060050, PCT/US2006/060711, WO2006/110476, and in U.S. Patent Application No. 60/891,028, all of which are incorporated herein by reference in their entirety. For further discussion of types of cytotoxins, linkers and methods for conjugating therapeutic agents to antibodies, see also Saito, G. et al. (2003) *Adv. Drug Deliv. Rev.* 55:199-215; Trail, P. A. et al. (2003) *Cancer Immunol. Immunother.* 52:328-337; Payne, G. (2003) *Cancer Cell* 3:207-212; Allen, T. M. (2002) *Nat. Rev. Cancer* 2:750-763; Pastan, I. and Kreitman, R. J. (2002) *Curr. Opin. Investig. Drugs* 3:1089-1091; Senter, P. D. and Springer, C. J. (2001) *Adv. Drug Deliv. Rev.* 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine131, indium111, yttrium90 and lutetium177. Method for preparing radioimmunoconjugates are established in the art. Examples of radioimmunoconjugates are commercially available, including Zevalin® (IDEC Pharmaceuticals) and Bexxar® (Corixa Pharmaceuticals), and similar methods can be used to prepare radioimmunoconjugates using the antibodies of the invention.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *pseudomonas* exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g. Arnon et al., "Monoclonal Antibodies For Immunotargeting Of Drugs In Cancer Therapy," in *Monoclonal Antibodies And Cancer Therapy*, Reisfeld et al. (eds.), pp. 243-56 (Alan R. Liss, Inc. 1985); Hellstrom et al., "Antibodies For Drug Delivery," in *Controlled Drug Delivery* (2nd Ed.), Robinson et al. (eds.), pp. 623-53 (Marcel Dekker, Inc. 1987); Thorpe, "Antibody Carriers Of Cytotoxic Agents In Cancer Therapy: A Review," in *Monoclonal Antibodies '84: Biological And Clinical Applications*, Pinchera et al. (eds.), pp. 475-506 (1985); "Analysis, Results, And Future Prospective Of The Therapeutic Use Of Radiolabeled Antibody In Cancer Therapy," in *Monoclonal Antibodies For Cancer Detection And Therapy*, Baldwin et al. (eds.), pp. 303-16 (Academic Press 1985), and Thorpe et al., *Immunol. Rev.*, 62:119-58 (1982).

Bispecific Molecules

In another aspect, the present invention features bispecific molecules comprising an anti-BST1 antibody, or a fragment thereof, of the invention. An antibody of the invention, or antigen-binding portions thereof, can be derivatized or linked to another functional molecule, e.g. another peptide or protein (e.g. another antibody or ligand for a receptor) to generate a bispecific molecule that binds to at least two different binding sites or target molecules. The antibody of the invention may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the invention, an antibody of the invention can be functionally linked (e.g. by chemical coupling, genetic fusion, non-covalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for a first target epitope (i.e. BST1) and a second binding specificity for a second target epitope. The second target epitope maybe present on the same target protein as that bound by the first binding specificity; or the second target epitope may be present of a different target protein to that bound by the first protein to that bound by the first binding specificity. The second target epitope may be present on the same cell as the first target epitope (i.e. BST1); or the second target epitope may be present on a target which is not displayed by the cell which displays the first target epitope. As used herein, the term 'binding specificity' refers to a moiety comprising at least one antibody variable domain.

In a one embodiment of the invention, the second target epitope is an Fc receptor, e.g. human FcγRI (CD64) or a human Fcα receptor (CD89). Therefore, the invention includes bispecific molecules capable of binding both to FcγR or FcαR expressing effector cells (e.g. monocytes, macrophages or polymorphonuclear cells (PMNs), and to target cells expressing BST1. These bispecific molecules target BST1 expressing cells to effector cell and trigger Fc receptor-mediated effector cell activities, such as phagocytosis of BST1 expressing cells, antibody dependent cell-mediated cytotoxicity (ADCC), cytokine release, or generation of superoxide anion.

In another embodiment of the invention, the second target epitope is CD3 or CD5. Therefore, the invention includes bispecific molecules capable of binding both to CD3 or CD5 expressing effector cells (e.g. CD3 or CD5 expressing cytotoxic T cells), and to target cells expressing BST1. These bispecific molecules target BST1 expressing cells to effector cell and trigger CD3 or CD5-mediated effector cell activities, such as T cell clonal expansion and T cell cytotoxicity. In this embodiment, the bispecific antibody of the invention may have a total of either two or three antibody variable domains, wherein first portion of the bispecific antibody is capable of recruiting the activity of a human immune effector cell by specifically binding to an effector antigen located on the human immune effector cell, in which the effector antigen is the human CD3 or CD5 antigen, said first portion consisting of one antibody variable domain, and a second portion of the bispecific antibody is capable of specifically binding to a target antigen other than the effector antigen e.g. BST1, said target antigen being located on a target cell other than said human immune effector cell, and said second portion comprising one or two antibody variable domains.

In an embodiment of the invention in which the bispecific molecule is multispecific, the molecule can further include a third binding specificity, in addition to an anti-Fc binding specificity or anti-CD3 or CD5 binding specificity and an anti-BST1 binding specificity. In one embodiment, the third binding specificity is an anti-enhancement factor (EF) portion, e.g. a molecule which binds to a surface protein involved in cytotoxic activity and thereby increases the immune response against the target cell. The "anti-enhancement factor portion" can be an antibody, functional antibody fragment or a ligand that binds to a given molecule, e.g. an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g. via CD2, CD3, CD8, CD28, CD4, CD40, ICAM-1 or other immune cell that results in an increased immune response against the target cell).

In one embodiment, the bispecific molecules of the invention comprise as a binding specificity at least one antibody, or an antibody fragment thereof, including, e.g. an Fab, Fab', F(ab')2, Fv, Fd, dAb or a single chain Fv. The antibody may also be a light chain or heavy chain dimer, or any minimal fragment thereof such as an Fv or a single chain construct as described in U.S. Pat. No. 4,946,778, the contents of which is expressly incorporated by reference.

In one embodiment, the binding specificity for an Fcγ receptor is provided by a monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), FcγRII(CD32), and FcγRIII (CD16). In one preferred embodiment, the Fcγ receptor is a human high affinity FcγRI. The human FcγRI is a 72 kDa molecule, which shows high affinity for monomeric IgG ($10^8$-$10^9$ $M^{-1}$).

The production and characterization of certain preferred anti-Fcγ monoclonal antibodies are described in PCT Publication WO 88/00052 and in U.S. Pat. No. 4,954,617, the teachings of which are fully incorporated by reference herein. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this invention are mAb 22, mAb 32, mAb 44, mAb 62 and mAb 197. The hybridoma producing mAb 32 is available from the American Type Culture Collection, ATCC Accession No. HB9469. In other embodiments, the anti-Fcγ receptor antibody is a humanized form of monoclonal antibody 22 (H22). The production and characterization of the H22 antibody is described in Graziano, R. F. et al. (1995) J. Immunol 155 (10): 4996-5002 and PCT Publication WO 94/10332. The H22 antibody producing cell line was deposited at the American Type Culture Collection under the designation HA022CL1 and has the accession no. CRL 11177.

In still other preferred embodiments, the binding specificity for an Fc receptor is provided by an antibody that binds to a human IgA receptor, e.g. an Fc-alpha receptor [FcαRI (CD89)], the binding of which is preferably not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity ($\approx 5 \times 10^7$ $M^{-1}$) for both IgA1 and IgA2, which is increased upon exposure to cytokines such as G-CSF or GM-CSF [Morton, H. C. et al. (1996) Critical Reviews in Immunology 16:423-440]. Four FcαRI-specific monoclonal antibodies, identified as A3, A59, A62 and A77, which bind FcαRI outside the IgA ligand binding domain, have been described [Monteiro, R. C. et al. (1992) J. Immunol. 148:1764].

FcαRI and FcγRI are preferred trigger receptors for use in the bispecific molecules of the invention because they are (1) expressed primarily on immune effector cells, e.g. monocytes, PMNs, macrophages and dendritic cells; (2) expressed at high levels (e.g. 5,000-100,000 per cell); (3) mediators of cytotoxic activities (e.g. ADCC, phagocytosis); and (4) mediate enhanced antigen presentation of antigens, including self-antigens, targeted to them.

Antibodies which can be employed in the bispecific molecules of the invention are murine, human, chimeric and humanized monoclonal antibodies.

The bispecific molecules of the present invention can be prepared by conjugating the constituent binding specificities, e.g. the anti-FcR, anti-CD3, anti-CD5 and anti-BST1 binding specificities, using methods known in the art. For example, the binding specificity of each bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) [see e.g. Karpovsky et al. (1984) *J. Exp. Med.* 160:1686; Liu, M A et al. (1985) *Proc. Natl. Acad. Sci. USA* 82:8648]. Other methods include those described in Paulus (1985) *Behring Ins. Mitt.* No. 78, 118-132; Brennan et al. (1985) Science 229:81-83, and Glennie et al. (1987) *J. Immunol.* 139: 2367-2375. Preferred conjugating agents are SATA and sulfo-SMCC, both available from Pierce Chemical Co. (Rockford, Ill.)].

Additional bivalent work has been done for bispecifics by engineering dual binding into full length antibody-like formats (Wu et al., 2007, Nature Biotechnology 25[11]:1290-1297; U.S. Ser. No. 12/477,711; Michaelson et al., 2009, mAbs 1[2]:128-141; PCT/US2008/074693; Zuo et al., 2000, Protein Engineering 13[5]:361-367; U.S. Ser. No. 09/865, 198; Shen et al., 2006, J Biol Chem 281[16]:10706-10714; Lu et al., 2005, J Biol Chem 280[20]:19665-19672; PCT/US2005/025472; expressly incorporated herein by reference).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand x Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858, all of which are expressly incorporated herein by reference.

Binding of the bispecific molecules to their specific targets can be confirmed by, for example, enzyme-linked immunosorbent assay (ELISA), radioimmunoassay (RIA), FACS analysis, bioassay (e.g. growth inhibition), or Western Blot assay. Each of these assays generally detects the presence of protein-antibody complexes of particular interest by employing a labeled reagent (e.g. an antibody) specific for the complex of interest. For example, the FcR-antibody complexes can be detected using e.g. an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

Antibody Fragments and Antibody Mimetics

The instant invention is not limited to traditional antibodies and may be practiced through the use of antibody fragments and antibody mimetics. As detailed below, a wide variety of antibody fragments and antibody mimetic technologies has now been developed and are widely known in the art. While a number of these technologies, such as domain antibodies, Nanobodies, and UniBodies make use of fragments of, or other modifications to, traditional antibody structures, there are also alternative technologies, such as affibodies, DARPins, Anticalins, Avimers, and Versabodies that employ binding structures that, while they mimic traditional antibody binding, are generated from and function via distinct mechanisms.

Domain antibodies (dAbs) are the smallest functional binding units of antibodies, corresponding to the variable regions of either the heavy ($V_H$) or light ($V_L$) chains of human antibodies. Domain Antibodies have a molecular weight of approximately 13 kDa. Domantis has developed a series of large and highly functional libraries of fully human $V_H$ and $V_L$ dAbs (more than ten billion different sequences in each library), and uses these libraries to select dAbs that are specific to therapeutic targets. In contrast to many conventional antibodies, domain antibodies are well expressed in bacterial, yeast, and mammalian cell systems. Further details of domain antibodies and methods of production thereof may be obtained by reference to U.S. Pat. Nos. 6,291,158; 6,582,915; 6,593,081; 6,172,197; 6,696,245; US Serial No. 2004/0110941; European patent application No. 1433846 and European Patents 0368684 & 0616640; WO05/035572, WO04/101790, WO04/081026, WO04/058821, WO04/003019 and WO03/002609, each of which is herein incorporated by reference in its entirety.

Nanobodies are antibody-derived therapeutic proteins that contain the unique structural and functional properties of naturally-occurring heavy-chain antibodies. These heavy-chain antibodies contain a single variable domain (VHH) and two constant domains ($C_H2$ and $C_H3$). Importantly, the cloned and isolated VHH domain is a perfectly stable polypeptide harboring the full antigen-binding capacity of the original heavy-chain antibody. Nanobodies have a high homology with the $V_H$ domains of human antibodies and can be further humanized without any loss of activity. Importantly, Nanobodies have a low immunogenic potential, which has been confirmed in primate studies with Nanobody lead compounds.

Nanobodies combine the advantages of conventional antibodies with important features of small molecule drugs. Like conventional antibodies, Nanobodies show high target specificity, high affinity for their target and low inherent toxicity. However, like small molecule drugs they can inhibit enzymes and readily access receptor clefts. Furthermore, Nanobodies are extremely stable, can be administered by means other than injection (see e.g. WO 04/041867, which is herein incorporated by reference in its entirety) and are easy to manufacture. Other advantages of Nanobodies include recognizing uncommon or hidden epitopes as a result of their small size, binding into cavities or active sites of protein targets with high affinity and selectivity due to their unique 3-dimensional, drug format flexibility, tailoring of half-life and ease and speed of drug discovery.

Nanobodies are encoded by single genes and are efficiently produced in almost all prokaryotic and eukaryotic hosts e.g. *E. coli* (see e.g. U.S. Pat. No. 6,765,087, which is herein incorporated by reference in its entirety), molds (for example *Aspergillus* or *Trichoderma*) and yeast (for example *Saccharomyces, Kluyveromyces, Hansenula* or *Pichia*) (see e.g. U.S. Pat. No. 6,838,254, which is herein incorporated by reference in its entirety). The production process is scalable and multi-kilogram quantities of Nanobodies have been produced. Since Nanobodies exhibit a superior stability compared with conventional antibodies, they can be formulated as a long shelf-life, ready-to-use solution.

The Nanoclone method (see e.g. WO 06/079372, which is herein incorporated by reference in its entirety) is a proprietary method for generating Nanobodies against a desired target, based on automated high-throughout selection of B-cells and could be used in the context of the instant invention.

UniBodies are another antibody fragment technology; however this one is based upon the removal of the hinge region of IgG4 antibodies. The deletion of the hinge region results in a molecule that is essentially half the size of traditional IgG4 antibodies and has a univalent binding region rather than the bivalent binding region of IgG4 antibodies. It is also well known that IgG4 antibodies are inert and thus do not interact with the immune system, which may be advantageous for the treatment of diseases where an immune response is not desired, and this advantage is passed onto UniBodies. For example, UniBodies may function to inhibit or silence, but not kill, the cells to which they are bound. Additionally, UniBody binding to cancer cells do not stimulate them to proliferate. Furthermore, because UniBodies are about half the size of traditional IgG4 antibodies, they may show better distribution over larger solid tumors with potentially advantageous efficacy. UniBodies are cleared from the body at a similar rate to whole IgG4 antibodies and are able to bind with a similar affinity for their antigens as whole antibodies. Further details of UniBodies may be obtained by reference to patent publication WO2007/059782, which is herein incorporated by reference in its entirety.

Affibody molecules represent a new class of affinity proteins based on a 58-amino acid residue protein domain, derived from one of the IgG-binding domains of staphylococcal protein A. This three helix bundle domain has been used as a scaffold for the construction of combinatorial phagemid libraries, from which Affibody variants that target the desired molecules can be selected using phage display technology [Nord K, Gunneriusson E, Ringdahl J, Stahl S, Uhlen M, Nygren P A (1997) 'Binding proteins selected from combinatorial libraries of an α-helical bacterial receptor domain' *Nat Biotechnol* 15:772-7. Ronmark J, Gronlund H, Uhlen M, Nygren P A (2002) 'Human immunoglobulin A (IgA)-specific ligands from combinatorial engineering of protein A' *Eur J Biochem.* 269:2647-55.]. The simple, robust structure of Affibody molecules in combination with their low molecular weight (6 kDa), make them suitable for a wide variety of applications, for instance, as detection reagents [Ronmark J. et al. (2002) 'Construction and characterization of affibody-Fc chimeras produced in *Escherichia coli*' *J Immunol Methods* 261:199-211] and to inhibit receptor interactions [Sandstorm K, Xu Z, Forsberg G, Nygren P A (2003) 'Inhibition of the CD28-CD80 co-stimulation signal by a CD28-binding Affibody ligand developed by combinatorial protein engineering' *Protein Eng* 16:691-7]. Further details of Affibodies and methods of production thereof may be obtained by reference to U.S. Pat. No. 5,831,012 which is herein incorporated by reference in its entirety.

Labeled Affibodies may also be useful in imaging applications for determining abundance of isoforms.

DARPins (Designed Ankyrin Repeat Proteins) are one example of an antibody mimetic DRP (Designed Repeat Protein) technology that has been developed to exploit the binding abilities of non-antibody polypeptides. Repeat proteins such as ankyrin or leucine-rich repeat proteins, are ubiquitous binding molecules, which occur, unlike antibodies, intra- and extracellularly. Their unique modular architecture features repeating structural units (repeats), which stack together to form elongated repeat domains displaying variable and modular target-binding surfaces. Based on this modularity, combinatorial libraries of polypeptides with highly diversified binding specificities can be generated. This strategy includes the consensus design of self-compatible repeats displaying variable surface residues and their random assembly into repeat domains.

DARPins can be produced in bacterial expression systems at very high yields and they belong to the most stable proteins known. Highly specific, high-affinity DARPins to a broad range of target proteins, including human receptors, cytokines, kinases, human proteases, viruses and membrane proteins, have been selected. DARPins having affinities in the single-digit nanomolar to picomolar range can be obtained.

DARPins have been used in a wide range of applications, including ELISA, sandwich ELISA, flow cytometric analysis (FACS), immunohistochemistry (IHC), chip applications, affinity purification or Western blotting. DARPins also proved to be highly active in the intracellular compartment, for example, as intracellular marker proteins fused to green fluorescent protein (GFP). DARPins were further used to inhibit viral entry with IC50 in the pM range. DARPins are not only ideal to block protein-protein interactions, but also to inhibit enzymes. Proteases, kinases and transporters have been successfully inhibited, most often an allosteric inhibition mode. Very fast and specific enrichments on the tumor and very favorable tumor to blood ratios make DARPins well suited for in vivo diagnostics or therapeutic approaches.

Additional information regarding DARPins and other DRP technologies can be found in US Patent Application Publication No. 2004/0132028, and International Patent Publication No. WO 02/20565, both of which are hereby incorporated by reference in their entirety.

Anticalins are an additional antibody mimetic technology. However in this case the binding specificity is derived from lipocalins, a family of low molecular weight proteins that are naturally and abundantly expressed in human tissues and body fluids. Lipocalins have evolved to perform a range of functions in vivo associated with the physiological transport and storage of chemically sensitive or insoluble compounds. Lipocalins have a robust intrinsic structure comprising a highly conserved β-barrel which supports four loops at one terminus of the protein. These loops form the entrance to a binding pocket and conformational differences in this part of the molecule account for the variation in binding specificity between individual lipocalins.

While the overall structure of hypervariable loops supported by a conserved β-sheet framework is reminiscent of immunoglobulins, lipocalins differ considerably from antibodies in terms of size, being composed of a single polypeptide chain of 160-180 amino acids which is marginally larger than a single immunoglobulin domain.

Lipocalins are cloned and their loops are subjected to engineering in order to create Anticalins. Libraries of structurally diverse Anticalins have been generated and Anticalin display allows the selection and screening of binding function, followed by the expression and production of soluble protein for further analysis in prokaryotic or eukaryotic systems. Studies have successfully demonstrated that Anticalins can be developed that are specific for virtually any human target protein can be isolated and binding affinities in the nanomolar or higher range can be obtained.

Anticalins can also be formatted as dual targeting proteins, so-called Duocalins. A Duocalin binds two separate therapeutic targets in one easily produced monomeric protein using standard manufacturing processes while retaining target specificity and affinity regardless of the structural orientation of its two binding domains.

Modulation of multiple targets through a single molecule is particularly advantageous in diseases known to involve more than a single causative factor. Moreover, bi- or multivalent binding formats such as Duocalins have significant potential in targeting cell surface molecules in disease, mediating agonistic effects on signal transduction pathways or inducing enhanced internalization effects via binding and clustering of cell surface receptors. Furthermore, the high intrinsic stability of Duocalins is comparable to monomeric Anticalins, offering flexible formulation and delivery potential for Duocalins.

Additional information regarding Anticalins can be found in U.S. Pat. No. 7,250,297 and International Patent Publication No. WO 99/16873, both of which are hereby incorporated by reference in their entirety.

Another antibody mimetic technology useful in the context of the instant invention are Avimers. Avimers are evolved from a large family of human extracellular receptor domains by in vitro exon shuffling and phage display, generating multidomain proteins with binding and inhibitory properties. Linking multiple independent binding domains has been shown to create avidity and results in improved affinity and specificity compared with conventional single-epitope binding proteins. Other potential advantages include simple and efficient production of multitarget-specific molecules in *Escherichia coli*, improved thermostability and resistance to proteases. Avimers with sub-nanomolar affinities have been obtained against a variety of targets.

Additional information regarding Avimers can be found in US Patent Application Publication Nos. 2006/0286603, 2006/0234299, 2006/0223114, 2006/0177831, 2006/0008844, 2005/0221384, 2005/0164301, 2005/0089932, 2005/0053973, 2005/0048512, 2004/0175756, all of which are hereby incorporated by reference in their entirety.

Versabodies are another antibody mimetic technology that could be used in the context of the instant invention. Versabodies are small proteins of 3-5 kDa with >15% cysteines, which form a high disulfide density scaffold, replacing the hydrophobic core that typical proteins have. The replacement of a large number of hydrophobic amino acids, comprising the hydrophobic core, with a small number of disulfides results in a protein that is smaller, more hydrophilic (less aggregation and non-specific binding), more resistant to proteases and heat, and has a lower density of T-cell epitopes, because the residues that contribute most to MHC presentation are hydrophobic. All four of these properties are well-known to affect immunogenicity, and together they are expected to cause a large decrease in immunogenicity.

The inspiration for Versabodies comes from the natural injectable biopharmaceuticals produced by leeches, snakes, spiders, scorpions, snails, and anemones, which are known to exhibit unexpectedly low immunogenicity. Starting with selected natural protein families, by design and by screening the size, hydrophobicity, proteolytic antigen processing and epitope density are minimized to levels far below the average for natural injectable proteins.

Given the structure of Versabodies, these antibody mimetics offer a versatile format that includes multi-valency, multi-specificity, a diversity of half-life mechanisms, tissue targeting modules and the absence of the antibody Fc region. Furthermore, Versabodies are manufactured in *E. coli* at high yields, and because of their hydrophilicity and small size, Versabodies are highly soluble and can be formulated to high concentrations. Versabodies are exceptionally heat stable (they can be boiled) and offer extended shelf-life.

Additional information regarding Versabodies can be found in US Patent Application Publication No. 2007/0191272 which is hereby incorporated by reference in its entirety.

The detailed description of antibody fragment and antibody mimetic technologies provided above is not intended to be a comprehensive list of all technologies that could be used in the context of the instant specification. For example, and also not by way of limitation, a variety of additional technologies including alternative polypeptide-based technologies, such as fusions of complimentary determining regions as outlined in Qui et al. (2007) *Nature Biotechnology* 25(8):921-929, which is hereby incorporated by reference in its entirety, as well as nucleic acid-based technologies, such as the RNA aptamer technologies described in U.S. Pat. Nos. 5,789,157, 5,864,026, 5,712,375, 5,763,566, 6,013,443, 6,376,474, 6,613,526, 6,114,120, 6,261,774, and 6,387,620, all of which are hereby incorporated by reference, could be used in the context of the instant invention.

Pharmaceutical Compositions

In another aspect, the present invention provides a composition, e.g. a pharmaceutical composition, containing one or a combination of monoclonal antibodies, or antigen-binding portion(s) thereof, of the present invention, formulated together with a pharmaceutically acceptable carrier. Such compositions may include one or a combination of (e.g. two or more different) antibodies, or immunoconjugates or bispecific molecules of the invention. For example, a pharmaceutical composition of the invention can comprise a combination of antibodies (or immunoconjugates or bispecifics) that bind to different epitopes on the target antigen or that have complementary activities.

Pharmaceutical compositions of the invention also can be administered in combination therapy, i.e. combined with other agents. For example, the combination therapy can include an anti-antibody of the present invention combined with at least one other anti-tumor agent, or an anti-inflammatory or immunosuppressant agent. Examples of therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion). Depending on the route of administration, the active compound, i.e. antibody, immunoconjugate, or bispecific molecule, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects [see, e.g. Berge, S. M., et al. (1977) *J. Pharm. Sci.* 66:1-19]. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like.

Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of 100 percent, this amount will range from about 0.01 percent to about 99 percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g. a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-BST1 antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-BST1 antibody of the invention preferably results in a decrease in severity of disease symptoms, an increase in frequency and duration of disease symptom-free periods, or a prevention of impairment or disability due to the disease affliction. For example, for the treatment of the BST1 mediated tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit cell growth, such inhibition can be measured in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art [see, e.g. *Sustained and Controlled Release Drug Delivery Systems* (1978) J. R. Robinson, ed., Marcel Dekker, Inc., N.Y].

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g. U.S. Pat. Nos. 4,522,811; 5,374,548; and 5,399,331. The liposomes may comprise one or more moieties which are selectively transported into specific cells or organs, thus enhance targeted drug delivery [see, e.g. V. V. Ranade (1989) *J. Clin. Pharmacol.* 29:685]. Exemplary targeting moieties include folate or biotin (see, e.g. U.S. Pat. No. 5,416,016.); mannosides [Umezawa et al. (1988) Biochem. Biophys. Res. Commun. 153:1038]; antibodies [P. G. Bloeman et al. (1995) FEBS Lett. 357:140; M. Owais et al. (1995) Antimicrob. Agents Chemother. 39:180]; surfactant protein A receptor [Briscoe et al. (1995) Am. J. Physiol. 1233:134]; p 120 [Schreier et al. (1994) J. Biol. Chem. 269:9090]; see also K. Keinanen; M. L. Laukkanen (1994) FEBS Lett. 346:123; J. J. Killion; I. J. Fidler (1994) Immunomethods 4:273.

Uses and Methods

The antibodies, antibody compositions and methods of the present invention have numerous in vitro and in vivo diagnostic and therapeutic utilities involving the diagnosis and treatment of BST1 mediated disorders.

In some embodiments, these molecules can be administered to cells in culture, in vitro or ex vivo, or to human subjects, e.g. in vivo, to treat, prevent and to diagnose a variety of disorders. As used herein, the term "subject" is intended to include human and non-human animals. Non-human animals include all vertebrates, e.g. mammals and non-mammals, such as non-human primates, sheep, dogs, cats, cows, horses, chickens, amphibians, and reptiles. Preferred subjects include human patients having disorders mediated by BST1 activity. The methods are particularly suitable for treating human patients having a disorder associated with the aberrant BST1 expression. When antibodies to BST1 are administered together with another agent, the two can be administered in either order or simultaneously.

Given the specific binding of the antibodies of the invention for BST1, the antibodies of the invention can be used to specifically detect BST1 expression on the surface of cells and, moreover, can be used to purify BST1 via immunoaffinity purification.

Furthermore, given the expression of BST1 on tumor cells, the antibodies, antibody compositions and methods of the present invention can be used to treat a subject with a tumorigenic disorder, e.g. a disorder characterized by the presence of tumor cells expressing BST1 including, for example acute myeloid leukemia (AML), B-cell chronic lymphocytic leukemia, breast cancer, colorectal cancer, kidney cancer, head and neck cancer, lung cancer, ovarian cancer and pancreatic cancer. BST1 has been demonstrated to be internalised on antibody binding as illustrated in Example 5 below, thus enabling the antibodies of the invention to be used in any payload mechanism of action e.g. an ADC approach, radioimmunoconjugate, or ADEPT approach.

In one embodiment, the antibodies (e.g. monoclonal antibodies, multispecific and bispecific molecules and compositions) of the invention can be used to detect levels of BST1, or levels of cells which contain BST1 on their membrane surface, which levels can then be linked to certain disease symptoms. Alternatively, the antibodies can be used to inhibit or block BST1 function which, in turn, can be linked to the prevention or amelioration of certain disease symptoms, thereby implicating the BST1 as a mediator of the disease. This can be achieved by contacting a sample and a control sample with the anti-BST1 antibody under conditions that allow for the formation of a complex between the antibody and BST1. Any complexes formed between the antibody and the BST1 are detected and compared in the sample and the control.

In another embodiment, the antibodies (e.g. monoclonal antibodies, multispecific and bispecific molecules and compositions) of the invention can be initially tested for binding activity associated with therapeutic or diagnostic use in vitro. For example, compositions of the invention can be tested using the flow cytometric assays described in the Examples below.

The antibodies (e.g. monoclonal antibodies, multispecific and bispecific molecules, immunoconjugates and compositions) of the invention have additional utility in therapy and diagnosis of BST1 related diseases. For example, the monoclonal antibodies, the multispecific or bispecific molecules and the immunoconjugates can be used to elicit in vivo or in vitro one or more of the following biological activities: to inhibit the growth of and/or kill a cell expressing BST1; to mediate phagocytosis or ADCC of a cell expressing BST1 in the presence of human effector cells, or to block BST1 ligand binding to BST1.

In a particular embodiment, the antibodies (e.g. monoclonal antibodies, multispecific and bispecific molecules and compositions) are used in vivo to treat, prevent or diagnose a variety of BST1-related diseases. Examples of BST1-related diseases include, among others, human cancer tissues representing acute myeloid leukemia (AML), B-cell chronic lymphocytic leukemia, breast cancer, colorectal cancer, kidney cancer, head and neck cancer, lung cancer, ovarian cancer and pancreatic cancer.

Suitable routes of administering the antibody compositions (e.g. monoclonal antibodies, multispecific and bispecific molecules and immunoconjugates) of the invention in vivo and in vitro are well known in the art and can be selected by those of ordinary skill. For example, the antibody compositions can be administered by injection (e.g. intravenous or subcutaneous). Suitable dosages of the molecules used will depend on the age and weight of the subject and the concentration and/or formulation of the antibody composition.

As previously described, the anti-BST1 antibodies of the invention can be co-administered with one or other more therapeutic agents, e.g. a cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g. an anti-cancer therapy, e.g. radiation. Such therapeutic agents include, among others, anti-neoplastic agents such as doxorubicin (adriamycin), cisplatin bleomycin sulfate, carmustine, chlorambucil, and cyclophosphamide hydroxyurea which, by themselves, are only effective at levels which are toxic or subtoxic to a patient. Cisplatin is intravenously administered as a 100 mg/kg dose once every four weeks and adriamycin is intravenously administered as a 60-75 mg/ml dose once every 21 days. Other agents suitable for co-administration with the antibodies of the invention include other agents used for the treatment of cancers, e.g. acute myeloid leukemia (AML), B-cell chronic lymphocytic leukemia, breast cancer, colorectal cancer, kidney cancer, head and neck cancer, lung cancer, ovarian cancer or pancreatic cancer, such as Avastin®, 5FU and gemcitabine. Co-administration of the anti-BST1 antibodies or antigen binding fragments thereof, of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Target-specific effector cells, e.g. effector cells linked to compositions (e.g. monoclonal antibodies, multispecific and bispecific molecules) of the invention can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells can be administered as a suspension of cells in a physiologically acceptable solution. The number of cells administered can be in the order of $10^8$-$10^9$, but will vary depending on the therapeutic purpose. In general, the amount will be sufficient to obtain localization at the target cell, e.g. a tumor cell expressing BST1, and to affect cell killing by, e.g. phagocytosis. Routes of administration can also vary.

Therapy with target-specific effector cells can be performed in conjunction with other techniques for removal of targeted cells. For example, anti-tumor therapy using the compositions (e.g. monoclonal antibodies, multispecific and bispecific molecules) of the invention and/or effector cells armed with these compositions can be used in conjunction with chemotherapy. Additionally, combination immunotherapy may be used to direct two distinct cytotoxic effector populations toward tumor cell rejection. For example, anti-BST1 antibodies linked to anti-Fc-gamma RI or anti-CD3 may be used in conjunction with IgG- or IgA-receptor specific binding agents.

Bispecific and multispecific molecules of the invention can also be used to modulate FcγR or FcγR levels on effector cells, such as by capping and elimination of receptors on the cell surface. Mixtures of anti-Fc receptors can also be used for this purpose.

The compositions (e.g. monoclonal antibodies, multispecific and bispecific molecules and immunoconjugates) of the invention which have complement binding sites, such as portions from IgG1, -2, or -3 or IgM which bind complement, can also be used in the presence of complement. In one embodiment, ex vivo treatment of a population of cells comprising target cells with a binding agent of the invention and appropriate effector cells can be supplemented by the addition of complement or serum containing complement. Phagocytosis of target cells coated with a binding agent of the invention can be improved by binding of complement proteins. In another embodiment target cells coated with the compositions (e.g. monoclonal antibodies, multispecific and bispecific molecules) of the invention can also be lysed by complement. In yet another embodiment, the compositions of the invention do not activate complement.

The compositions (e.g. monoclonal antibodies, multispecific and bispecific molecules and immunoconjugates) of the invention can also be administered together with complement. In certain embodiments, the instant disclosure provides compositions comprising antibodies, multispecific or bispecific molecules and serum or complement. These compositions can be advantageous when the complement is located in close proximity to the antibodies, multispecific or bispecific molecules. Alternatively, the antibodies, multispecific or bispecific molecules of the invention and the complement or serum can be administered separately.

Also within the scope of the present invention are kits comprising the antibody compositions of the invention (e.g. monoclonal antibodies, bispecific or multispecific molecules, or immunoconjugates) and instructions for use. The kit can further contain one or more additional reagents, such as an immunosuppressive reagent, a cytotoxic agent or a radiotoxic agent, or one or more additional antibodies of the invention (e.g. an antibody having a complementary activity which binds to an epitope in the BST1 antigen distinct from the first antibody).

Accordingly, patients treated with antibody compositions of the invention can be additionally administered (prior to, simultaneously with, or following administration of an antibody of the invention) with another therapeutic agent, such as a cytotoxic or radiotoxic agent, which enhances or augments the therapeutic effect of the antibodies.

In other embodiments, the subject can be additionally treated with an agent that modulates, e.g. enhances or inhibits, the expression or activity of Fcγ or Fcγ receptors by, for example, treating the subject with a cytokine. Preferred cytokines for administration during treatment with the multispecific molecule include of granulocyte colony-stimulating factor (G-CSF), granulocyte-macrophage colony-stimulating factor (GM-CSF), interferon-γ (IFN-γ), and tumor necrosis factor (TNF).

The compositions (e.g. antibodies, multispecific and bispecific molecules) of the invention can also be used to target cells expressing FcγR or BST1, for example, for labeling such cells. For such use, the binding agent can be linked to a molecule that can be detected. Thus, the invention provides methods for localizing ex vivo or in vitro cells expressing Fc receptors, such as FcγR, or BST1. The detectable label can be, e.g. a radioisotope, a fluorescent compound, an enzyme, or an enzyme co-factor.

In a particular embodiment, the invention provides methods for detecting the presence of the BST1 antigen in a sample, or measuring the amount of the BST1 antigen, comprising contacting the sample, and a control sample, with a monoclonal antibody, or an antigen binding portion thereof, which specifically binds to BST1, under conditions that allow for formation of a complex between the antibody or portion thereof and BST1. The formation of a complex is then detected, wherein a difference complex formation between the sample compared to the control sample is indicative the presence of the BST1 antigen in the sample.

In other embodiments, the invention provides methods for treating a BST1 mediated disorder in a subject, e.g. human cancers and human inflammatory disease, including the diseases of the invention.

In yet another embodiment, immunoconjugates of the invention can be used to target compounds (e.g. therapeutic agents, labels, cytotoxins, radiotoxins immunosuppressants, etc.) to cells which have BST1 cell surface receptors by linking such compounds to the antibody. For example, an anti-BST1 antibody can be conjugated to any of the toxin compounds described in U.S. Pat. Nos. 6,281,354 and 6,548,530, US patent publication Nos. 2003/0050331, 2003/0064984, 2003/0073852, and 2004/0087497, or published in WO 03/022806. Thus, the invention also provides methods for localizing ex vivo or in vivo cells expressing BST1 (e.g. with a detectable label, such as a radioisotope, a fluorescent compound, an enzyme, or an enzyme co-factor). Alternatively, the immunoconjugates can be used to kill cells which have BST1 cell surface receptors by targeting cytotoxins or radiotoxins to BST1.

All references cited in this specification, including without limitation all papers, publications, patents, patent applications, presentations, texts, reports, manuscripts, brochures, books, internet postings, journal articles, periodicals, product fact sheets, and the like, one hereby incorporated by reference into this specification in their entireties. The discussion of the references herein is intended to merely summarize the assertions made by their authors and no admission is made that any reference constitutes prior art and Applicants' reserve the right to challenge the accuracy and pertinence of the cited references.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the dependant claims.

The present invention is further illustrated by the following examples which should not be construed as further limiting.

Example 1: Construction of a Phage-Display Library

A recombinant protein composed of amino acids 29-292 of BST1 (SEQ ID NO:44) was eurkaryotically synthesized by standard recombinant methods and used as antigen for immunization.

Immunization and mRNA Isolation

A phage display library for identification of the BST1-binding molecules was constructed as follows. A/J mice (Jackson Laboratories, Bar Harbor, Me.) were immunized intraperitoneally with the recombinant BST1 antigen (the extracellular domain), using 100 µg protein in Freund's complete adjuvant, on day 0, and with 100 µg antigen on day 28. Test bleeds of mice were obtained through puncture of the retro-orbital sinus. If, by testing the titers, they were deemed high by ELISA using the biotinylated BST1 antigen immobilized via neutravidin (Reacti-Bind™) NeutrAvidin™-Coated Polystyrene Plates, Pierce, Rockford, Ill.), the mice were boosted with 100 µg of protein on day 70, 71 and 72, with subsequent sacrifice and splenectomy on day 77. If titers of antibody were not deemed satisfactory, mice were boosted with 100 µg antigen on day 56 and a test bleed taken on day 63. If satisfactory titers were obtained, the animals were boosted with 100 µg of antigen on day 98, 99, and 100 and the spleens harvested on day 105.

The spleens were harvested in a laminar flow hood and transferred to a petri dish, trimming off and discarding fat and connective tissue. The spleens were macerated quickly with the plunger from a sterile 5 cc syringe in the presence of 1.0 ml of solution D (25.0 g guanidine thiocyanate (Boehringer Mannheim, Indianapolis, Ind.), 29.3 ml sterile water, 1.76 ml 0.75 M sodium citrate pH 7.0, 2.64 ml 10% sarkosyl (Fisher Scientific, Pittsburgh, Pa.), 0.36 ml 2-mercaptoethanol (Fisher Scientific, Pittsburgh, Pa.). This spleen suspension was pulled through an 18 gauge needle until all cells were lysed and the viscous solution was transferred to a microcentrifuge tube. The petri dish was washed with 100 µl of solution D to recover any remaining spleen. This suspension was then pulled through a 22 gauge needle an additional 5-10 times.

The sample was divided evenly between two microcentrifuge tubes and the following added, in order, with mixing by inversion after each addition: 50 µl 2 M sodium acetate pH 4.0, 0.5 ml water-saturated phenol (Fisher Scientific, Pittsburgh, Pa.), 100 µl chloroform/isoamyl alcohol 49:1 (Fisher Scientific, Pittsburgh, Pa.). The solution was vortexed for 10 sec and incubated on ice for 15 min. Following centrifugation at 14 krpm for 20 min at 2-8° C., the aqueous phase was transferred to a fresh tube. An equal volume of water saturated phenol:chloroform:isoamyl alcohol (50:49:1) was added, and the tube vortexed for ten seconds. After 15 min incubation on ice, the sample was centrifuged for 20 min at 2-8° C., and the aqueous phase transferred to a fresh tube and precipitated with an equal volume of isopropanol at −20° C. for a minimum of 30 min. Following centrifugation at 14 krpm for 20 min at 4° C., the supernatant was aspirated away, the tubes briefly spun and all traces of liquid removed from the RNA pellet.

The RNA pellets were each dissolved in 300 µl of solution D, combined, and precipitated with an equal volume of isopropanol at −20° C. for a minimum of 30 min. The sample was centrifuged 14 krpm for 20 min at 4° C., the supernatant aspirated as before, and the sample rinsed with 100 µl of ice-cold 70% ethanol. The sample was again centrifuged 14 krpm for 20 min at 4° C., the 70% ethanol solution aspirated, and the RNA pellet dried in vacuo. The pellet was resuspended in 100 µl of sterile diethyl pyrocarbonate-treated water. The concentration was determined by A260 using an absorbance of 1.0 for a concentration of 40 µg/ml. The RNAs were stored at −80° C.

Preparation of Complementary DNA (cDNA)

The total RNA purified from mouse spleens as described above was used directly as template for cDNA preparation. RNA (50 µg) was diluted to 100 µL with sterile water, and 10 µL of 130 ng/µL oligo dT12 (synthesized on Applied Biosystems Model 392 DNA synthesizer) was added. The sample was heated for 10 min at 70° C., then cooled on ice. Forty µL 5* first strand buffer was added (Gibco/BRL, Gaithersburg, Md.), along with 20 µL 0.1 M dithiothreitol (Gibco/BRL, Gaithersburg, Md.), 10 µL 20 mM deoxynucleoside triphosphates (dNTP's, Boehringer Mannheim, Indianapolis, Ind.), and 10 µL water on ice. The sample was then incubated at 37° C. for 2 min. Ten µL reverse transcriptase (Superscript™ II, Gibco/BRL, Gaithersburg, Md.) was added and incubation was continued at 37° C. for 1 hr. The cDNA products were used directly for polymerase chain reaction (PCR).

Amplification of Antibody Genes by PCR

To amplify substantially all of the H and L chain genes using PCR, primers were chosen that corresponded to substantially all published sequences. Because the nucleotide sequences of the amino termini of H and L contain considerable diversity, 33 oligonucleotides were synthesized to serve as 5' primers for the H chains, and 29 oligonucleotides were synthesized to serve as 5' primers for the kappa L chains as described in U.S. Pat. No. 6,555,310. The constant region nucleotide sequences for each chain required only one 3' primer for the H chains and one 3' primer for the kappa L chains.

A 50 µL reaction was performed for each primer pair with 50 µmol of 5' primer, 50 µmol of 3' primer, 0.25 µL Taq DNA Polymerase (5 units/µL, Boehringer Mannheim, Indianapolis, Ind.), 3 µL cDNA (prepared as described), 5 µL 2 mM dNTP's, 5 µL 10*Taq DNA polymerase buffer with MgCl2 (Boehringer Mannheim, Indianapolis, Ind.), and $H_2O$ to 50 µL. Amplification was done using a GeneAmp® 9600 thermal cycler (Perkin Elmer, Foster City, Calif.) with the following thermocycle program: 94° C. for 1 min; 30 cycles of 94° C. for 20 sec, 55° C. for 30 sec, and 72° C. for 30 sec, 72° C. for 6 min; 4° C. The dsDNA products of the PCR process were then subjected to asymmetric PCR using only a 3' primer to generate substantially only the anti-sense strand of the target genes. A 100 µL reaction was done for each dsDNA product with 200 µmol of 3' primer, 2 µL of ds-DNA product, 0.5 µL Taq DNA Polymerase, 10 µL 2 mM dNTP's, 10 µL 10*Taq DNA polymerase buffer with MgCl$_2$ (Boehringer Mannheim, Indianapolis, Ind.), and $H_2O$ to 100 µL. The same PCR program as that described above was used to amplify the single-stranded (ss)-DNA.

Purification of Single-Stranded DNA by High Performance Liquid Chromatography and Kinasing Single-Stranded DNA The H chain ss-PCR products and the L chain single-stranded PCR products were ethanol precipitated by adding 2.5 volumes ethanol and 0.2 volumes 7.5 M ammonium acetate and incubating at −20° C. for at least 30 min. The DNA was pelleted by centrifuging in an Eppendorf centrifuge at 14 krpm for 10 min at 2-8° C. The supernatant was carefully aspirated, and the tubes were briefly spun a 2nd time. The last drop of supernatant was removed with a pipette. The DNA was dried in vacuo for 10 min on medium heat. The H chain products were pooled in 210 μL water and the L chain products were pooled separately in 210 μL water. The single-stranded DNA was purified by high performance liquid chromatography (HPLC) using a Hewlett Packard 1090 HPLC and a Gen-Pak™) FAX anion exchange column (Millipore Corp., Milford, Mass.). The gradient used to purify the single-stranded DNA is shown in Table 1, and the oven temperature was 60° C. Absorbance was monitored at 260 nm. The single-stranded DNA eluted from the HPLC was collected in 0.5 min fractions. Fractions containing single-stranded DNA were ethanol precipitated, pelleted and dried as described above. The dried DNA pellets were pooled in 200 μL sterile water.

TABLE 1

HPLC gradient for purification of ss-DNA

| Time (min) | % A | % B | % C | Flow (ml/min) |
|---|---|---|---|---|
| 0 | 70 | 30 | 0 | 0.75 |
| 2 | 40 | 60 | 0 | 0.75 |
| 17 | 15 | 85 | 0 | 0.75 |
| 18 | 0 | 100 | 0 | 0.75 |
| 23 | 0 | 100 | 0 | 0.75 |
| 24 | 0 | 0 | 100 | 0.75 |
| 28 | 0 | 0 | 100 | 0.75 |
| 29 | 0 | 100 | 0 | 0.75 |
| 34 | 0 | 100 | 0 | 0.75 |
| 35 | 70 | 30 | 0 | 0.75 |

Buffer A is 25 mM Tris, 1 mM EDTA, pH 8.0
Buffer B is 25 mM Tris, 1 mM EDTA, 1 M NaCl, pH 8.0
Buffer C is 40 mm phosphoric acid The single-stranded DNA was 5'-phosphorylated in preparation for mutagenesis. Twenty-four μL 10* kinase buffer (United States Biochemical, Cleveland, Ohio), 10.4 μL 10 mM adenosine-5'-triphosphate (Boehringer Mannheim, Indianapolis, Ind.), and 2 μL polynucleotide kinase (30 units/μL, United States Biochemical, Cleveland, Ohio) was added to each sample, and the tubes were incubated at 37° C. for 1 hr. The reactions were stopped by incubating the tubes at 70° C. for 10 min. The DNA was purified with one extraction of Tris equilibrated phenol (pH>8.0, United States Biochemical, Cleveland, Ohio):chloroform:isoamyl alcohol (50:49:1) and one extraction with chloroform:isoamyl alcohol (49:1). After the extractions, the DNA was ethanol precipitated and pelleted as described above. The DNA pellets were dried, then dissolved in 50 μL sterile water. The concentration was determined by measuring the absorbance of an aliquot of the DNA at 260 nm using 33 μg/ml for an absorbance of 1.0. Samples were stored at −20° C.

Preparation of Uracil Templates Used in Generation of Spleen Antibody Phage Libraries One ml of E. coli CJ236 (BioRAD, Hercules, Calif.) overnight culture was added to 50 ml 2*YT in a 250 ml baffled shake flask. The culture was grown at 37° C. to OD600=0.6, inoculated with 10 μl of a 1/100 dilution of BS45 vector phage stock (described in U.S. Pat. No. 6,555,310) and growth continued for 6 hr. Approximately 40 ml of the culture was centrifuged at 12 krpm for 15 min at 4° C. The supernatant (30 ml) was transferred to a fresh centrifuge tube and incubated at room temperature for 15 min after the addition of 15 μl of 10 mg/ml RNaseA (Boehringer Mannheim, Indianapolis, Ind.). The phages were precipitated by the addition of 7.5 ml of 20% polyethylene glycol 8000 (Fisher Scientific, Pittsburgh, Pa.)/3.5M ammonium acetate (Sigma Chemical Co., St. Louis, Mo.) and incubation on ice for 30 min. The sample was centrifuged at 12 krpm for 15 min at 2-8° C. The supernatant was carefully discarded, and the tube briefly spun to remove all traces of supernatant. The pellet was resuspended in 400 μl of high salt buffer (300 mM NaCl, 100 mM Tris pH 8.0, 1 mM EDTA), and transferred to a 1.5 ml tube.

The phage stock was extracted repeatedly with an equal volume of equilibrated phenol:chloroform:isoamyl alcohol (50:49:1) until no trace of a white interface was visible, and then extracted with an equal volume of chloroform:isoamyl alcohol (49:1). The DNA was precipitated with 2.5 volumes of ethanol and 1/5 volume 7.5 M ammonium acetate and incubated 30 min at −20° C. The DNA was centrifuged at 14 krpm for 10 min at 4° C., the pellet washed once with cold 70% ethanol, and dried in vacuo. The uracil template DNA was dissolved in 30 μl sterile water and the concentration determined by A260 using an absorbance of 1.0 for a concentration of 40 μg/ml. The template was diluted to 250 ng/μL with sterile water, aliquoted and stored at −20° C.

Mutagenesis of Uracil Template with Ss-DNA and Electroporation into E. coli to Generate Antibody Phage Libraries Antibody phage display libraries were generated by simultaneously introducing single-stranded heavy and light chain genes onto a phage display vector uracil template. A typical mutagenesis was performed on a 2 μg scale by mixing the following in a 0.2 ml PCR reaction tube: 8 μl of (250 ng/μL) uracil template, 8 μL of 10* annealing buffer (200 mM Tris pH 7.0, 20 mM MgCl2, 500 mM NaCl), 3.33 μl of kinased single-stranded heavy chain insert (100 ng/μL), 3.1 μl of kinased single-stranded light chain insert (100 ng/μL), and sterile water to 80 μl. DNA was annealed in a GeneAmp® 9600 thermal cycler using the following thermal profile: 20 sec at 94° C., 85° C. for 60 sec, 85° C. to 55° C. ramp over 30 min, hold at 55° C. for 15 min. The DNA was transferred to ice after the program finished. The extension/ligation was carried out by adding 8 μl of 10* synthesis buffer (5 mM each dNTP, 10 mM ATP, 100 mM Tris pH 7.4, 50 mM MgCl2, 20 mM DTT), 8 μL T4 DNA ligase (1 U/μL, Boehringer Mannheim, Indianapolis, Ind.), 8 μL diluted T7 DNA polymerase (1 U/μL, New England BioLabs, Beverly, Mass.) and incubating at 37° C. for 30 min. The reaction was stopped with 300 μL of mutagenesis stop buffer (10 mM Tris pH 8.0, 10 mM EDTA). The mutagenesis DNA was extracted once with equilibrated phenol (pH>8):chloroform:isoamyl alcohol (50:49:1), once with chloroform:isoamyl alcohol (49:1), and the DNA was ethanol precipitated at −20° C. for at least 30 min. The DNA was pelleted and the supernatant carefully removed as described above. The sample was briefly spun again and all traces of ethanol removed with a pipetman. The pellet was dried in vacuo. The DNA was resuspended in 4 μL of sterile water.

One μL of mutagenesis DNA (500 ng) was transferred into 40 μl electrocompetent E. coli DH12S (Gibco/BRL, Gaithersburg, Md.) using electroporation. The transformed cells were mixed with approximately 1.0 ml of overnight XL-1 cells which were diluted with 2*YT broth to 60% the original volume. This mixture was then transferred to a 15-ml sterile culture tube and 9 ml of top agar added for plating on a 150-mm LB agar plate. Plates were incubated for 4 hr at 37° C. and then transferred to 20° C. overnight. First round antibody phage were made by eluting phage off these plates in 10 ml of 2*YT, spinning out debris, and taking the supernatant. These samples are the antibody phage display libraries used for selecting antibodies against the BST1. Efficiency of the electroporations was measured by plating 10 µl of a $10^{-4}$ dilution of suspended cells on LB agar plates, follow by overnight incubation of plates at 37° C. The efficiency was calculated by multiplying the number of plaques on the $10^{-4}$ dilution plate by 106. Library electroporation efficiencies are typically greater than $1*10^7$ phages under these conditions.

Transformation of E. coli by Electroporation

Electrocompetent E. coli cells were thawed on ice. DNA was mixed with 40 L of these cells by gently pipetting the cells up and down 2-3 times, being careful not to introduce an air bubble. The cells were transferred to a Gene Pulser cuvette (0.2 cm gap, BioRAD, Hercules, Calif.) that had been cooled on ice, again being careful not to introduce an air bubble in the transfer. The cuvette was placed in the E. coli Pulser (BioRAD, Hercules, Calif.) and electroporated with the voltage set at 1.88 kV according to the manufacturer's recommendation. The transformed sample was immediately resuspended in 1 ml of 2*YT broth or 1 ml of a mixture of 400 µl 2*YT/600 µl overnight XL-1 cells and processed as procedures dictated.

Plating M13 Phage or Cells Transformed with Antibody Phage-Display Vector Mutagenesis Reaction Phage samples were added to 200 µL of an overnight culture of E. coli XL1-Blue when plating on 100 mm LB agar plates or to 600 µL of overnight cells when plating on 150 mm plates in sterile 15 ml culture tubes. After adding LB top agar (3 ml for 100 mm plates or 9 ml for 150 mm plates, top agar stored at 55° C. (see, Appendix A1, Sambrook et al., supra.), the mixture was evenly distributed on an LB agar plate that had been pre-warmed (37° C.-55° C.) to remove any excess moisture on the agar surface. The plates were cooled at room temperature until the top agar solidified. The plates were inverted and incubated at 37° C. as indicated.

Preparation of Biotinylated ADP-Ribosyl Cyclase 2 and Biotinylated Antibodies

The concentrated recombinant BST1 antigen (full length extracellular domain) was extensively dialyzed into BBS (20 mM borate, 150 mM NaCl, 0.1% NaN$_3$, pH 8.0). After dialysis, 1 mg of the BST1 (1 mg/ml in BBS) was reacted with a 15 fold molar excess of biotin-XX-NHS ester (Molecular Probes, Eugene, Oreg., stock solution at 40 mM in DMSO). The reaction was incubated at room temperature for 90 min and then quenched with taurine (Sigma Chemical Co., St. Louis, Mo.) at a final concentration of 20 mM. The biotinylation reaction mixture was then dialyzed against BBS at 2-8° C. After dialysis, the biotinylated BST1 was diluted in panning buffer (40 mM Tris, 150 mM NaCl, 20 mg/ml BSA, 0.1% Tween 20, pH 7.5), aliquoted, and stored at −80° C. until needed.

Antibodies were reacted with 3-(N-maleimidylpropionyl) biocytin (Molecular Probes, Eugene, Oreg.) using a free cysteine located at the carboxy terminus of the heavy chain. Antibodies were reduced by adding DTT to a final concentration of 1 mM for 30 min at room temperature. Reduced antibody was passed through a Sephadex® G50 desalting column equilibrated in 50 mM potassium phosphate, 10 mM boric acid, 150 mM NaCl, pH 7.0. 3-(N-maleimidylpropionyl)-biocytin was added to a final concentration of 1 mM and the reaction allowed to proceed at room temperature for 60 min. Samples were then dialyzed extensively against BBS and stored at 2-8° C.

Preparation of Avidin Magnetic Latex

The magnetic latex (Estapor, 10% solids, Bangs Laboratories, Fishers, Ind.) was thoroughly resuspended and 2 ml aliquoted into a 15 ml conical tube. The magnetic latex was suspended in 12 ml distilled water and separated from the solution for 10 min using a magnet (PerSeptive Biosystems, Framingham, Mass.). While maintaining the separation of the magnetic latex with the magnet, the liquid was carefully removed using a 10 ml sterile pipette. This washing process was repeated an additional three times. After the final wash, the latex was resuspended in 2 ml of distilled water. In a separate 50 ml conical tube, 10 mg of avidin-HS (NeutrAvidin, Pierce, Rockford, Ill.) was dissolved in 18 ml of 40 mM Tris, 0.15 M sodium chloride, pH 7.5 (TBS). While vortexing, the 2 ml of washed magnetic latex was added to the diluted avidin-HS and the mixture mixed an additional 30 sec. This mixture was incubated at 45° C. for 2 hr, shaking every 30 min. The avidin magnetic latex was separated from the solution using a magnet and washed three times with 20 ml BBS as described above. After the final wash, the latex was resuspended in 10 ml BBS and stored at 4° C.

Immediately prior to use, the avidin magnetic latex was equilibrated in panning buffer (40 mM Tris, 150 mM NaCl, 20 mg/ml BSA, 0.1% Tween 20, pH 7.5). The avidin magnetic latex needed for a panning experiment (200 µl/sample) was added to a sterile 15 ml centrifuge tube and brought to 10 ml with panning buffer. The tube was placed on the magnet for 10 min to separate the latex. The solution was carefully removed with a 10 ml sterile pipette as described above. The magnetic latex was resuspended in 10 ml of panning buffer to begin the second wash. The magnetic latex was washed a total of 3 times with panning buffer. After the final wash, the latex was resuspended in panning buffer to the starting volume.

Example 2: Selection of Recombinant Polyclonal Antibodies to BST1 Antigen

Binding reagents that specifically bind to the BST1 were selected from the phage display libraries created from hyperimmunized mice as described in Example 1.

Panning

First round antibody phage were prepared as described in Example 1 using BS45 uracil template. Electroporations of mutagenesis DNA were performed yielding phage samples derived from different immunized mice. To create more diversity in the recombinant polyclonal library, each phage sample was panned separately.

Before the first round of functional panning with the biotinylated BST1 antigen, antibody phage libraries were selected for phage displaying both heavy and light chains on their surface by panning with 7F11-magnetic latex (as described in Examples 21 and 22 of U.S. Pat. No. 6,555, 310). Functional panning of these enriched libraries was performed in principle as described in Example 16 of U.S. Pat. No. 6,555,310. Specifically, 10 µL of $1*10^{-6}$ M biotinylated BST1 antigen was added to the phage samples (approximately 1*10$^{-8}$ M final concentration of the BST1), and the mixture allowed to come to equilibrium overnight at 2-8° C.

After reaching equilibrium, samples were panned with avidin magnetic latex to capture antibody phage bound to the BST1. Equilibrated avidin magnetic latex (Example 1), 200 µL latex per sample, was incubated with the phage for 10 min at room temperature. After 10 min, approximately 9 ml of panning buffer was added to each phage sample, and the magnetic latex separated from the solution using a magnet. After a ten minute separation, unbound phage was carefully removed using a 10 ml sterile pipette. The magnetic latex was then resuspended in 10 ml of panning buffer to begin the second wash. The latex was washed a total of three times as described above. For each wash, the tubes were in contact with the magnet for 10 min to separate unbound phage from the magnetic latex. After the third wash, the magnetic latex was resuspended in 1 ml of panning buffer and transferred to a 1.5 mL tube. The entire volume of magnetic latex for each sample was then collected and resuspended in 200 µl 2*YT and plated on 150 mm LB plates as described in Example 1 to amplify bound phage. Plates were incubated at 37° C. for 4 hr, then overnight at 20° C.

The 150 mm plates used to amplify bound phage were used to generate the next round of antibody phage. After the overnight incubation, second round antibody phage were eluted from the 150 mm plates by pipetting 10 mL of 2*YT media onto the lawn and gently shaking the plate at room temperature for 20 min. The phage samples were then transferred to 15 ml disposable sterile centrifuge tubes with a plug seal cap, and the debris from the LB plate pelleted by centrifuging the tubes for 15 min at 3500 rpm. The supernatant containing the second round antibody phage was then transferred to a new tube.

A second round of functional panning was set up by diluting 100 µL of each phage stock into 900 µL of panning buffer in 15 ml disposable sterile centrifuge tubes. The biotinylated BST1 antigen was then added to each sample as described for the first round of panning, and the phage samples incubated for 1 hr at room temperature. The phage samples were then panned with avidin magnetic latex as described above. The progress of panning was monitored at this point by plating aliquots of each latex sample on 100 mm LB agar plates to determine the percentage of kappa positives. The majority of latex from each panning (99%) was plated on 150 mm LB agar plates to amplify the phage bound to the latex. The 100 mm LB agar plates were incubated at 37° C. for 6-7 hr, after which the plates were transferred to room temperature and nitrocellulose filters (pore size 0.45 mm, BA85 Protran, Schleicher and Schuell, Keene, N.H.) were overlaid onto the plaques.

Plates with nitrocellulose filters were incubated overnight at room temperature and then developed with a goat anti-mouse kappa alkaline phosphatase conjugate to determine the percentage of kappa positives as described below. Phage samples with lower percentages (<70%) of kappa positives in the population were subjected to a round of panning with 7F11-magnetic latex before performing a third functional round of panning overnight at 2-8° C. using the biotinylated BST1 antigen at approximately 2*10$^{-9}$ M. This round of panning was also monitored for kappa positives. Individual phage samples that had kappa positive percentages greater than 80% were pooled and subjected to a final round of panning overnight at 2-8° C. at 5*10$^{-9}$ M. The BST1 antibody genes contained within the eluted phage from this fourth round of functional panning were subcloned into the expression vector, pBRncoH3.

The subcloning process was done generally as described in Example 18 of U.S. Pat. No. 6,555,310. After subcloning, the expression vector was electroporated into DH10B cells and the mixture grown overnight in 2*YT containing 1% glycerol and 10 µg/ml tetracycline. After a second round of growth and selection in tetracycline, aliquots of cells were frozen at −80° C. as the source for the BST1 polyclonal antibody production. Monoclonal antibodies were selected from these polyclonal mixtures by plating a sample of the mixture on LB agar plates containing 10 µg/ml tetracycline and screening for antibodies that recognized the BST1.

Expression and Purification of Recombinant Antibodies Against ADP-Ribosyl Cyclase 2

A shake flask inoculum was generated overnight from a −70° C. cell bank in an Innova 4330 incubator shaker (New Brunswick Scientific, Edison, N.J.) set at 37° C., 300 rpm. The inoculum was used to seed a 20 L fermentor (Applikon, Foster City, Calif.) containing defined culture medium [Pack et al. (1993) Bio/Technology 11: 1271-1277] supplemented with 3 g/L L-leucine, 3 g/L L-isoleucine, 12 g/L casein digest (Difco, Detroit, Mich.), 12.5 g/L glycerol and 10 µg/ml tetracycline. The temperature, pH and dissolved oxygen in the fermentor were controlled at 26° C., 6.0-6.8 and 25% saturation, respectively. Foam was controlled by addition of polypropylene glycol (Dow, Midland, Mich.). Glycerol was added to the fermentor in a fed-batch mode. Fab expression was induced by addition of L(+)-arabinose (Sigma, St. Louis, Mo.) to 2 g/L during the late logarithmic growth phase. Cell density was measured by optical density at 600 nm in an UV-1201 spectrophotometer (Shimadzu, Columbia, Md.). Following run termination and adjustment of pH to 6.0, the culture was passed twice through an M-210B-EH Microfluidizer (Microfluidics, Newton, Mass.) at 17,000 psi. The high pressure homogenization of the cells released the Fab into the culture supernatant.

The first step in purification was expanded bed immobilized metal affinity chromatography (EB-IMAC). Streamline™ chelating resin (Pharmacia, Piscataway, N.J.) was charged with 0.1 M NiCl$_2$ and was then expanded and equilibrated in 50 mM acetate, 200 mM NaCl, 10 mM imidazole, 0.01% NaN$_3$, pH 6.0 buffer flowing in the upward direction. A stock solution was used to bring the culture homogenate to 10 mM imidazole, following which it was diluted two-fold or higher in equilibration buffer to reduce the wet solids content to less than 5% by weight. It was then loaded onto the Streamline column flowing in the upward direction at a superficial velocity of 300 cm/hr. The cell debris passed through unhindered, but the Fab was captured by means of the high affinity interaction between nickel and the hexahistidine tag on the Fab heavy chain. After washing, the expanded bed was converted to a packed bed and the Fab was eluted with 20 mM borate, 150 mM NaCl, 200 mM imidazole, 0.01% NaN$_3$, pH 8.0 buffer flowing in the downward direction.

The second step in the purification used ion-exchange chromatography (IEC). Q Sepharose® FastFlow resin (Pharmacia, Piscataway, N.J.) was equilibrated in 20 mM borate, 37.5 mM NaCl, 0.01% NaN3, pH 8.0. The Fab elution pool from the EB-IMAC step was diluted four-fold in 20 mM borate, 0.01% NaN3, pH 8.0 and loaded onto the IEC column. After washing, the Fab was eluted with a 37.5-200 mM NaCl salt gradient. The elution fractions were evaluated for purity using an Xcell II™ SDS-PAGE system (Novex, San Diego, Calif.) prior to pooling. Finally, the Fab pool was concentrated and diafiltered into 20 mM borate, 150 mM NaCl, 0.01% NaN₃, pH 8.0 buffer for storage. This was achieved in a Sartocon Slice™ system fitted with a 10,000 MWCO cassette (Sartorius, Bohemia, N.Y.). The final purification yields were typically 50%. The concentration of the purified Fab was measured by UV absorbance at 280 nm, assuming an absorbance of 1.6 for a 1 mg/ml solution.

Example 3: Specificity of Monoclonal Antibodies to BST1 Determined by Flow Cytometry Analysis The specificity of antibodies against the BST1 selected in Example 2 was tested by flow cytometry. To test the ability of the antibodies to bind to the cell surface BST1 protein, the antibodies were incubated with the BST1-expressing cells, A549 and H226, from human lung adenocarcinoma and human lung squamous carcinoma, respectively. Cells were washed in FACS buffer (DPBS, 2% FBS), centrifuged and resuspended in 100 µl of the diluted primary BST1 antibody (also diluted in FACS buffer). The antibody-A549 complex was incubated on ice for 60 min and then washed twice with FACS buffer as described above. The cell-antibody pellet was resuspended in 1000 of the diluted secondary antibody (also diluted in FACS buffer) and incubated on ice for 60 min on ice. The pellet was washed as before and resuspended in 200 µl FACS buffer. The samples were loaded onto the BD FACScanto II flow sytometer and the data analyzed using the BD FACSdiva software.

Results

Figure 3B:
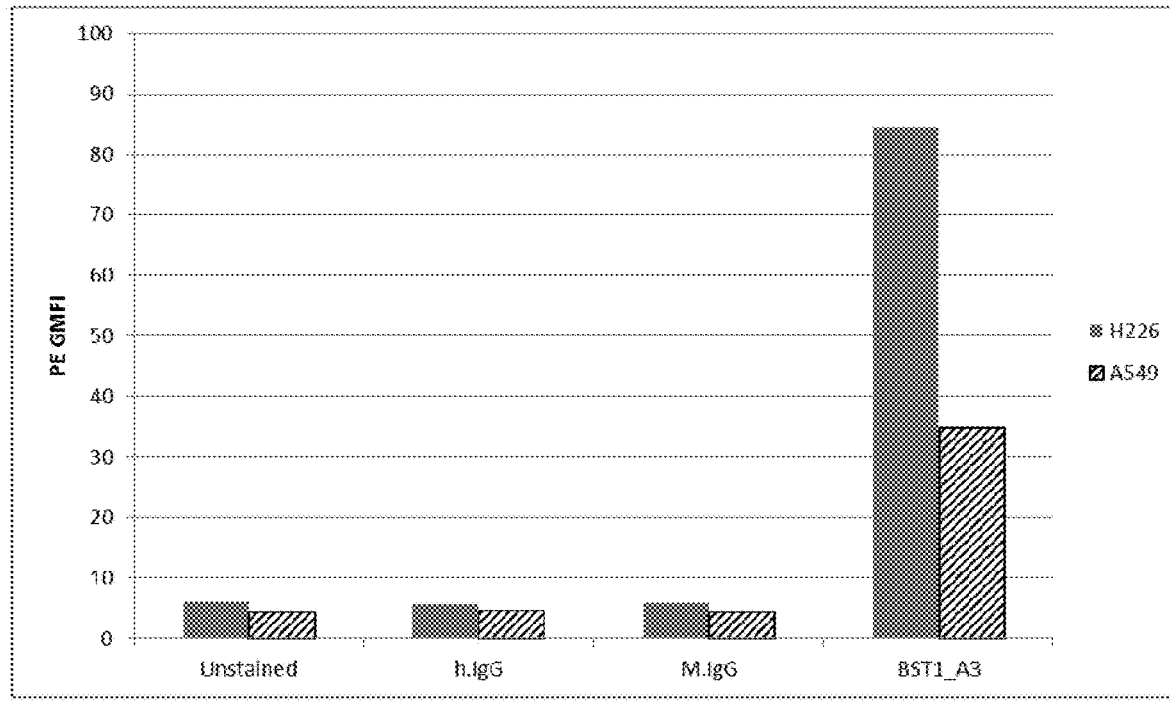

The results of the flow cytometry analysis demonstrated that 4 monoclonal antibodies designated BST1_A1, BST1_A2 and BST_A3 bound effectively to the cell-surface human BST1. FIG. 3a shows the binding specificities of both BST1_A1 and BST1_A2 to BST1 on A549 and H226 cells, respectively. FIG. 3b shows the binding specificities BST1_A3 to BST1 on A549 and H226 cells. The results indicate strong binding of those antibodies against BST1 on A549 and H226.

Example 4: Structural Characterization of Monoclonal Antibodies to BST1

The cDNA sequences encoding the heavy and light chain variable regions of the BST1_A2 and BST1_A1 monoclonal antibodies were obtained using standard PCR techniques and were sequenced using standard DNA sequencing techniques.

The antibody sequences may be mutagenized to revert back to germline residues at one or more residues.

The nucleotide and amino acid sequences of the heavy chain variable region of BST1_A2 are SEQ ID NO: 10 and 2, respectively.

The nucleotide and amino acid sequences of the light chain variable region of BST1_A2 are SEQ ID NO: 14 and 6, respectively.

Comparison of the BST1_A2 heavy chain immunoglobulin sequence to the known murine germline immunoglobulin heavy chain sequences demonstrated that the BST1_A2 heavy chain utilizes a $V_H$ segment from murine germline $V_H$ 1-39. Further analysis of the BST1_A2 $V_H$ sequence using the Kabat system of CDR region determination led to the delineation of the heavy chain CDR1, CDR2 and CDR3 regions as shown in SEQ ID NOs:38, 42 and 46, respectively. The alignments of the BST1_A2 CDR1 and CDR2 $V_H$ sequences to the germline $V_H$ 1-39 sequence are shown in FIGS. 1a and 1b.

Comparison of the BST1_A2 light chain immunoglobulin sequence to the known murine germline immunoglobulin light chain sequences demonstrated that the BST1_A2 light chain utilizes a $V_K$ segment from murine germline $V_K$ 4-55. Further analysis of the BST1_A2 $V_K$ sequence using the Kabat system of CDR region determination led to the delineation of the light chain CDR1, CDR2 and CDR3 regions as shown in SEQ ID NOs:49, 52 and 55, respectively. The alignments of the BST1_A2 CDR1, CDR2 and CDR3 $V_K$ sequences to the germline $V_K$ 4-55 sequences are shown in FIGS. 2a, 2b and 2c.

The nucleotide and amino acid sequences of the heavy chain variable region of BST1_A1 are SEQ ID NO: 9 and 1, respectively.

The nucleotide and amino acid sequences of the light chain variable region of BST1_A1 are SEQ ID NO: 13 and 5, respectively.

Comparison of the BST1_A1 heavy chain immunoglobulin sequence to the known murine germline immunoglobulin heavy chain sequences demonstrated that the BST1_A1 heavy chain utilizes a $V_H$ segment from murine germline $V_H$ 1-80. Further analysis of the BST1_A1 $V_H$ sequence using the Kabat system of CDR region determination led to the delineation of the heavy chain CDR1, CDR2 and CDR3 regions as shown in SEQ ID NOs:37, 41 and 45, respectively. The alignments of the BST1_A1 CDR1 and CDR2 $V_H$ sequences to the germline $V_H$ 1-80 sequence are shown in FIGS. 1a and 1b.

Comparison of the BST1_A1 light chain immunoglobulin sequence to the known murine germline immunoglobulin light chain sequences demonstrated that the BST1_A1 light chain utilizes a $V_K$ segment from murine germline $V_K$ 4-74. Further analysis of the BST1_A1 $V_K$ sequence using the Kabat system of CDR region determination led to the delineation of the light chain CDR1, CDR2 and CDR3 regions as shown in SEQ ID NOs:48, 51 and 54, respectively. The alignments of the BST1_A1 CDR1, CDR2 and CDR3 $V_K$ sequences to the germline $V_K$ 4-74 sequences are shown in FIGS. 2a, 2b and 2c.

The nucleotide and amino acid sequences of the heavy chain variable region of BST1_A3 are SEQ ID NO: 54 and 52, respectively.

The nucleotide and amino acid sequences of the light chain variable region of BST1_A3 are SEQ ID NO: 55 and 53, respectively.

Comparison of the BST1_A3 heavy chain immunoglobulin sequence to the known murine germline immunoglobulin heavy chain sequences demonstrated that the BST1_A3 heavy chain utilizes a $V_H$ segment from murine $V_H$ germline 69-1. Further analysis of the BST1_A3 $V_H$ sequence using the Kabat system of CDR region determination led to the delineation of the heavy chain CDR1, CDR2 and CDR3 regions as shown in SEQ ID NOs: 56, 57 and 58, respectively. The alignments of the BST1_A3 CDR1 and CDR2 $V_H$ sequences to the murine $V_H$ germline 69-1 sequence are shown in FIGS. 1a and 1b.

Comparison of the BST1_A3 light chain immunoglobulin sequence to the known murine germline immunoglobulin light chain sequences demonstrated that the BST1_A3 light chain utilizes a $V_K$ segment from murine $V_K$ germline 44-1. Further analysis of the BST1_A3 $V_K$ sequence using the Kabat system of CDR region determination led to the delineation of the light chain CDR1, CDR2 and CDR3 regions as shown in SEQ ID NOs: 59, 60 and 61, respectively. The alignments of the BST1_A3 CDR1, CDR2 and CDR3 $V_K$ sequences to the murine $V_K$ germline 44-1 sequences are shown in FIGS. 2a, 2b and 2c.

Example 5: Internalization and MabZAP of BST1_A1 and BST1_A2 in A549 and H226 Cells Internalization of BST1_A1 and BST1_A2 by H226 and A549 were investigated using a MabZap assay. The MabZAP assay showed internalization of the anti-BST1 monoclonal antibodies through binding of an anti-human IgG secondary antibody conjugated to the toxin saporin. (Advanced Targeting System, San Diego, Calif., IT-22-100). First, BST1 Fab was bound to the surface of the cells. Then, the MabZAP antibodies were bound to the primary antibodies. Next, the MabZAP complex was internalized by the cells. The entrance of Saporin into the cells resulted in protein synthesis inhibition and eventual cell death.

The MabZAP assay was conducted as follows. Each of the cells was seeded at a density of 5×103 cells per well. The anti-BST1 monoclonal antibody or an isotype control human IgG was serially diluted then added to the cells and incubated for 15 min at 25° C. The MabZAP was then added and incubated for 72 hr at 37° C. Cell viability in the plates was detected by CellTiter-Glo® Luminescent Cell Viability Assay kit (Promega, G7571) and the plates were read and analysed using Promega Glomax. Cell death was proportional to the concentration of anti-BST1 monoclonal antibodies.

Figure 4A:
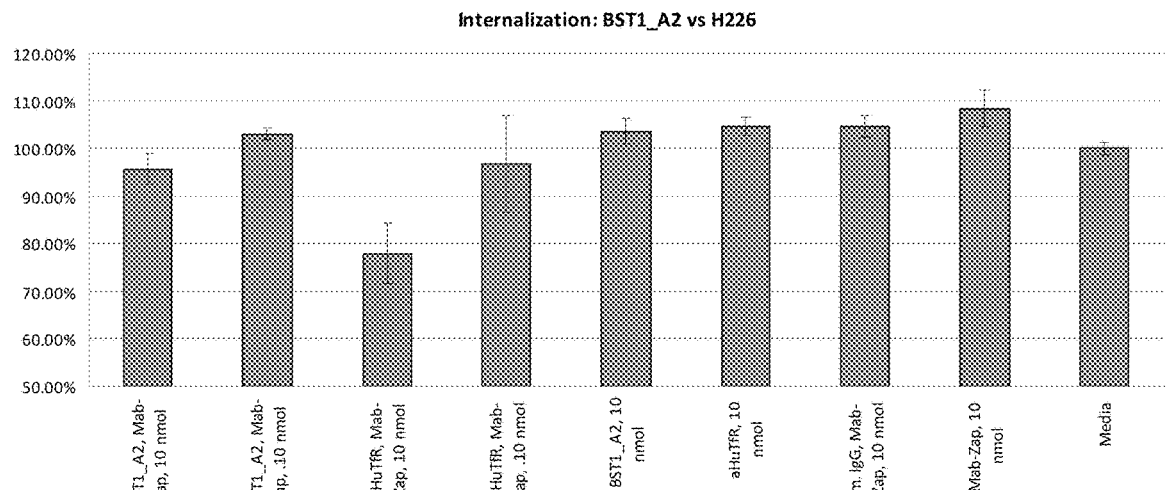
FIGS. 4A and 4B show the internalization of anti-BST1 monoclonal antibodies by A549 and H226 cells, using MabZAP assay.
Figure 4B:
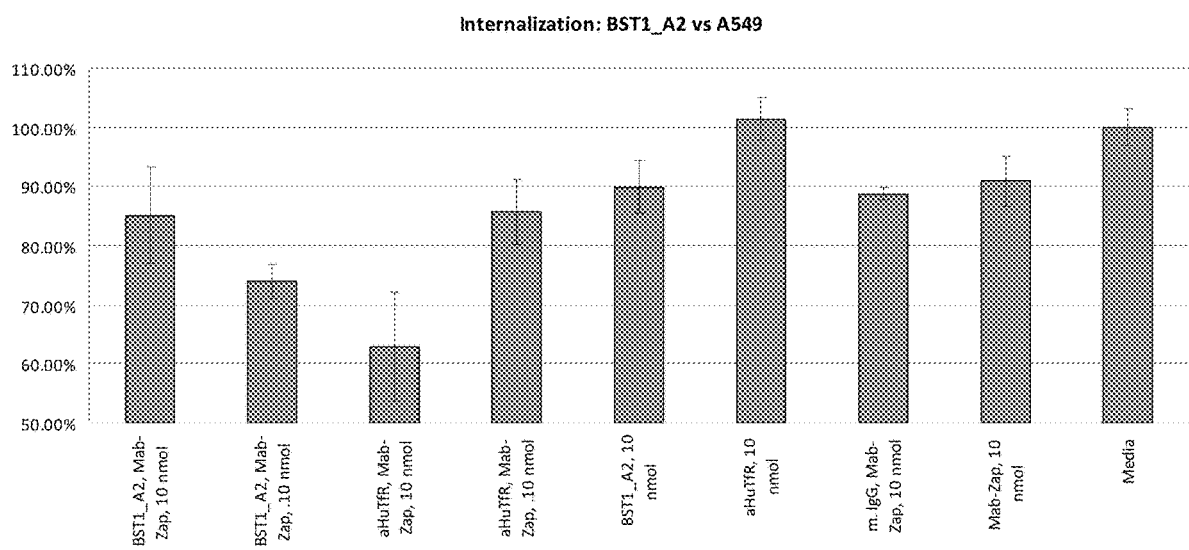

FIGS. 4a and 4b show that the anti-BST1 monoclonal antibodies, BST1_A1 and BST1_A2 were internalized by and induced approximately 20% cell kill at 10 nmol/L of H226 and A549 cells, as compared to the anti-human IgG isotype control antibody. The results show BST1_A1 and BST1_A2 can be internalized at low levels and can induce cell kill at high concentrations when coupled with a toxin.

Example 6: Humanization of BST1_A2

To design humanized sequences of BST1_A2 $V_H$ and $V_L$, the framework amino acids important for the formation of the CDR structure were identified using the three-dimensional model. Human $V_H$ and $V_L$, sequences with high homologies with BST1_A2 were also selected from the GenBank database. The CDR sequences together with the identified framework amino acid residues were grafted from BST1_A2 to the human framework sequences (FIGS. 5-7).

Example 7 Antibody-Dependent Cellular Cytotoxicity Mediated by Anti-BST1 mAbs Firstly 25 μl of parental and Non-Fucosylated anti-BST1 antibodies (BST1_A2 and BST1_A2_NF) at concentrations ranging from 10 nm/L to 0.1 nm/L were added to separate wells of a v bottom 96 well plate along with 50 μl of BST1-expressing A549 and U937 cells. 25 μl of Effector cells was then added to the wells to yield final effector:target (E:T) ratio of 10:1 and 25:1. The plate was then gently spun at 1000 rpm for 2 minutes, afterwhich it was incubated for 4 hrs in 37° C., 5% CO2 incubator. At 3 hrs post incubation, 10 μl of lysis solution was added to each of the wells containing BST1-expressing cells alone to measure maximum LDH release, and one set of wells containing media alone for volume correction control.

After the incubation, the cells were spun gently at 1000 rpm for 2 minutes, afterwhich 50 μl of supernatant was transferred to a flat bottom 96 well plate. Using the CytoTox 96® Non-Radioactive Cytotoxicity Assay available from Promega (Cat #: G1780), kit components were reconstituted according to manufacturer's specifications and 50 μl of the substrate mix was then added to each well. The plate was then covered and left to incubate for 30 minutes at 25° C. protected from light. Following this, 50 μl of Stop Solution was added to each well and the absorbance was recorded at 490 nm using the varioskan plate reader.

Figure 8A:
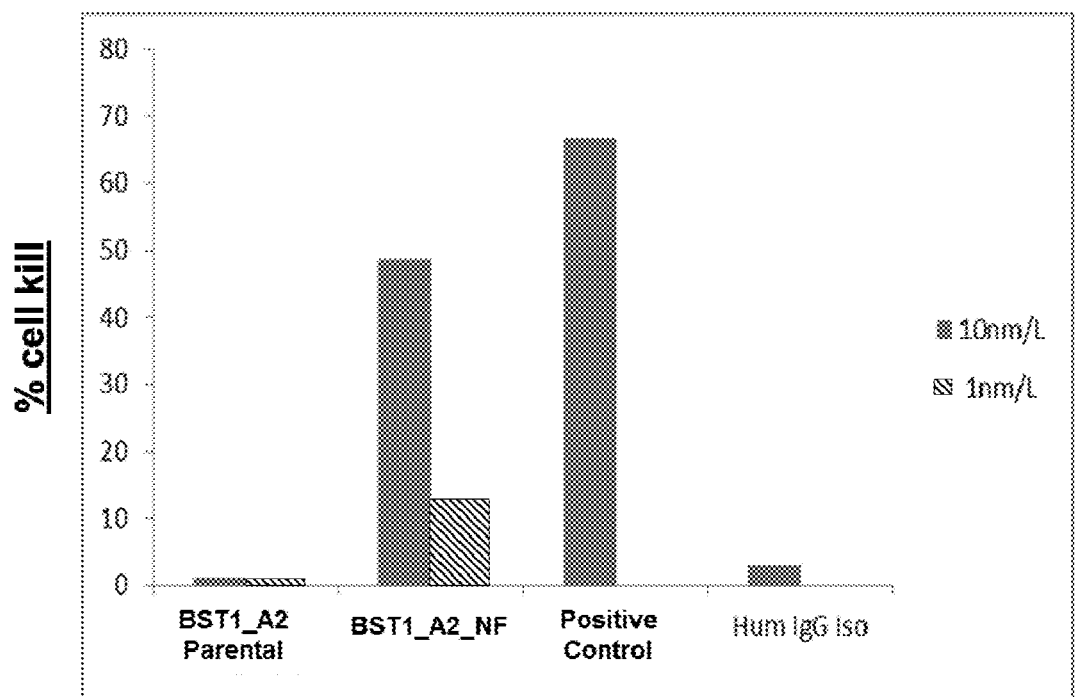
FIGS. 8A and 8B show BST1_A2 and BST1_A2_NF eliciting an antibody dependent cellular cytotoxicity (ADCC) response in the presence of effector cells.
Figure 8B:
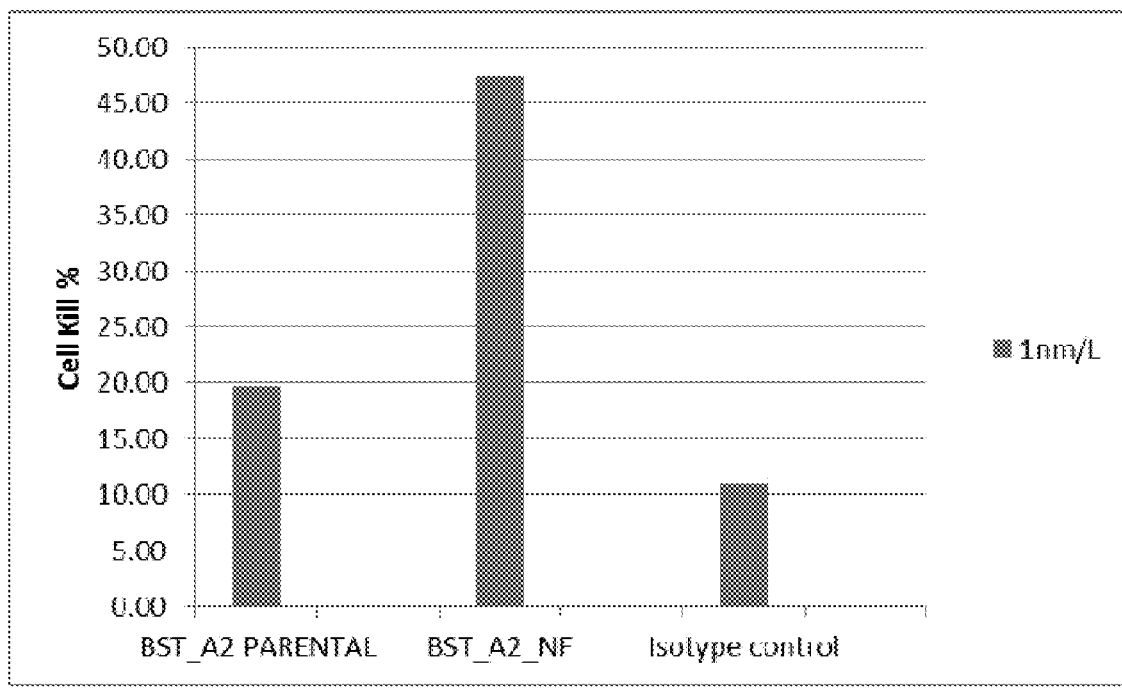

Using an antibody known to incite cell-kill via ADCC as a positive control and a human IgG1 isotype control as a negative control, the results show BST1_A2 and BST1_A2_NF were capable of eliciting ADCC on BST1-expressing A549 and U937 cells. On BST1-expressing A549 cells, BST1_A2_NF were shown to approximately 45% killing at 10 nmol/L (FIG. 8a). On BST1-expressing U937 cells, BST1_A2 were shown to approximately 20% killing at 1 nmol/L and BST1_A2_NF were shown to approximately 45% killing at 1 nmol/L (FIG. 8b).

Example 8: Specificity of Monoclonal Antibodies to BST1 Determined by Flow Cytometry Analysis in AML Patients The ability of BST_A2 to bind to lymphoblasts from patients with AML was tested by Flow Cytometry Analysis. Blood was taken from 20 AML patients. Using the procedure as described in the Example 3, BST_A2 was shown to bind to AML blasts of approx. 80% of the AML patients.

Example 9: Immunohistochemistry Using BST1_A2_NF on Normal Tissue

BST1_A2_NF (Oxford BioTherapeutics, Lot 04302012), or an isotype control antibody were diluted in SFPB (Dako, Carpinteria, Calif., X0909) to obtain a 20 μg/mL solution. The secondary antibody, goat anti-human immunoglobulin G (IgG) antigen-binding fragment (Fab) fluorescein isothiocyanate (FITC)-conjugated (Jackson Immunoresearch, West Grove, Pa., 109-097-003), was similarly diluted to obtain a 20 μg/mL solution Primary and secondary antibodies were combined (50 μL each) in a labeled tube, gently mixed, and incubated for 3 minutes at room temperature, resulting in a primary antibody concentration of 10 μg/mL. This mixture was diluted 1:5 with SFPB, gently mixed, and incubated for 30 minutes at room temperature, resulting in a primary antibody concentration of 1 μg/mL.

Slides

During the above incubations, the pre-fixed, frozen normal tissue array slide (Biochain Institute, Newark, Calif., T6234700), containing 20 types of normal human organ tissue (adrenal, ovary, pancreas, thyroid, brain cerebrum, brain cerebellum, lung, spleen, uterus, cervix, breast, placenta, heart, skin, skeletal muscle, kidney, stomach, small intestine, liver, salivary gland), and the FF H226 (ATCC, Manassas, Va., CRL-5826) cell pellet sections (Biochain Institute, Newark, Calif.) were removed from the freezer (−80° C.) and allowed to thaw at room temperature for 20 minutes. The H226 slides were fixed for 10 min in ice cold acetone and allowed to dry at room temperature for 15 min. Both slides were then washed 3 times in Dulbecco's phosphate-buffered saline (DPBS, Thermo Scientific, Waltham Va., SH30028-03) for 5 minutes each washed, labeled, and the tissue was circled with a hydrophobic-barrier pen.

Endogenous peroxidase activity was inhibited by incubating the slides with peroxidase suppressor solution (Thermo Scientific, 35000) for 10 minutes. The slides were then washed once in DPBS, and once in DPBS containing 0.125% Tween-20 v/v (DPBS-T, Fisher Scientific, Hampton, N.H., BP337-100) for 3 minutes each.

Staining Complexes

To produce the final staining complexes, a 10 μg/μL solution of human IgG (Chrome pure human IgG, whole molecule, Jackson Immunoresearch, 09-000-003) was prepared in SFPB and equal volume added to the primary/secondary antibody mixture. This combination was gently mixed and incubated at room temperature for 30 minutes, resulting in a final primary antibody concentration of 1 μg/mL.

Immunolabeling

While the staining complexes were incubating, nonspecific binding sites on the tissues were blocked by incubating the slides in SFPB for 30 minutes at room temperature in a humidified chamber. Afterwards, the blocking solution was removed and the staining complexes were added to the tissue for 30 minutes at room temperature in a humidified chamber. The staining complexes were then removed and the slides were washed once in DPBS and once in DPBS-T for 3 minutes each.

The tertiary antibody (mouse anti-FITC, Abcam, Cambridge, Mass., ab10257) was diluted to a concentration of 2 μg/mL in SFPB and applied to the slides for 30 minutes at room temperature in a humidified chamber. The tertiary antibody was removed and the slides were washed once in DPBS and once in DPBS-T for 3 minutes each.

The quaternary antibody (Dual Link EnVision+ HRP-conjugated polymer, Mouse and Rabbit Dako, K4063) was applied to the slides for 30 minutes at room temperature in a humidified chamber. The slides were washed once in DPBS and once in DPBS-T for 3 minutes each.

To develop the slides, DAB chromogen (Invitrogen, Grand Island, N.Y., 882014) was prepared according to manufacturer instructions and applied to the slides for 10 minutes at room temperature. The DAB reagent was removed to toxic waste and the slides were washed in tap water. The slides were washed in DPBS for 3 min and then counterstained by a 30 second incubation in Harris hematoxylin (Fisher, 23-245-677). The hematoxylin was removed to waste and the slides were washed in running tap water for 2 minutes and allowed to dry at room temperature. Cover slips were mounted with Faramount mounting media (Dako, 5302580) and the staining was analyzed under light microscopy.

Results

FF H226 cell pellets and normal human tissues were assayed by IHC with BST1_A2_NF for expression of BST1. Normal human tissues assayed by IHC included adrenal, ovary, pancreas, thyroid, cerebrum, cerebellum, lung, spleen, uterus, cervix, breast, placenta, heart, skin, skeletal muscle, kidney, stomach, small intestine salivary gland and liver. H226 cells (known to express BST1) were used as a positive control for binding. Human IgG was used as a negative control antibody. H226 cell pellets stained specifically for BST1. Staining can be seen in the cell cytoplasm, and also at the cell membrane on some cells. In contrast, specific BST1 staining was largely absent from an array of FF normal human tissues.

Example 10: Antibody-Dependent Cellular Cytotoxicity Mediated by BST1_A2_NF Using NK Cells from AML Patients The ADCC activity of BST1_A2_NF was investigated using the AML cell line U937 positive for expression of BST1 and comparing effector cells from healthy donors and AML patients.

Target cells were labelled with $^{51}$Cr (~50 μCi) for 90 minutes at 37° C. NK cells were isolated from healthy donor and AML patient PBMCs by CD56 positive selection (NK-cell Isolation Kit; MACS Miltenyi Biotech) and added to the target cells at different E:T Ratios (50:1 to 6.25:1) in triplicates. Antibody was added at a final concentration of 10 μg/ml. Target cells and NK cells without antibody served as negative control. ADCC on RAJI cells mediated by Rituximab and NK cells from the same healthy donor and AML patient served as positive control. Spontaneous Lysis ($^{51}$CR labelled U937 cells without NK-cells and antibody) and Maximum Lysis ($^{51}$CR labelled U937 cells directly on measurement plate) were determined in sextuplicates. After 4 hours incubation at 37° C., supernatants were transferred to the measurement plate (Lumaplate), dried over night and analyzed using a TOPCount (Perkin Elmer) reader. Data were analyzed using the Graphpad PRISM Software Version 4.0.

Results

Figure 9A:
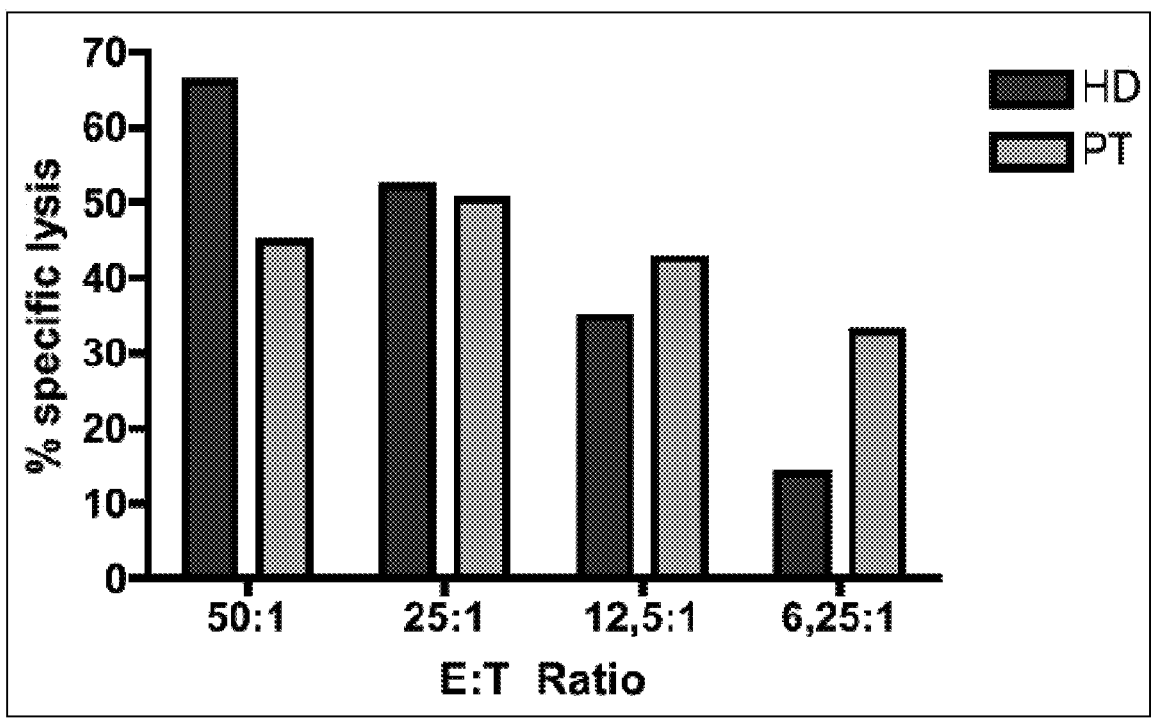
FIG. 9A depicts BST1_A2_NF eliciting an antibody dependent cellular cytotoxicity (ADCC) response against U937 cells in the presence of NK cells isolated from patients with AML and healthy donors.
Figure 9B:
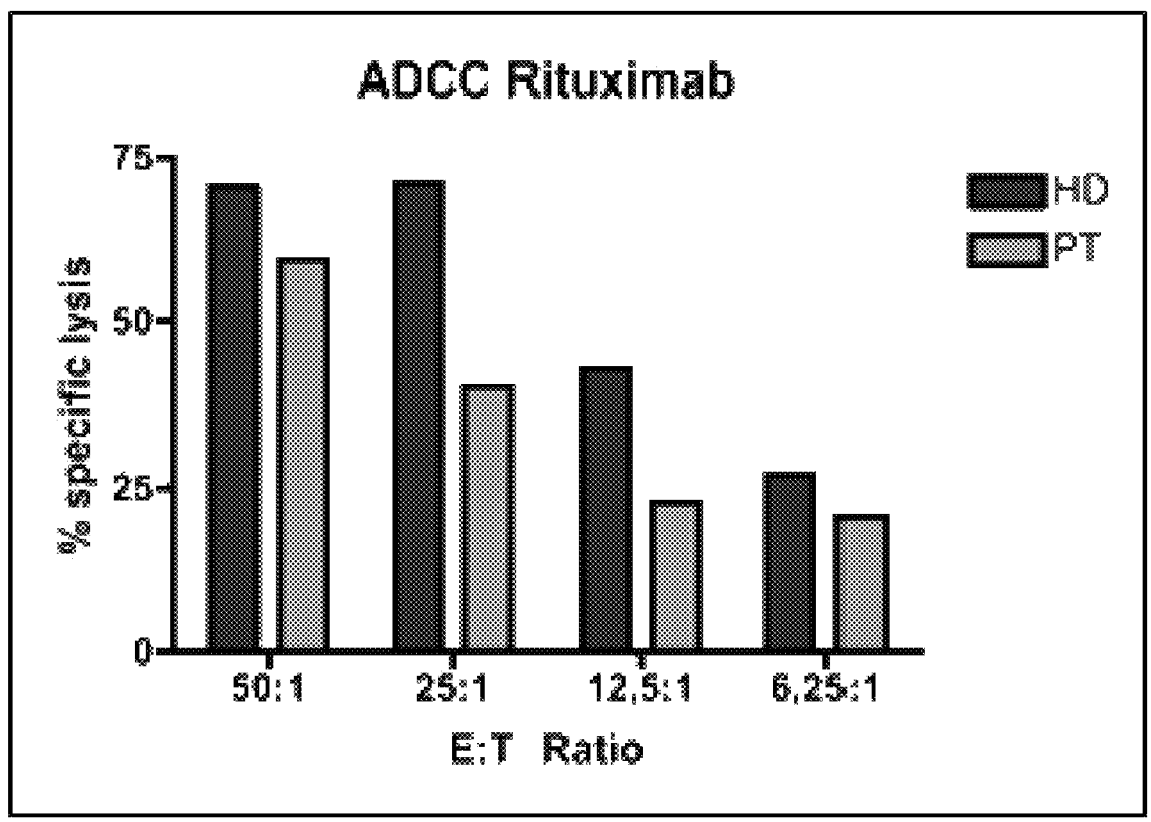
FIG. 9B depicts Rituximab eliciting an antibody dependent cellular cytotoxicity (ADCC) response against RAJI cells in the presence of NK cells isolated from patients with AML and healthy donors.

As shown in FIG. 9a, NK cells from AML patients are shown to be highly effective in ADCC lysis of U937 cells, comparable to NK cells from a healthy donor using BST1_A2_NF at 10 μg/ml antibody concentration. FIG. 9b shows NK cells from AML patients also appeared to be highly effective in ADCC lysis of RAJI cells using Rituximab, although less active than NK cells from healthy donors. The results show BST1_A2_NF would have a therapeutic effect in AML patients.

Example 11: Antibody-Dependent Cell-Mediated Cytotoxicity of BST1_A2_NF Against Monocytes Blood from 5 healthy donors, obtained as buffy coat from the Stanford University Blood Bank (Palo Alto Calif.) was processed using Ficoll-Paque™ Plus density gradient medium (Amersham Biosciences, Uppsala, Sweden). Isolated PBMCs were washed twice with phosphate-buffered saline (PBS), and red blood cells (RBCs) were lysed with 1×RBC Lysis Buffer (eBioscience, San Diego Calif.) according to manufacturer instructions. PBMCs were washed twice more with PBS after quenching the lysed cells with 10% fetal bovine serum (FBS). PBMCs were then resuspended in 30 mL each PBS, counted, spun down, and resuspended at 250,000 cells/100 μL Roswell Park Memorial Institute (RPMI) medium plus sodium pyruvate, glutamine, and Pen Strep (penicillin streptomycin, Invitrogen); FBS was added to a final concentration of 10%.

BST1_A2_NF antibody was added in triplicate, starting at a concentration of 5 μg/mL and diluted serially by 1:3-fold. Another non-fucosylated antibody (6g11NF) and its parental form (6g11P) were included as negative controls. The target antigen for 6g11 is not expressed on monocytes. Other control wells included PBMCs alone. Plates were placed in a 5% humidified carbon dioxide incubator (standard tissue culture conditions) for 15 to 20 hours. After the overnight incubation, triplicates were combined into a single sample for each condition. Cells were spun for 5 minutes at 1000×g, resuspended in FACS buffer, washed, spun down, and resuspended in 100 μL FACS buffer and placed on ice. Each well (except for unstained controls) received 5 μL phycoerythrin-conjugated anti-CD33. After wells were incubated on ice for 45 minutes in the dark, cells were washed twice with FACS buffer, resuspended in 200 μL FACS buffer, and analyzed on a Guava EasyCyte™ (EMD Millipore, Billerica Mass.) flow cytometer.

The numbers of CD33 positive monocytes were recorded, and cytotoxicity determined by calculating the number of monocytes as a % of untreated (PBMCs only) at each antibody concentration.

Results

Figure 10:
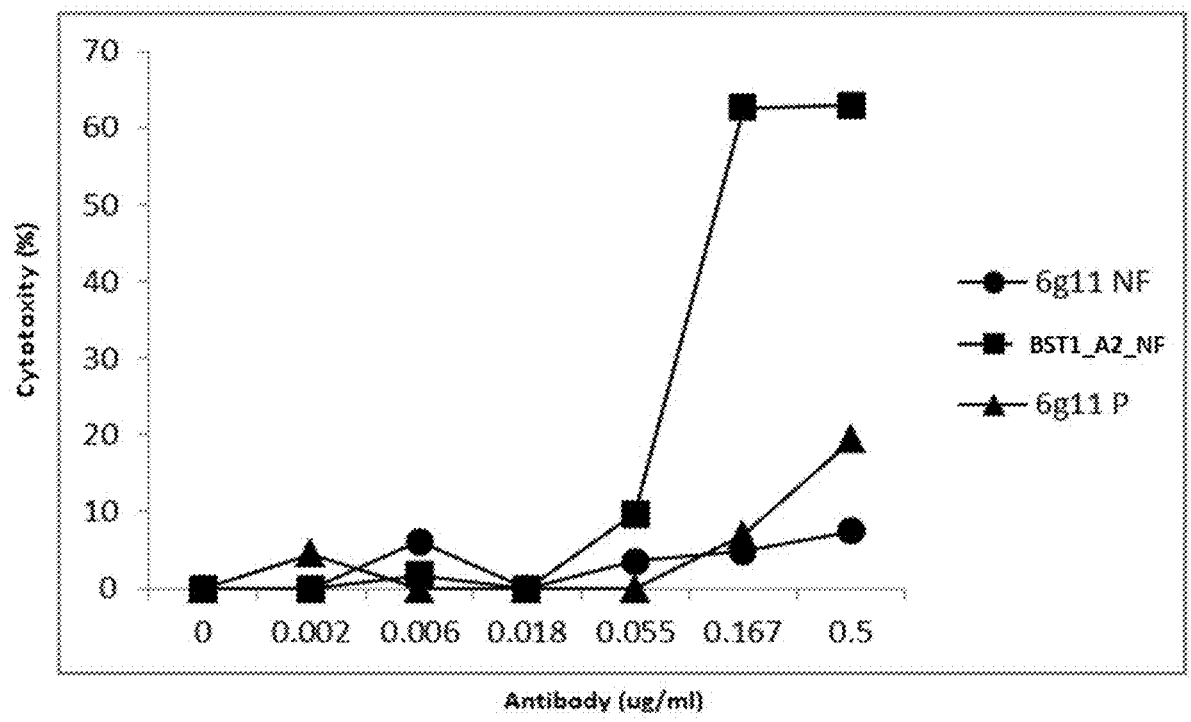
FIG. 10 depicts BST1_A2_NF eliciting an antibody dependent cellular cytotoxicity (ADCC) response against monocytes cells in the presence of effector cells.

FIG. 10 displays the combined % cytotoxicity of three replicates at each antibody concentration for each of 5 different healthy donors tested. The results show BST1_A2_NF promotes homogenous ADCC against monocytes in a dose-dependent manner. Non-targeting antibody, 6g11NF (non-fucosylated antibody) or its parent, 6g11P, had no effect on CD33-positive monocyte numbers. This shows BST1_A2_NF has the ability to promote target cell killing by effector cells in a dose dependent manner.

Example 12: BST1_A2_NF Binds BST1 Cynomolgus Monkey Antigen-Transfected 293FS

HEK293FS cells transfected with cynomolgus monkey CD157/BST1 protein (ADQ89190.1) were washed twice with PBS and re-suspended in FACS buffer (PBS+2% fetal bovine serum [FBS]). Cells were stained with either 0.25 µg/mL BST1_A2_NF antibody or 0.25 µg/mL human IgG isotype control antibody, followed by anti-human phycoerythrin secondary antibodies (Southern Biotech, Birmingham Ala.). Samples were analyzed on a Guava Easycyte (Millipore) and the mean fluoresence intensity (MFI) recorded.

Figure 11A:
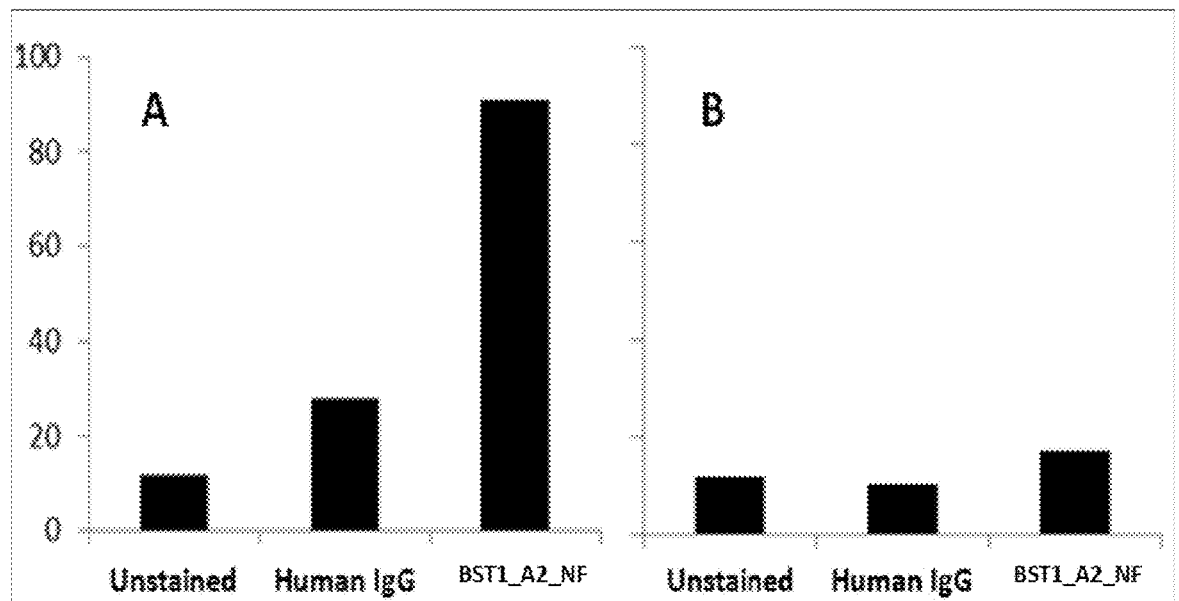
FIG. 11A depicts results of flow cytometric anaysis of BST1_A2_NF on BST1 cynomolgus monkey antigen-transfected HEK 293FS cells.

FIG. 11a shows BST1_A2_NF binds BST1 cynomolgus monkey antigen-transfected 293FS cells while untransfected 293FS cells (lipid only) are not recognized by BST1_A2_NF.

Figure 11B:
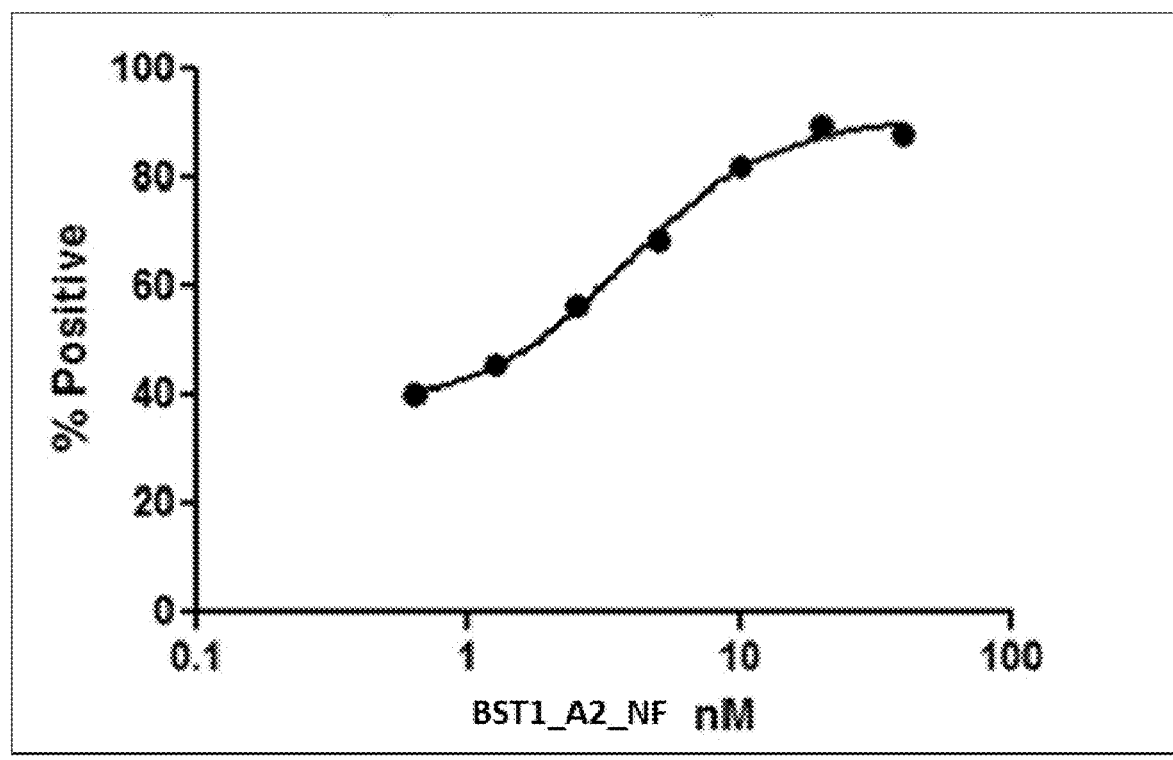
FIG. 11B depicts results of flow cytometric anaysis of various concentrations of BST1_A2_NF on BST1 cynomolgus monkey antigen-transfected HEK 293FS cells.

The experiment was repeated with various concentrations of BST1_A2_NF followed by staining with anti-human phycoerythrin secondary antibody. The percentage of PE positive cells were plotted against antibody concentration. The titration curve depicted in FIG. 11b shows BST1_A2_NF binding to BST1 cynomolgus monkey antigen-transfected HEK 293FS cells. The $EC_{50}$ was determined to be 5 nM. The results show BST1_A2_NF antibody cross-reacts with cynomolgus monkey antigen on transfected (overexpressing) cells.

Example 13: BST1_A2_NF Binds BST1 Antigen Endogenously Expressed on Cynomolgus Monocytes Guava 1× Lysing Solution (Millipore: 4700-0081) was added to blood obtained from naïve cynomolgus monkeys in a ratio of 38 mL lysing solution to 1 mL blood, mixed gently, and allowed to stand for 15 minutes at room temperature. Cells remaining after RBC lysis were washed twice in PBS, re-suspended in 10 mL FACS buffer (PBS plus 2% FBS), and placed in wells (100 µL/well) for staining. Human AB serum was added to each well to block Fc receptor binding Alexa Fluor® 488 CD11b antibody (cynomolgus cross-reactive clone, ICRF44, Becton Dickinson catalog number 561687) was added to wells to stain monocytes and granulocytes. BST1_A2_NF conjugated to-PE was added to stain BST1-positive cells. Reactions were incubated on ice for 45 minutes, washed twice, and re-suspended in FACS buffer. Samples were analyzed on a Guava Easycyte (Millipore).

The results demonstrates co-staining of CD11b and BST1_A2_NF in cynomolgus whole blood after RBC lysis, indicating that anti-human BST1_A2_NF recognizes the BST1 antigen endogenously expressed on cynomolgus monocytes.

Example 14: An Exploratory Intravenous Infusion Toxicity Study of BST1_A2_NF in Cynomolgus Monkeys with a 21-Day Recovery Period Eight female monkeys were assigned to the study with 2 monkeys/group. Either Phosphate Buffered Saline (PBS) or BST1_A2_NF was administered by a 15-minute intravenous infusion on Days 1 (see Table 14.1) and 59 (see Table 14.2) at a dose volume of 2.10 mL/kg.

Parameters evaluated included cageside and detailed observations, body weights and body weight changes, food consumption, clinical pathology (clinical chemistry, hematology, coagulation and urinalysis), gross pathology, selected microscopic pathology, toxicokinetics and functional analysis (depletion of monocytes/granulocytes and receptor occupancy) by fluorescence-activated cell sorting (FACS) assay.

Blood samples for clinical chemistry, hematology and urine analyses were collected from all study animals during acclimation, prior to each dose (Days 1 and 58), 24, 48, 72 and 96 hours, 7 days, 10 days and 14 days post each dose; at 22 days post the first dose and then weekly thereafter until the second dose. Blood samples for coagulation evaluation were collected from all study animals during acclimation, prior to each dose (Days 1 and 58), and prior to necropsy (Day 80). Blood samples for toxicokinetic evaluations were collected from all study animals prior to each dose (Days 1 and 59), 24, 48, 72 and 96 hours, 7 days, 10 days and 14 days post each dose; at 22 days post the first dose and then weekly thereafter until the second dose. Blood samples for FACS assay were collected from all study animals prior to each dose (Days 1 and 58), 1, 3, 7, 11 and 14 days post each dose; at 22 days post the first dose and then weekly thereafter until the second dose; prior to necropsy (Day 80).

All study animals were euthanized and necropsied following the final blood collection on Day 80.

Toxicokinetics

Plasma samples were received on dry ice and stored at −80° C. until analyzed. The ELISA assays were performed to assess antigen specific human IgG. Standard curves were generated using aliquots of the original test article. Antigen specific human IgG was determined as follows: ELISA (Nunc catalog number 44-2404-21) plates were coated overnight at 4° C. with 1 µg/ml soluble BST1 Antigen-CFLIS in PBS (provided by Alere). Plates were washed and blocked with Superblock. After washing again, standard curves and appropriately diluted samples were plated in PBS containing 2% FBS. After incubating for 1 hour at room temperature, the plates were washed. The detection antibody was anti-human kappa peroxidase conjugated goat polyclonal antibody (Millipore catalog number A9502P, lot number NG1909833) at 1 in 5000 dilution in PBS plus 2% FBS. After washing, plates were developed with 1-Step Ultra TMB-ELISA substrate (Thermo Scientific catalog number 34028) and the reactions were stopped with dilute sulfuric acid (98 g/L Ricca Chemical Company catalog number 8140-16). The plates were read at 450 nm. The lowest detectable level of human antigen specific IgG in the assay is 1.4 ng/ml. The highest concentration of serum from the vehicle treated animals provided an ELISA reading similar to the blank control wells. The lowest concentration of human antigen specific IgG detected in the serum samples was about 340 ng/ml. The highest concentration of serum analyzed was a 1 to 100 dilution of sample in ELISA assay buffer (or 1% final concentration of cynomolgus monkey serum).

Results

Two doses of BST1_A2_NF at 0.5, 5, and 20 mg/kg/dose (8 weeks apart) via 15-minute intravenous infusion in female cynomolgus monkeys were well tolerated. There was no mortality or moribundity during the course of the study. There were no BST1_A2_NF-related changes on clinical observations, body weights, food consumption, clinical chemistry, coagulation, urinalysis, organ weights, bone marrow smear, macroscopic or microscopic evaluations.

Figure 12A:
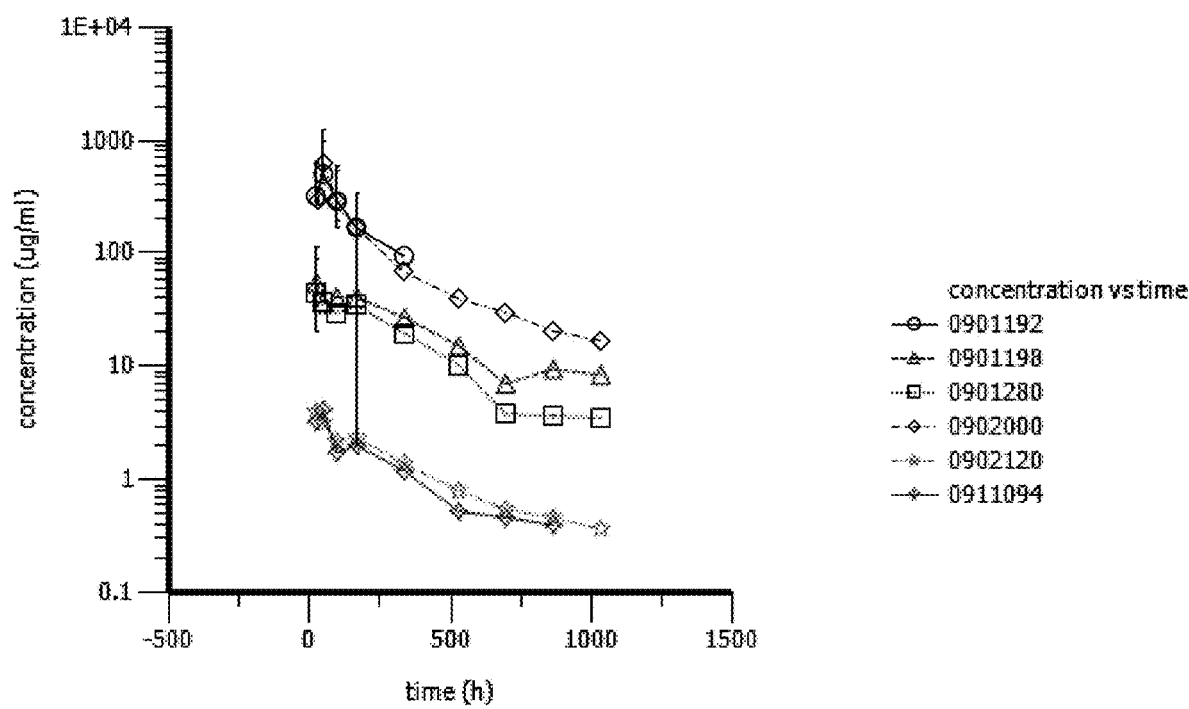
FIG. 12A depicts the TK profile of BST1_A2_NF after IV infusion for the first dosing in an exploratory toxicity study in cynomolgus monkeys
Figure 12B:
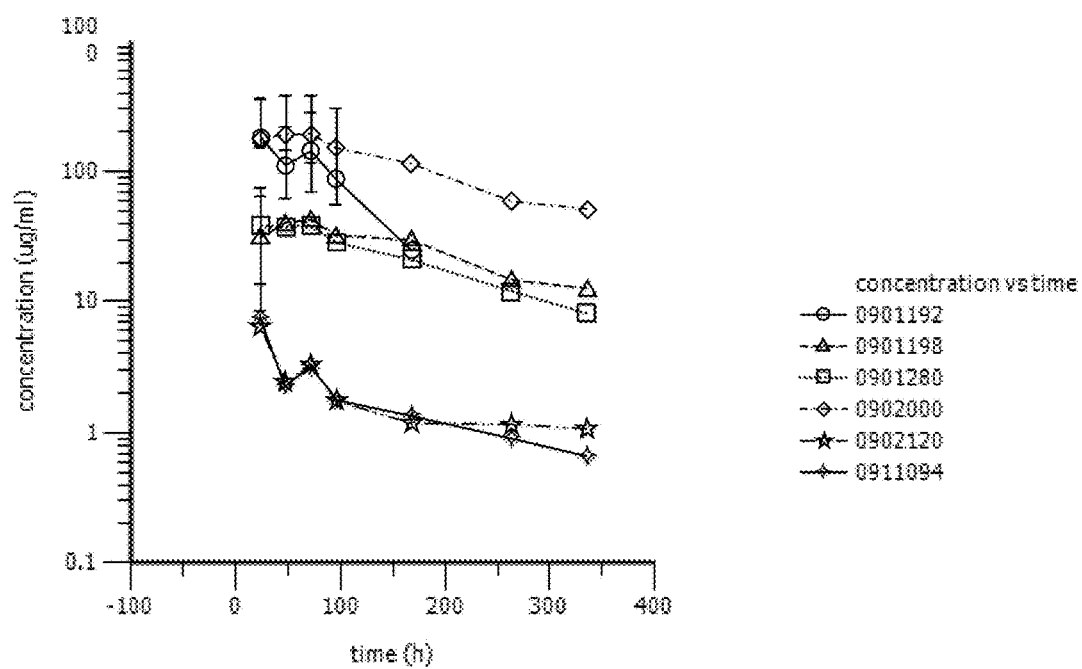
FIG. 12B depicts the TK profile of BST1_A2_NF after IV infusion for the second dosing in an exploratory toxicity study in cynomolgus monkeys

The TK samples taken following the first dose of BST1_A2_NF yielded a range between 0.37 µg/ml to 624 µg/ml of antigen specific human IgG. The concentrations for the 20 mg/kg group ranged from a low of undetectable for monkey 0901192 starting on Day 22 to a high of 624 µg/ml for monkey 0902000 on Day 2. The 5 mg/kg group ranged between a high of 55 µg/ml on Day 1 to a low of 3.57 µg/ml on Day 43. The 0.5 mg/kg group ranged from a high of 4 µg/ml on Days 1 and 2 to a low of 0 to 0.37 µg/ml on Day 43 (see FIG. 12a). Following the second dose, the antigen specific human IgG levels ranged from a low of undetectable 11 days post dose for monkey 0901192, to a high of 190.59 µg/ml on the second day after dosing for monkey 0902000 in the 20 mg/kg group. For the 5 mg/kg group antigen specific IgG levels ranged from a high of 42.60 µg/ml on Day 3, to a low of 8.03 µg/ml on Day 14 (last day tested) after the second dose. The 0.5 mg/kg group had antigen specific IgG levels ranging from 7.28 µg/ml on Day 1 to 0.65 µg/ml on Day 14 after the second dose (see FIG. 12b).

SEQUENCE SUMMARY

| SEQ ID No | Description | Sequence |
|---|---|---|
| 1 | aa VH_A1 | MKQSTIALALLPLLFTPVAKAQVKLQQSGAELVRPGSSV KISCKASGYAFSNSWINWVKQRPGQGLEWIGQIYPGDY DTNYNGKFKGKATLTADYSSSTAYMQLNSLTSEDSAVY FCARGGSIYYGNLGFFDVWGAGTTVTVSSAKTTPPSVYP LAPGSAAQTNSMVTLGCLVKGYFPEPVTVTWNSGSLSS GVHTFPAVLQSDLYTLSSSVTVPSSTWPSETVTCNVAHP ASSTKVDKKIVPRDCHHHHHH |
| 2 | aa VH_A2 | MKQSTIALALLPLLFTPVAKAQAYLQQSGPELVKAGASV KMSCKASGYSFIEYTINWVKQSHGKSLEWIGNIDPYYGT TYYNQMFTGKATLTVDQSSNTAYMQLKSLTSEDSAVYF CARGSAWFPYWGQGTLVTVSAAKTTPPSVYPLAPGSAA QTNSMVTLGCLVKGYFPEPVTVTWNSGSLSSGVHTFPA VLQSDLYTLSSSVTVPSSTWPSETVTCNVAHPASSTKVD KKIVPRDCHHHHHH |
| 3 | aa VK_A1 | MKYLLPTAAAGLLLLAAQPAMAEMVLTQSPAIMSTSLG ERVTMTCTASSRVSSSYLHWYQQKPGSSPKLWIYSTSNL ASGVPARFSGSGSGTSYSLTISSMEAEDAATYYCHQYHR SPYTFGGGTKLEIKRADAAPTVSIFPPSSEQLTSGGASVV CFLNNFYPKDINVKWKIDGSERQNGVLNSWTDQDSKDS TYSMSSTLTLTKDEYERHNSYTCEATHKTSTSPIVKSFNR NES |
| 4 | aa VK_A2 | MKYLLPTAAAGLLLLAAQPAMADIVMSQSPAIMSASPG EKVTMTCSASSSVTYMYWYQQKPGSSPRLLIYDTSNLAS GVPVRFSGSGSGTSYSLTISRMEAEDTATYYCQQWSNYP LTFGAGTKLELKRADAAPTVSIFPPSSEQLTSGGASVVCF LNNFYPKDINVKWKIDGSERQNGVLNSWTDQDSKDSTY SMSSTLTLTKDEYERHNSYTCEATHKTSTSPIVKSFNRNE S |
| 5 | nt VH_A1 | acgctttgtacatggagaaaataaagtgaaacaaagcactattgcactggcactcttaccg ctcttatttacccctgtggcaaaagcccaggtgaagcttcagcagtccgggctgagctg gtgaggcctgggtcctcagtgaagatttcctgcaaggcttctggctacgcattcagtaactc ctggataaactgggtgaagcagaggcctggacagggtcttgaggattggacagattta tcctggagattatgatactaactacaatggaaaattcaagggtaaagccacactgactgca gactactcctccagcacagcctacatgcagctcaacagctaacatctgaggactctgcg gtctatttctgtgcaaggggggatcgatctactatggtaacctcgggttcttcgatgtctgg ggcgcagggaccacggtcaccgtctcctcagccaaaacgacacccccatctgtctatcc actggcccctggatctgctgcccaaactaactccatggtgaccctgggatgcctggtcaa gggctatttccctgagccagtgacagtgacctggaactctggatccctgtccagcggtgtg cacaccttcccagctgtcctgcagtctgacctctacactctgagcagctcagtgactgtccc ctccagcacctggcccagcgagaccgtcacctgcaacgttgcccaccggccagcagc accaaggtggacaagaaaattgtgcccagggattgtcatcatcaccatcaccatcactaat tgacagcttatcatcgatangct |
| 6 | nt VH_A2 | aaaaccctggcgttacccacgctttgtacatggagaaaataaagtgaaacaaagcactatt gcactggcactcttaccgctcttatttacccctgtggcaaaagcccaggcttatctacagca gtctggacctgagctggtgaaggctggcgcttcagtgaagatgtcctgcaaggcttctggt tactcattcattgagtacaccataaactgggtgaaacagagccatgaaagagccttgagt ggattggaaatattgatccttattatggaaccacttattacaatcagatgttcacgggcaagg ccacattgactgtagaccaatcttccaacactgcctacatgcagctcaagagcctgacatct gaggactctgcagtctatttctgtgcaagaggctccgcctggtttccttactggggccagg ggactctagtcactgtctctgcagccaaaacgacacccccatctgtctatccactggcccct ggatctgctgcccaaactaactccatggtgaccctgggatgcctggtcaagggctatttcc ctgagccagtgacagtgacctggaactctggatccctgtccagcggtgtgcacaccttcc |

SEQUENCE SUMMARY

| SEQ ID No | Description | Sequence |
|---|---|---|
| | | cagctgtcctgcagtctgacctctacactctgagcagctcagtgactgtcccctccagcac ctggcccagcgagaccgtcacctgcaacgttgcccaccggccagcagcaccaaggtg gacaagaaaattgtgcccagggattgtcatcatcaccatcaccatcactaattgacagctta tcatcgat |
| 7 | nt VK_A1 | gttttttggatggagtgaaacgatgaaatacctattgcctacggcagccgctggattgttatt actcgctgcccaaccagccatggccgaaatggttctcacccagtctccagcaatcatgtct acatctctagggaacgggtcaccatgacctgcagtgccagctcacgtgtaagttccagtt acttgcactggtaccagcagaagccaggatcctcccccaaactctggatttatagtacatc caacctggcttctggagtcccagctcgcttcagtggcagtgggtctgggacctcttactctc tcacaatcagcagcatggaggctgaagatgctgccacttattactgccaccagtatcatcgt tcccccgtacacgttcggaggggggaccaagctggaaataaaacgggctgatgctgcac caactgtatccatcttccaccatccagtgagcagttaacatctggaggtgcctcagtcgtg tgcttcttgaacaacttctaccccaaagacatcaatgtcaagtggaagattgatggcagtga acgacaaaatggcgtcctgaacagttggactgatcaggacagcaaagacagcacctaca gcatgagcagcaccctcacgttgaccaaggacgagtatgaacgacataacagctatacct gtgaggccactcacaagacatcaacttcacccattgtcaagagcttcaacaggaatgagtc ttaagtgattagctaattctagaacg |
| 8 | nt VK_A2 | actctctactgtttctccataccgtttttttggatggagtgaaacgatgaaatacctattgcct acggcagccgctggattgttattactcgctgcccaaccagccatggccgacatcgttatgt ctcagtctccagcaatcatgtctgcatctccaggggagaaggtcaccatgacctgcagtg ccagctcaagtgtaacttacatgtactggtaccagcagaagccaggatcctcccccagact cctgatttatgacacatccaacctggcttctggagtcccagctcgcttcagtggcagtgggtc tgggacctcttactctctcacaatcagccgaatggaggctgaagatactgccacttattact gccagcagtggagtaattacccactcacgttcggtgctgggaccaagctggagctgaaa cgggctgatgctgcaccaactgtatccatcttccaccatccagtgagcagttaacatctgg aggtgcctcagtcgtgtgcttcttgaacaacttctaccccaaagacatcaatgtcaagtgga agattgatggcagtgaacgacaaaatggcgtcctgaacagttggactgatcaggacagc aaagacagcacctacagcatgagcagcaccctcacgttgaccaaggacgagtatgaac gacataacagctatacctgtgaggccactcacaagacatcaacttcacccattgtcaagag cttcaacaggaatgagtcttaagtgattagctaattctagaacgcgtcacttggcactggcc gtcgtttta |
| 9 | aa VH_CDR1_A1 | GYAFSNSWINW |
| 10 | aa VH_CDR1_A2 | GYSFIEYTINW |
| 11 | aa VH_CDR2_A1 | GQIYPGDYDTNYNGKFK |
| 12 | aa VH_CDR2_A2 | GNIDPYYGTTYYNQMFT |
| 13 | aa VH_CDR3_A1 | ARGGSIYYGNLGFFDV |
| 14 | aa VH_CDR3_A2 | ARGSAWFPY |
| 15 | aa VK_CDR1_A1 | TASSRVSSSYLH |
| 16 | aa VK_CDR1_A2 | SASSSVTYMY |
| 17 | aa VK_CDR2_A1 | STSNLAS |
| 18 | aa VK_CDR2_A2 | DTSNLAS |
| 19 | aa VK_CDR3_A1 | HQYHRSPYT |
| 20 | aa VK_CDR3_A2 | QQWSNYPLT |
| 21 | nt VH_CDR1_A1 | ggctacgcattcagtaactcctggataaactgg |
| 22 | nt VH_CDR1_A2 | ggttactcattcattgagtacaccataaactgg |
| 23 | nt VH_CDR2_A1 | ggacagatttatcctggagattatgatactaactacaatggaaaattcaag |
| 24 | nt VH_CDR2_A2 | ggaaatattgatccttattatggaaccacttattacaatcagatgttcacg |
| 25 | nt VH_CDR3_A1 | gcaagggggggatcgatctactatggtaacctcgggttcttcgatgtc |
| 26 | nt VH_CDR3_A2 | gcaagaggctccgcctggtttccttac |
| 27 | nt VK_CDR1_A1 | actgccagctcacgtgtaagttccagttacttgcac |
| 28 | nt VK_CDR1_A2 | agtgccagctcaagtgtaacttacatgtac |

-continued

SEQUENCE SUMMARY

| SEQ ID No | Description | Sequence |
|---|---|---|
| 29 | nt VK_CDR2_A1 | agtacatccaacctggcttct |
| 30 | nt VK_CDR2_A2 | gacacatccaacctggcttct |
| 31 | nt VK_CDR3_A1 | caccagtatcatcgttccccgtacacg |
| 32 | nt VK_CDR3_A2 | cagcagtggagtaattacccactcacg |
| 33 | IGHV1-80*01 (Genebank: AC160990 Musmus) nt 138392-138424 | ggctacgcattcagtagctactggatgaactgg |
| 34 | IGHV1-80*01 (Genebank: AC160990 Musmus) nt 138461-138511 | ggacagatttatcctggagatggtgatactaactacaacggaaagttcaag |
| 35 | IGHV1-39*01 (Genebank: AC079181 Musmus) nt 153362-153394 | ggttactcattcactgactacaacatgaactgg |
| 36 | IGHV1-39*01 (Genebank: AC079181 Musmus) nt 153431-153481 | ggagtaattaatcctaactatggtactactagctacaatcagaagttcaag |
| 37 | IGKV4-74*01 (Genebank: AJ231217 Musmus) nt 496-531 | actgccagctcaagtgtaagttccagttacttgcac |
| 38 | IGKV4-74*01 (Genebank: AJ231217 Musmus) nt 577-597 | agcacatccaacctggcttct |
| 39 | IGKV4-74*01 (Genebank: AJ231217 Musmus) nt 691-718 | caccagtatcatcgttccccaccca |
| 40 | IGKV4-55*01 (Genebank: AJ231225 Musmus) nt 523-552 | agtgccagctcaagtgtaagttacatgtac |
| 41 | IGKV4-55*01 (Genebank: AJ231225 Musmus) nt 598-618 | gacacatccaacctggcttct |
| 42 | IGKV4-55*01 (Genebank: AJ231225 Musmus) nt 715-739 | cagcagtggagtagttacccaccca |
| 43 | ADP-ribosyl cyclase 2(CD157; BST1) | MAAQGCAASRLLQLLLQLLLLLLLLAAGGARARWRGE GTSAHLRDIFLGRCAEYRALLSPEQRNKNCTAIWEAFKV ALDKDPCSVLPSDYDLFINLSRHSIPRDKSLFWENSHLLV NSFADNTRRFMPLSDVLYGRVADFLSWCRQKNDSGLDY QSCPTSEDCENNPVDSFWKRASIQYSKDSSGVIHVMLNG SEPTGAYPIKGFFADYEIPNLQKEKITRIEIWVMHEIGGPN VESCGEGSMKVLEKRLKDMGFQYSCINDYRPVKLLQCV DHSTHPDCALKSAAAATQRKAPSLYTEQRAGLIIPLFLVL ASRTQL |
| 44 | aa 29 - 292 of ADP-ribosyl cyclase 2 (CD157; BST1) | GARARWRGEGTSAHLRDIFLGRCAEYRALLSPEQRNKN CTAIWEAFKVALDKDPCSVLPSDYDLFINLSRHSIPRDKS LFWENSHLLVNSFADNTRRFMPLSDVLYGRVADFLSWC RQKNDSGLDYQSCPTSEDCENNPVDSFWKRASIQYSKDS |

SEQUENCE SUMMARY

| SEQ ID No | Description | Sequence |
|---|---|---|
| | | SGVIHVMLNGSEPTGAYPIKGFFADYEIPNLQKEKITRIEI WVMHEIGGPNVESCGEGSMKVLEKRLKDMGFQYSCIND YRPVKLLQCVDHSTHPDCALKSAAAATQRK |
| 45 | A2 VH (amino acids 21-137 SEQ ID No: 2) | QAYLQQSGPELVKAGASVKMSCKASGYSFIEYTINWVK QSHGKSLEWIGNIDPYYGTTYYNQMFTGKATLTVDQSS NTAYMQLKSLTSEDSAVYFCARGSAWFPYWGQGTLVT VSA |
| 46 | VH1 - Humanised VHA2 | QVQLVQSGA EVKKPGASVK VSCKASGYSF IEYTINWVRQ APGQGLEWIGNIDPYYGTTYY NQMFTGRATL TVDTSISTAY |
| 47 | BF238102 VH | MELSRLRSDDTAVYYCARGSAWF PYWGQGTLV TVSS QVQLVQSGA EVKKPGASVK VSCKASGYSF TXXXXXWVRQ APGQGLEWMG XXXXXXXXXX XXXXXXRVTL TRDTSISTAY MELSRLRSDDTAVYYCARXXXXX XXXWGQGTLV PVSS |
| 48 | A2 VL (amino acids 22-128 SEQ ID No: 4) | DIVMSQSPA IMSASPGEKV TMTCSAS-SS VTYMYWYQQKPGSSPRLLIY DTSNLASGVP VRFSGSGSGT SYSLTISRMEAEDTATYYCQ QWSNYPLTFG AGTKLELK |
| 49 | VL1 - Humanised VK_A2 | DIQMTQSPS SLSASVGDRV TITCSAS-SS VTYMYWYQQKPGKAPKLLIY DTSNLASGVP SRFSGSGSGT DYTLTISSLQPEDFATYYCQ QWSNYPLTFG QGTKVEIK |
| 50 | X72441 VL | DIQMTQSPS SLSASVGDRV TITCXXXXXX XXXXXWYQQKPGKAPKLLIY XXXXXXXGVP SRFSGSGSGT DFTLTISSLQPEDFATYYCX XXXXXXXXFG QGTKVEIK |
| 51 | VH1_CDR2 | NIDPYYGTTYYNQMFQ MKQSTIALALLPLLFTPVAKAQVQLQQSRAELVMPGAS VKMSCKTSGYTFSDYWVHWVRQRPGQGLEWIGAIDGS DTFNDYSQKFKGRATLTVDESSSTVYMQLSSLTSEDSAV |
| 52 | aa VH_A3 | YYCARGGLLQYWGQGTTLTVSSAKTTPPSVYPLAPGSA AQTNSMVTLGCLVKGYFPEPVTVTWNSGSLSSGVHTFP AVLQSDLYTLSSSVTVPSSTWPSETVTCNVAHPASSTKV DKKIVPRDCHHHHHH |
| 53 | aa VK_A3 | MKYLLPTAAAGLLLLAAQPAMADIQLTQSPASLSASVGE TVTITCRASENIYSYLAWYQQKQGKSPQLLVYNTKTLGE GVPSRFSGSGSGTQFSLKINSLQPEDFGSYYCQHHYGTPF TFGSGTKLEIKRADAAPTVSIFPPSSEQLTSGGASVVCFLN NFYPKDINVKWKIDGSERQNGVLNSWTDQDSKDSTYSM SSTLTLTKDEYERHNSYTCEATHKTSTSPIVKSFNRNES |
| 54 | nt VH_A3 | gtgaaacaaagcactattgcactggcactcttaccgctcttatttaccctgtggcaaaagc ccaggtccagctgcagcagtctagggctgaacttgtgatgcctggggcttcagtgaagat gtcctgcaagacttctggctacacattctctgactactgggtacactgggtgaggcagagg cctggacaaggccttgagtggatcggagcgattgatggttctgatacttttaatgactacag tcagaagtttaagggcagggccacattgactgtagacgaatcctccagcacagtctacat gcaactcagcagcctgactgcatctgaggactctgcggtctattactgtgcaagggggcct tcttcagtactggggccaaggcaccactctcacagtctcctcagccaaaacgacacccc atctgtctatccactggccctggatctgctgcccaaactaactccatggtgaccctgggat gcctggtcaagggctatttccctgagccagtgacagtgacctggaactctggatccctgtc cagcggtgtgcacaccttcccagctgtcctgcagtctgacctctacactctgagcagctca gtgactgtcccctccagcacctggcccagcgagaccgtcacctgcaacgttgcccaccc ggccagcagcaccaaggtggacaagaaaattgtgcccagggattgtcatcatcaccatc accatcactaa |
| 55 | nt VK_A3 | atgaaatacctattgcctacggcagccgctggattgttattactgctgcccaaccagccat ggccgacattcagctgacccagtctccagcctccctatctgcatctgtgggagaaactgtc accatcacatgtcgagcaagtgaaaacatttacagttatttagcatggtatcagcagaaaca gggaaaatctcctcagctcctggtctataatacaaaaaccttaggagaaggtgtgccatca aggttcagtggcagtggatcgggcacacaattttctctgaagatcaacagcctgcagcctg aagattttggagttattactgtcaacatcattatggtactccattcacgttcggctcgggga caaagttggaaataaaacgggctgatgctgcaccaactgtatccatcttcccaccatccag |

SEQUENCE SUMMARY

| SEQ ID No | Description | Sequence |
|---|---|---|
| | | tgagcagttaacatctggaggtgcctcagtcgtgtgcttcttgaacaacttctaccccaaag acatcaatgtcaagtggaagattgatggcagtgaacgacaaaatggcgtcctgaacagtt ggactgatcaggacagcaaagacagcacctacagcatgagcagcaccctcacgttgac caaggacgagtatgaacgacataacagctatacctgtgaggccactcacaagacatcaa cttcacccattgtcaagagcttcaacaggaatgagtcttaa |
| 56 aa | VH_CDR1_A3 | GYTFSDYWVHW |
| 57 aa | VH_CDR2_A3 | GAIDGSDTFNDYSQKFK |
| 58 aa | VH_CDR3_A3 | ARGGLLQY |
| 59 aa | VK_CDR1_A3 | RASENIYSYLA |
| 60 aa | VK_CDR2_A3 | NTKTLGE |
| 61 aa | VK_CDR3_A3 | QHHYGTPFT |
| 62 nt | VH_CDR1_A3 | ggctacacattctctgactactgggtacactgg |
| 63 nt | VH_CDR2_A3 | ggagcgattgatggttctgatacttttaatgactacagtcagaagtttaag |
| 64 nt | VH_CDR3_A3 | gcaaggggggccttcttcagtac |
| 65 nt | VK_CDR1_A3 | cgagcaagtgaaaacatttacagttatttagca |
| 66 nt | VK_CDR2_A3 | aatacaaaaaccttaggagaa |
| 67 nt | VK_CDR3_A3 | caacatcattatggtactccattcacg |
| 68 | IGHV1-69*01 (AC073939) | ggctacaccttcaccagctactggatgcactgg |
| 69 | IGHV1-69*01 (AC073939) | ggagagattgatccttctgatagttatactaactacaatcaaaagttcaag |
| 70 | IGKV12-44*01 (AJ235955) | cgagcaagtgagaatatttacagttatttagca |
| 71 | IGKV12-44*01 (AJ235955) | aatgcaaaaaccttagcagaa |
| 72 | IGKV12-44*01 (AJ235955) | caacatcattatggtactcctcc |

The invention claimed is:

1. A method of treating ovarian cancer in a patient comprising administering to the patient an effective amount of an antibody, or antigen binding portion thereof, wherein the antibody, or antigen binding portion thereof, comprises a heavy chain variable region CDR1 comprising SEQ ID NO:10, a heavy chain variable region CDR2 comprising SEQ ID NO: 12 or SEQ ID NO: 51, a heavy chain variable region CDR3 comprising SEQ ID NO:14, a light chain variable region CDR1 comprising SEQ ID NO:16, a light chain variable region CDR2 comprising SEQ ID NO: 18, and a light chain variable region CDR3 comprising SEQ ID NO:20.

2. The method of claim 1, wherein the antibody, or antigen binding portion thereof:
   (a) is internalized by a cell expressing bone marrow stromal antigen 1 (BST1);
   (b) induces antibody dependent cell-mediated cytotoxicity (ADCC);
   (c) induces complement dependent cytotoxicity (CDC); and/or
   (d) induces T-cell cytotoxicity.

3. The method of claim 1, wherein the antibody is of an IgG1 isotype.

4. A method of treating ovarian cancer in a patient comprising administering to the patient an effective amount of an antibody, or antigen binding portion thereof, wherein the antibody, or antigen binding portion thereof, comprises a heavy chain variable region comprising SEQ ID NO: 2 and a light chain variable region comprising SEQ ID NO: 4.

5. The method of claim 4, wherein the antibody, or antigen binding portion thereof:
   (a) is internalized by a cell expressing BST1;
   (b) induces antibody dependent cell-mediated cytotoxicity (ADCC);
   (c) induces complement dependent cytotoxicity (CDC); and/or
   (d) induces T-cell cytotoxicity.

6. The method of claim 4, wherein the antibody is of an IgG1 isotype.

7. A method of treating ovarian cancer in a patient comprising administering to the patient an effective amount of an antibody, or antigen binding portion thereof, wherein the antibody, or antigen binding portion thereof, comprises a heavy chain variable region comprising SEQ ID NO: 46 and a light chain variable region comprising SEQ ID NO: 49.

8. The method of claim 7, wherein the antibody, or antigen binding portion thereof:
   (a) is internalized by a cell expressing BST1;
   (b) induces antibody dependent cell-mediated cytotoxicity (ADCC);
   (c) induces complement dependent cytotoxicity (CDC); and/or
   (d) induces T-cell cytotoxicity.

9. The method of claim 7, wherein the antibody is of an IgG1 isotype.

10. The method of any one of claims 1-7, wherein the antibody, or antigen binding portion thereof, further comprises a covalently attached moiety.

11. The method of claim 10, wherein the moiety is a drug selected from the group consisting of a maytansinoid, a dolastatin, an auristatin, a trichothecene, a calicheamicin, CC1065 and derivatives thereof.

* * * * *

SEQUENCE LISTING

<160> NUMBER OF SEQ ID NOS: 72

<210> SEQ ID NO 1
<211> LENGTH: 253
<212> TYPE: PRT
<213> ORGANISM: Mus musculus

<400> SEQUENCE: 1

```
Met Lys Gln Ser Thr Ile Ala Leu Ala Leu Leu Pro Leu Leu Phe Thr
1               5                   10                  15

Pro Val Ala Lys Ala Gln Val Lys Leu Gln Gln Ser Gly Ala Glu Leu
            20                  25                  30

Val Arg Pro Gly Ser Ser Val Lys Ile Ser Cys Lys Ala Ser Gly Tyr
        35                  40                  45

Ala Phe Ser Asn Ser Trp Ile Asn Trp Val Lys Gln Arg Pro Gly Gln
    50                  55                  60

Gly Leu Glu Trp Ile Gly Gln Ile Tyr Pro Gly Asp Tyr Asp Thr Asn
```

-continued

```
                65                  70                  75                  80
        Tyr Asn Gly Lys Phe Lys Gly Lys Ala Thr Leu Thr Ala Asp Tyr Ser
                        85                  90                  95
        Ser Ser Thr Ala Tyr Met Gln Leu Asn Ser Leu Thr Ser Glu Asp Ser
                    100                 105                 110
        Ala Val Tyr Phe Cys Ala Arg Gly Gly Ser Ile Tyr Tyr Gly Asn Leu
                    115                 120                 125
        Gly Phe Phe Asp Val Trp Gly Ala Gly Thr Thr Val Thr Val Ser Ser
        130                 135                 140
        Ala Lys Thr Thr Pro Pro Ser Val Tyr Pro Leu Ala Pro Gly Ser Ala
        145                 150                 155                 160
        Ala Gln Thr Asn Ser Met Val Thr Leu Gly Cys Leu Val Lys Gly Tyr
                        165                 170                 175
        Phe Pro Glu Pro Val Thr Val Thr Trp Asn Ser Gly Ser Leu Ser Ser
                    180                 185                 190
        Gly Val His Thr Phe Pro Ala Val Leu Gln Ser Asp Leu Tyr Thr Leu
                    195                 200                 205
        Ser Ser Ser Val Thr Val Pro Ser Ser Thr Trp Pro Ser Glu Thr Val
                210                 215                 220
        Thr Cys Asn Val Ala His Pro Ala Ser Ser Thr Lys Val Asp Lys Lys
        225                 230                 235                 240
        Ile Val Pro Arg Asp Cys His His His His His His
                        245                 250

<210> SEQ ID NO 2
<211> LENGTH: 246
<212> TYPE: PRT
<213> ORGANISM: Mus musculus

<400> SEQUENCE: 2

Met Lys Gln Ser Thr Ile Ala Leu Ala Leu Leu Pro Leu Leu Phe Thr
        1               5                   10                  15
        Pro Val Ala Lys Ala Gln Ala Tyr Leu Gln Gln Ser Gly Pro Glu Leu
                    20                  25                  30
        Val Lys Ala Gly Ala Ser Val Lys Met Ser Cys Lys Ala Ser Gly Tyr
                35                  40                  45
        Ser Phe Ile Glu Tyr Thr Ile Asn Trp Val Lys Gln Ser His Gly Lys
        50                  55                  60
        Ser Leu Glu Trp Ile Gly Asn Ile Asp Pro Tyr Tyr Gly Thr Thr Tyr
        65                  70                  75                  80
        Tyr Asn Gln Met Phe Thr Gly Lys Ala Thr Leu Thr Val Asp Gln Ser
                        85                  90                  95
        Ser Asn Thr Ala Tyr Met Gln Leu Lys Ser Leu Thr Ser Glu Asp Ser
                    100                 105                 110
        Ala Val Tyr Phe Cys Ala Arg Gly Ser Ala Trp Phe Pro Tyr Trp Gly
                    115                 120                 125
        Gln Gly Thr Leu Val Thr Val Ser Ala Ala Lys Thr Thr Pro Pro Ser
        130                 135                 140
        Val Tyr Pro Leu Ala Pro Gly Ser Ala Ala Gln Thr Asn Ser Met Val
        145                 150                 155                 160
        Thr Leu Gly Cys Leu Val Lys Gly Tyr Phe Pro Glu Pro Val Thr Val
                        165                 170                 175
        Thr Trp Asn Ser Gly Ser Leu Ser Ser Gly Val His Thr Phe Pro Ala
                    180                 185                 190
```

Val Leu Gln Ser Asp Leu Tyr Thr Leu Ser Ser Val Thr Val Pro
            195                 200                 205

Ser Ser Thr Trp Pro Ser Glu Thr Val Thr Cys Asn Val Ala His Pro
210                 215                 220

Ala Ser Ser Thr Lys Val Asp Lys Lys Ile Val Pro Arg Asp Cys His
225                 230                 235                 240

His His His His His
                245

<210> SEQ ID NO 3
<211> LENGTH: 237
<212> TYPE: PRT
<213> ORGANISM: Mus musculus

<400> SEQUENCE: 3

Met Lys Tyr Leu Leu Pro Thr Ala Ala Ala Gly Leu Leu Leu Leu Ala
1               5                   10                  15

Ala Gln Pro Ala Met Ala Glu Met Val Leu Thr Gln Ser Pro Ala Ile
                20                  25                  30

Met Ser Thr Ser Leu Gly Glu Arg Val Thr Met Thr Cys Thr Ala Ser
            35                  40                  45

Ser Arg Val Ser Ser Ser Tyr Leu His Trp Tyr Gln Gln Lys Pro Gly
    50                  55                  60

Ser Ser Pro Lys Leu Trp Ile Tyr Ser Thr Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys His
            100                 105                 110

Gln Tyr His Arg Ser Pro Tyr Thr Phe Gly Gly Gly Thr Lys Leu Glu
        115                 120                 125

Ile Lys Arg Ala Asp Ala Ala Pro Thr Val Ser Ile Phe Pro Pro Ser
    130                 135                 140

Ser Glu Gln Leu Thr Ser Gly Gly Ala Ser Val Val Cys Phe Leu Asn
145                 150                 155                 160

Asn Phe Tyr Pro Lys Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
        195                 200                 205

Tyr Glu Arg His Asn Ser Tyr Thr Cys Glu Ala Thr His Lys Thr Ser
    210                 215                 220

Thr Ser Pro Ile Val Lys Ser Phe Asn Arg Asn Glu Ser
225                 230                 235

<210> SEQ ID NO 4
<211> LENGTH: 235
<212> TYPE: PRT
<213> ORGANISM: Mus musculus

<400> SEQUENCE: 4

Met Lys Tyr Leu Leu Pro Thr Ala Ala Ala Gly Leu Leu Leu Leu Ala
1               5                   10                  15

Ala Gln Pro Ala Met Ala Asp Ile Val Met Ser Gln Ser Pro Ala Ile
                20                  25                  30

Met Ser Ala Ser Pro Gly Glu Lys Val Thr Met Thr Cys Ser Ala Ser
               35                  40                  45

Ser Ser Val Thr Tyr Met Tyr Trp Tyr Gln Gln Lys Pro Gly Ser Ser
 50                  55                  60

Pro Arg Leu Leu Ile Tyr Asp Thr Ser Asn Leu Ala Ser Gly Val Pro
 65                  70                  75                  80

Val Arg Phe Ser Gly Ser Gly Ser Gly Thr Ser Tyr Ser Leu Thr Ile
                 85                  90                  95

Ser Arg Met Glu Ala Glu Asp Thr Ala Thr Tyr Tyr Cys Gln Gln Trp
            100                 105                 110

Ser Asn Tyr Pro Leu Thr Phe Gly Ala Gly Thr Lys Leu Glu Leu Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
    210                 215                 220

Pro Ile Val Lys Ser Phe Asn Arg Asn Glu Ser
225                 230                 235

<210> SEQ ID NO 5
<211> LENGTH: 811
<212> TYPE: DNA
<213> ORGANISM: Mus musculus
<220> FEATURE:
<221> NAME/KEY: misc_feature
<222> LOCATION: (808)..(808)
<223> OTHER INFORMATION: n is a, c, g, or t

<400> SEQUENCE: 5
acgctttgta catggagaaa ataaagtgaa acaaagcact attgcactgg cactcttacc      60
gctcttattt accccctgtgg caaaagccca ggtgaagctt cagcagtccg gggctgagct    120
ggtgaggcct gggtcctcag tgaagatttc ctgcaaggct tctggctacg cattcagtaa    180
ctcctggata aactgggtga agcagaggcc tggacagggt cttgagtgga ttggacagat    240
ttatcctgga gattatgata ctaactacaa tggaaaattc aagggtaaag ccacactgac    300
tgcagactac tcctccagca cagcctacat gcagctcaac agcctaacat ctgaggactc    360
tgcggtctat ttctgtgcaa ggggggggatc gatctactat ggtaacctcg ggttcttcga    420
tgtctggggc gcagggacca cggtcaccgt ctcctcagcc aaaacgacac ccccatctgt    480
ctatccactg gcccctggat ctgctgccca aactaactcc atggtgaccc tgggatgcct    540
ggtcaagggc tatttccctg agccagtgac agtgacctgg aactctggat ccctgtccag    600
cggtgtgcac accttcccag ctgtcctgca gtctgacctc tacactctga gcagctcagt    660
gactgtcccc tccagcacct ggccagcga ccgtcacc tgcaacgttg cccacccggc      720
cagcagcacc aaggtggaca agaaaattgt gcccagggat tgtcatcatc accatcacca    780
tcactaattg acagcttatc atcgatangc t                                   811

<210> SEQ ID NO 6
<211> LENGTH: 803
<212> TYPE: DNA
<213> ORGANISM: Mus musculus

<400> SEQUENCE: 6

```
aaaaccctgg cgttacccac gctttgtaca tggagaaaat aaagtgaaac aaagcactat      60
tgcactggca ctcttaccgc tcttatttac ccctgtggca aaagcccagg cttatctaca     120
gcagtctgga cctgagctgg tgaaggctgg cgcttcagtg aagatgtcct gcaaggcttc     180
tggttactca ttcattgagt acaccataaa ctgggtgaaa cagagccatg aaagagcct     240
tgagtggatt ggaaatattg atccttatta tggaaccact tattacaatc agatgttcac     300
gggcaaggcc acattgactg tagaccaatc ttccaacact gcctacatgc agctcaagag     360
cctgacatct gaggactctg cagtctattt ctgtgcaaga ggctccgcct ggtttcctta     420
ctggggccag gggactctag tcactgtctc tgcagccaaa acgacacccc catctgtcta     480
tccactggcc cctggatctg ctgcccaaac taactccatg gtgaccctgg gatgcctggt     540
caagggctat ttccctgagc cagtgacagt gacctggaac tctggatccc tgtccagcgg     600
tgtgcacacc ttcccagctg tcctgcagtc tgacctctac actctgagca gctcagtgac     660
tgtcccctcc agcacctggc ccagcgagac cgtcacctgc aacgttgccc acccggccag     720
cagcaccaag gtggacaaga aaattgtgcc cagggattgt catcatcacc atcaccatca     780
ctaattgaca gcttatcatc gat                                              803
```

<210> SEQ ID NO 7
<211> LENGTH: 759
<212> TYPE: DNA
<213> ORGANISM: Mus musculus

<400> SEQUENCE: 7

```
gttttttgg atggagtgaa acgatgaaat acctattgcc tacggcagcc gctggattgt       60
tattactcgc tgcccaacca gccatggccg aaatggttct cacccagtct ccagcaatca     120
tgtctacatc tctagggga cgggtcacca tgacctgcac tgccagctca cgtgtaagtt     180
ccagttactt gcactggtac cagcagaagc caggatcctc ccccaaactc tggatttata     240
gtacatccaa cctggcttct ggagtcccag ctcgcttcag tggcagtggg tctgggacct     300
cttactctct cacaatcagc agcatggagg ctgaagatgc tgccacttat tactgccacc     360
agtatcatcg ttccccgtac acgttcggag ggggaccaa gctggaaata aaacgggctg     420
atgctgcacc aactgtatcc atcttcccac catccagtga gcagttaaca tctggaggtg     480
cctcagtcgt gtgcttcttg aacaacttct accccaaaga catcaatgtc aagtggaaga     540
ttgatggcag tgaacgacaa atggcgtcc tgaacagttg gactgatcag gacagcaaag     600
acagcaccta cagcatgagc agcaccctca cgttgaccaa ggacgagtat gaacgacata     660
acagctatac ctgtgaggcc actcacaaga tcaacttcc acccattgtc aagagcttca     720
acaggaatga gtcttaagtg attagctaat tctagaacg                             759
```

<210> SEQ ID NO 8
<211> LENGTH: 804
<212> TYPE: DNA
<213> ORGANISM: Mus musculus

<400> SEQUENCE: 8

```
actctctact gtttctccat acccgttttt ttggatggag tgaaacgatg aaataccta      60
```

```
tgcctacggc agccgctgga ttgttattac tcgctgccca accagccatg gccgacatcg    120
ttatgtctca gtctccagca atcatgtctg catctccagg ggagaaggtc accatgacct    180
gcagtgccag ctcaagtgta acttacatgt actggtacca gcagaagcca ggatcctccc    240
ccagactcct gatttatgac acatccaacc tggcttctgg agtccctgtt cgcttcagtg    300
gcagtgggtc tgggacctct tactctctca caatcagccg aatggaggct gaagatactg    360
ccacttatta ctgccagcag tggagtaatt acccactcac gttcggtgct gggaccaagc    420
tggagctgaa acgggctgat gctgcaccaa ctgtatccat cttcccacca tccagtgagc    480
agttaacatc tggaggtgcc tcagtcgtgt gcttcttgaa caacttctac cccaaagaca    540
tcaatgtcaa gtggaagatt gatggcagtg aacgacaaaa tggcgtcctg aacagttgga    600
ctgatcagga cagcaaagac agcacctaca gcatgagcag caccctcacg ttgaccaagg    660
acgagtatga acgacataac agctatacct gtgaggccac tcacaagaca tcaacttcac    720
ccattgtcaa gagcttcaac aggaatgagt cttaagtgat tagctaattc tagaacgcgt    780
cacttggcac tggccgtcgt ttta                                           804
```

<210> SEQ ID NO 9
<211> LENGTH: 11
<212> TYPE: PRT
<213> ORGANISM: Mus musculus

<400> SEQUENCE: 9

Gly Tyr Ala Phe Ser Asn Ser Trp Ile Asn Trp
1               5                   10

<210> SEQ ID NO 10
<211> LENGTH: 11
<212> TYPE: PRT
<213> ORGANISM: Mus musculus

<400> SEQUENCE: 10

Gly Tyr Ser Phe Ile Glu Tyr Thr Ile Asn Trp
1               5                   10

<210> SEQ ID NO 11
<211> LENGTH: 17
<212> TYPE: PRT
<213> ORGANISM: Mus musculus

<400> SEQUENCE: 11

Gly Gln Ile Tyr Pro Gly Asp Tyr Asp Thr Asn Tyr Asn Gly Lys Phe
1               5                   10                  15

Lys

<210> SEQ ID NO 12
<211> LENGTH: 17
<212> TYPE: PRT
<213> ORGANISM: Mus musculus

<400> SEQUENCE: 12

Gly Asn Ile Asp Pro Tyr Tyr Gly Thr Thr Tyr Tyr Asn Gln Met Phe
1               5                   10                  15

Thr

<210> SEQ ID NO 13
<211> LENGTH: 16
<212> TYPE: PRT

-continued

```
<213> ORGANISM: Mus musculus

<400> SEQUENCE: 13

Ala Arg Gly Gly Ser Ile Tyr Tyr Gly Asn Leu Gly Phe Phe Asp Val
1               5                   10                  15

<210> SEQ ID NO 14
<211> LENGTH: 9
<212> TYPE: PRT
<213> ORGANISM: Mus musculus

<400> SEQUENCE: 14

Ala Arg Gly Ser Ala Trp Phe Pro Tyr
1               5

<210> SEQ ID NO 15
<211> LENGTH: 12
<212> TYPE: PRT
<213> ORGANISM: Mus musculus

<400> SEQUENCE: 15

Thr Ala Ser Ser Arg Val Ser Ser Tyr Leu His
1               5                   10

<210> SEQ ID NO 16
<211> LENGTH: 10
<212> TYPE: PRT
<213> ORGANISM: Mus musculus

<400> SEQUENCE: 16

Ser Ala Ser Ser Ser Val Thr Tyr Met Tyr
1               5                   10

<210> SEQ ID NO 17
<211> LENGTH: 7
<212> TYPE: PRT
<213> ORGANISM: Mus musculus

<400> SEQUENCE: 17

Ser Thr Ser Asn Leu Ala Ser
1               5

<210> SEQ ID NO 18
<211> LENGTH: 7
<212> TYPE: PRT
<213> ORGANISM: Mus musculus

<400> SEQUENCE: 18

Asp Thr Ser Asn Leu Ala Ser
1               5

<210> SEQ ID NO 19
<211> LENGTH: 9
<212> TYPE: PRT
<213> ORGANISM: Mus musculus

<400> SEQUENCE: 19

His Gln Tyr His Arg Ser Pro Tyr Thr
1               5

<210> SEQ ID NO 20
<211> LENGTH: 9
<212> TYPE: PRT
<213> ORGANISM: Mus musculus
```

```
<400> SEQUENCE: 20

Gln Gln Trp Ser Asn Tyr Pro Leu Thr
1               5

<210> SEQ ID NO 21
<211> LENGTH: 33
<212> TYPE: DNA
<213> ORGANISM: Mus musculus

<400> SEQUENCE: 21
ggctacgcat tcagtaactc ctggataaac tgg                              33

<210> SEQ ID NO 22
<211> LENGTH: 33
<212> TYPE: DNA
<213> ORGANISM: Mus musculus

<400> SEQUENCE: 22
ggttactcat tcattgagta caccataaac tgg                              33

<210> SEQ ID NO 23
<211> LENGTH: 51
<212> TYPE: DNA
<213> ORGANISM: Mus musculus

<400> SEQUENCE: 23
ggacagattt atcctggaga ttatgatact aactacaatg gaaaattcaa g          51

<210> SEQ ID NO 24
<211> LENGTH: 51
<212> TYPE: DNA
<213> ORGANISM: Mus musculus

<400> SEQUENCE: 24
ggaaatattg atccttatta tggaaccact tattacaatc agatgttcac g          51

<210> SEQ ID NO 25
<211> LENGTH: 48
<212> TYPE: DNA
<213> ORGANISM: Mus musculus

<400> SEQUENCE: 25 gcaaggggggg gatcgatcta ctatggtaac ctcgggttct tcgatgtc             48

<210> SEQ ID NO 26
<211> LENGTH: 27
<212> TYPE: DNA
<213> ORGANISM: Mus musculus

<400> SEQUENCE: 26
gcaagaggct ccgcctggtt tccttac                                     27

<210> SEQ ID NO 27
<211> LENGTH: 36
<212> TYPE: DNA
<213> ORGANISM: Mus musculus

<400> SEQUENCE: 27
actgccagct cacgtgtaag ttccagttac ttgcac                           36

<210> SEQ ID NO 28
<211> LENGTH: 30
<212> TYPE: DNA
```

<210> SEQ ID NO 28
<211> LENGTH: 30
<212> TYPE: DNA
<213> ORGANISM: Mus musculus

<400> SEQUENCE: 28
agtgccagct caagtgtaac ttacatgtac                              30

<210> SEQ ID NO 29
<211> LENGTH: 21
<212> TYPE: DNA
<213> ORGANISM: Mus musculus

<400> SEQUENCE: 29
agtacatcca acctggcttc t                                       21

<210> SEQ ID NO 30
<211> LENGTH: 21
<212> TYPE: DNA
<213> ORGANISM: Mus musculus

<400> SEQUENCE: 30
gacacatcca acctggcttc t                                       21

<210> SEQ ID NO 31
<211> LENGTH: 27
<212> TYPE: DNA
<213> ORGANISM: Mus musculus

<400> SEQUENCE: 31
caccagtatc atcgttcccc gtacacg                                 27

<210> SEQ ID NO 32
<211> LENGTH: 27
<212> TYPE: DNA
<213> ORGANISM: Mus musculus

<400> SEQUENCE: 32
cagcagtgga gtaattaccc actcacg                                 27

<210> SEQ ID NO 33
<211> LENGTH: 33
<212> TYPE: DNA
<213> ORGANISM: Mus musculus

<400> SEQUENCE: 33
ggctacgcat tcagtagcta ctggatgaac tgg                          33

<210> SEQ ID NO 34
<211> LENGTH: 51
<212> TYPE: DNA
<213> ORGANISM: Mus musculus

<400> SEQUENCE: 34
ggacagattt atcctggaga tggtgatact aactacaacg gaaagttcaa g      51

<210> SEQ ID NO 35
<211> LENGTH: 33
<212> TYPE: DNA
<213> ORGANISM: Mus musculus

<400> SEQUENCE: 35
ggttactcat tcactgacta caacatgaac tgg                          33

<210> SEQ ID NO 36
<211> LENGTH: 51

```
<212> TYPE: DNA
<213> ORGANISM: Mus musculus

<400> SEQUENCE: 36
ggagtaatta atcctaacta tggtactact agctacaatc agaagttcaa g       51

<210> SEQ ID NO 37
<211> LENGTH: 36
<212> TYPE: DNA
<213> ORGANISM: Mus musculus

<400> SEQUENCE: 37
actgccagct caagtgtaag ttccagttac ttgcac                        36

<210> SEQ ID NO 38
<211> LENGTH: 21
<212> TYPE: DNA
<213> ORGANISM: Mus musculus

<400> SEQUENCE: 38
agcacatcca acctggcttc t                                        21

<210> SEQ ID NO 39
<211> LENGTH: 25
<212> TYPE: DNA
<213> ORGANISM: Mus musculus

<400> SEQUENCE: 39
caccagtatc atcgttcccc accca                                    25

<210> SEQ ID NO 40
<211> LENGTH: 30
<212> TYPE: DNA
<213> ORGANISM: Mus musculus

<400> SEQUENCE: 40
agtgccagct caagtgtaag ttacatgtac                               30

<210> SEQ ID NO 41
<211> LENGTH: 21
<212> TYPE: DNA
<213> ORGANISM: Mus musculus

<400> SEQUENCE: 41
gacacatcca acctggcttc t                                        21

<210> SEQ ID NO 42
<211> LENGTH: 25
<212> TYPE: DNA
<213> ORGANISM: Mus musculus

<400> SEQUENCE: 42
cagcagtgga gtagttaccc accca                                    25

<210> SEQ ID NO 43
<211> LENGTH: 318
<212> TYPE: PRT
<213> ORGANISM: Homo sapiens

<400> SEQUENCE: 43

Met Ala Ala Gln Gly Cys Ala Ala Ser Arg Leu Leu Gln Leu Leu Leu
 1               5                  10                  15

Gln Leu Leu Leu Leu Leu Leu Leu Leu Ala Ala Gly Gly Ala Arg Ala
```

```
            20                  25                  30
Arg Trp Arg Gly Glu Gly Thr Ser Ala His Leu Arg Asp Ile Phe Leu
         35                  40                  45

Gly Arg Cys Ala Glu Tyr Arg Ala Leu Leu Ser Pro Glu Gln Arg Asn
 50                  55                  60

Lys Asn Cys Thr Ala Ile Trp Glu Ala Phe Lys Val Ala Leu Asp Lys
 65                  70                  75                  80

Asp Pro Cys Ser Val Leu Pro Ser Asp Tyr Asp Leu Phe Ile Asn Leu
                 85                  90                  95

Ser Arg His Ser Ile Pro Arg Asp Lys Ser Leu Phe Trp Glu Asn Ser
                100                 105                 110

His Leu Leu Val Asn Ser Phe Ala Asp Asn Thr Arg Arg Phe Met Pro
            115                 120                 125

Leu Ser Asp Val Leu Tyr Gly Arg Val Ala Asp Phe Leu Ser Trp Cys
        130                 135                 140

Arg Gln Lys Asn Asp Ser Gly Leu Asp Tyr Gln Ser Cys Pro Thr Ser
145                 150                 155                 160

Glu Asp Cys Glu Asn Asn Pro Val Asp Ser Phe Trp Lys Arg Ala Ser
                165                 170                 175

Ile Gln Tyr Ser Lys Asp Ser Ser Gly Val Ile His Val Met Leu Asn
                180                 185                 190

Gly Ser Glu Pro Thr Gly Ala Tyr Pro Ile Lys Gly Phe Phe Ala Asp
            195                 200                 205

Tyr Glu Ile Pro Asn Leu Gln Lys Glu Lys Ile Thr Arg Ile Glu Ile
        210                 215                 220

Trp Val Met His Glu Ile Gly Pro Asn Val Glu Ser Cys Gly Glu
225                 230                 235                 240

Gly Ser Met Lys Val Leu Glu Lys Arg Leu Lys Asp Met Gly Phe Gln
                245                 250                 255

Tyr Ser Cys Ile Asn Asp Tyr Arg Pro Val Lys Leu Leu Gln Cys Val
                260                 265                 270

Asp His Ser Thr His Pro Asp Cys Ala Leu Lys Ser Ala Ala Ala Ala
            275                 280                 285

Thr Gln Arg Lys Ala Pro Ser Leu Tyr Thr Glu Gln Arg Ala Gly Leu
        290                 295                 300

Ile Ile Pro Leu Phe Leu Val Leu Ala Ser Arg Thr Gln Leu
305                 310                 315

<210> SEQ ID NO 44
<211> LENGTH: 264
<212> TYPE: PRT
<213> ORGANISM: Homo sapiens

<400> SEQUENCE: 44

Gly Ala Arg Ala Arg Trp Arg Gly Glu Gly Thr Ser Ala His Leu Arg
 1               5                  10                  15

Asp Ile Phe Leu Gly Arg Cys Ala Glu Tyr Arg Ala Leu Leu Ser Pro
                20                  25                  30

Glu Gln Arg Asn Lys Asn Cys Thr Ala Ile Trp Glu Ala Phe Lys Val
            35                  40                  45

Ala Leu Asp Lys Asp Pro Cys Ser Val Leu Pro Ser Asp Tyr Asp Leu
        50                  55                  60

Phe Ile Asn Leu Ser Arg His Ser Ile Pro Arg Asp Lys Ser Leu Phe
65                  70                  75                  80
```

```
Trp Glu Asn Ser His Leu Leu Val Asn Ser Phe Ala Asp Asn Thr Arg
                85                  90                  95

Arg Phe Met Pro Leu Ser Asp Val Leu Tyr Gly Arg Val Ala Asp Phe
            100                 105                 110

Leu Ser Trp Cys Arg Gln Lys Asn Asp Ser Gly Leu Asp Tyr Gln Ser
        115                 120                 125

Cys Pro Thr Ser Glu Asp Cys Glu Asn Asn Pro Val Asp Ser Phe Trp
    130                 135                 140

Lys Arg Ala Ser Ile Gln Tyr Ser Lys Asp Ser Ser Gly Val Ile His
145                 150                 155                 160

Val Met Leu Asn Gly Ser Glu Pro Thr Gly Ala Tyr Pro Ile Lys Gly
                165                 170                 175

Phe Phe Ala Asp Tyr Glu Ile Pro Asn Leu Gln Lys Glu Lys Ile Thr
            180                 185                 190

Arg Ile Glu Ile Trp Val Met His Glu Ile Gly Gly Pro Asn Val Glu
        195                 200                 205

Ser Cys Gly Glu Gly Ser Met Lys Val Leu Glu Lys Arg Leu Lys Asp
    210                 215                 220

Met Gly Phe Gln Tyr Ser Cys Ile Asn Asp Tyr Arg Pro Val Lys Leu
225                 230                 235                 240

Leu Gln Cys Val Asp His Ser Thr His Pro Asp Cys Ala Leu Lys Ser
                245                 250                 255

Ala Ala Ala Ala Thr Gln Arg Lys
            260

<210> SEQ ID NO 45
<211> LENGTH: 116
<212> TYPE: PRT
<213> ORGANISM: Mus musculus

<400> SEQUENCE: 45

Gln Ala Tyr Leu Gln Gln Ser Gly Pro Glu Leu Val Lys Ala Gly Ala
1               5                   10                  15

Ser Val Lys Met Ser Cys Lys Ala Ser Gly Tyr Ser Phe Ile Glu Tyr
                20                  25                  30

Thr Ile Asn Trp Val Lys Gln Ser His Gly Lys Ser Leu Glu Trp Ile
            35                  40                  45

Gly Asn Ile Asp Pro Tyr Tyr Gly Thr Thr Tyr Asn Gln Met Phe
        50                  55                  60

Thr Gly Lys Ala Thr Leu Thr Val Asp Gln Ser Ser Asn Thr Ala Tyr
65                  70                  75                  80

Met Gln Leu Lys Ser Leu Thr Ser Glu Asp Ser Ala Val Tyr Phe Cys
                85                  90                  95

Ala Arg Gly Ser Ala Trp Phe Pro Tyr Trp Gly Gln Gly Thr Leu Val
            100                 105                 110

Thr Val Ser Ala
        115

<210> SEQ ID NO 46
<211> LENGTH: 116
<212> TYPE: PRT
<213> ORGANISM: Homo sapiens

<400> SEQUENCE: 46

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Ser Phe Ile Glu Tyr
            20                  25                  30

Thr Ile Asn Trp Val Arg Gln Ala Pro Gly Gln Gly Leu Glu Trp Ile
        35                  40                  45

Gly Asn Ile Asp Pro Tyr Tyr Gly Thr Thr Tyr Asn Gln Met Phe
    50                  55                  60

Thr Gly Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ser Ala Trp Phe Pro Tyr Trp Gly Gln Gly Thr Leu Val
                100                 105                 110

Thr Val Ser Ser
        115

<210> SEQ ID NO 47
<211> LENGTH: 117
<212> TYPE: PRT
<213> ORGANISM: Homo sapiens
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(66)
<223> OTHER INFORMATION: Xaa can be any naturally occurring amino acid
<220> FEATURE:
<221> NAME/KEY: misc_feature
<222> LOCATION: (99)..(106)
<223> OTHER INFORMATION: Xaa can be any naturally occurring amino acid

<400> SEQUENCE: 47

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Xaa Xaa
            20                  25                  30

Xaa Xaa Xaa Trp Val Arg Gln Ala Pro Gly Gln Gly Leu Glu Trp Met
        35                  40                  45

Gly Xaa Xaa Xaa Xaa Xaa Xaa Xaa Xaa Xaa Xaa Xaa Xaa Xaa Xaa Xaa
    50                  55                  60

Xaa Xaa Arg Val Thr Leu Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Xaa Xaa Xaa Xaa Xaa Xaa Xaa Trp Gly Gln Gly Thr Leu
                100                 105                 110

Val Pro Val Ser Ser
        115

<210> SEQ ID NO 48
<211> LENGTH: 106
<212> TYPE: PRT
<213> ORGANISM: Mus musculus

<400> SEQUENCE: 48

Asp Ile Val Met Ser Gln Ser Pro Ala Ile Met Ser Ala Ser Pro Gly
1               5                   10                  15

Glu Lys Val Thr Met Thr Cys Ser Ala Ser Ser Ser Val Thr Tyr Met
            20                  25                  30
```

```
Tyr Trp Tyr Gln Gln Lys Pro Gly Ser Ser Pro Arg Leu Leu Ile Tyr
                35                  40                  45

Asp Thr Ser Asn Leu Ala Ser Gly Val Pro Val Arg Phe Ser Gly Ser
         50                  55                  60

Gly Ser Gly Thr Ser Tyr Ser Leu Thr Ile Ser Arg Met Glu Ala Glu
 65                  70                  75                  80

Asp Thr Ala Thr Tyr Tyr Cys Gln Gln Trp Ser Asn Tyr Pro Leu Thr
                 85                  90                  95

Phe Gly Ala Gly Thr Lys Leu Glu Leu Lys
                100                 105

<210> SEQ ID NO 49
<211> LENGTH: 106
<212> TYPE: PRT
<213> ORGANISM: Homo sapiens

<400> SEQUENCE: 49

Asp Ile Gln Met Thr Gln Ser Pro Ser Ser Leu Ser Ala Ser Val Gly
 1               5                  10                  15

Asp Arg Val Thr Ile Thr Cys Ser Ala Ser Ser Ser Val Thr Tyr Met
                 20                  25                  30

Tyr Trp Tyr Gln Gln Lys Pro Gly Lys Ala Pro Lys Leu Leu Ile Tyr
                35                  40                  45

Asp Thr Ser Asn Leu Ala Ser Gly Val Pro Ser Arg Phe Ser Gly Ser
         50                  55                  60

Gly Ser Gly Thr Asp Tyr Thr Leu Thr Ile Ser Ser Leu Gln Pro Glu
 65                  70                  75                  80

Asp Phe Ala Thr Tyr Tyr Cys Gln Gln Trp Ser Asn Tyr Pro Leu Thr
                 85                  90                  95

Phe Gly Gln Gly Thr Lys Val Glu Ile Lys
                100                 105

<210> SEQ ID NO 50
<211> LENGTH: 107
<212> TYPE: PRT
<213> ORGANISM: Homo sapiens
<220> FEATURE:
<221> NAME/KEY: misc_feature
<222> LOCATION: (24)..(34)
<223> OTHER INFORMATION: Xaa can be any naturally occurring amino acid
<220> FEATURE:
<221> NAME/KEY: misc_feature
<222> LOCATION: (50)..(56)
<223> OTHER INFORMATION: Xaa can be any naturally occurring amino acid
<220> FEATURE:
<221> NAME/KEY: misc_feature
<222> LOCATION: (89)..(97)
<223> OTHER INFORMATION: Xaa can be any naturally occurring amino acid

<400> SEQUENCE: 50

Asp Ile Gln Met Thr Gln Ser Pro Ser Ser Leu Ser Ala Ser Val Gly
 1               5                  10                  15

Asp Arg Val Thr Ile Thr Cys Xaa Xaa Xaa Xaa Xaa Xaa Xaa Xaa Xaa
                 20                  25                  30

Xaa Xaa Trp Tyr Gln Gln Lys Pro Gly Lys Ala Pro Lys Leu Leu Ile
                35                  40                  45

Tyr Xaa Xaa Xaa Xaa Xaa Xaa Xaa Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80
```

```
Glu Asp Phe Ala Thr Tyr Tyr Cys Xaa Xaa Xaa Xaa Xaa Xaa Xaa
            85                  90                  95

Xaa Phe Gly Gln Gly Thr Lys Val Glu Ile Lys
            100                 105

<210> SEQ ID NO 51
<211> LENGTH: 16
<212> TYPE: PRT
<213> ORGANISM: Homo sapiens

<400> SEQUENCE: 51

Asn Ile Asp Pro Tyr Tyr Gly Thr Thr Tyr Tyr Asn Gln Met Phe Gln
1               5                   10                  15

<210> SEQ ID NO 52
<211> LENGTH: 245
<212> TYPE: PRT
<213> ORGANISM: Mus musculus

<400> SEQUENCE: 52

Met Lys Gln Ser Thr Ile Ala Leu Ala Leu Leu Pro Leu Leu Phe Thr
1               5                   10                  15

Pro Val Ala Lys Ala Gln Val Gln Leu Gln Gln Ser Arg Ala Glu Leu
            20                  25                  30

Val Met Pro Gly Ala Ser Val Lys Met Ser Cys Lys Thr Ser Gly Tyr
        35                  40                  45

Thr Phe Ser Asp Tyr Trp Val His Trp Val Arg Gln Arg Pro Gly Gln
    50                  55                  60

Gly Leu Glu Trp Ile Gly Ala Ile Asp Gly Ser Asp Thr Phe Asn Asp
65                  70                  75                  80

Tyr Ser Gln Lys Phe Lys Gly Arg Ala Thr Leu Thr Val Asp Glu Ser
                85                  90                  95

Ser Ser Thr Val Tyr Met Gln Leu Ser Ser Leu Thr Ser Glu Asp Ser
            100                 105                 110

Ala Val Tyr Tyr Cys Ala Arg Gly Gly Leu Leu Gln Tyr Trp Gly Gln
        115                 120                 125

Gly Thr Thr Leu Thr Val Ser Ser Ala Lys Thr Thr Pro Pro Ser Val
    130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ser Leu Ser Ser Gly Val His Thr Phe Pro Ala Val
            180                 185                 190

Leu Gln Ser Asp Leu Tyr Thr Leu Ser Ser Ser Val Thr Val Pro Ser
        195                 200                 205

Ser Thr Trp Pro Ser Glu Thr Val Thr Cys Asn Val Ala His Pro Ala
    210                 215                 220

Ser Ser Thr Lys Val Asp Lys Lys Ile Val Pro Arg Asp Cys His His
225                 230                 235                 240

His His His
        245

<210> SEQ ID NO 53
<211> LENGTH: 236
<212> TYPE: PRT
<213> ORGANISM: Mus musculus
```

<400> SEQUENCE: 53

Met Lys Tyr Leu Leu Pro Thr Ala Ala Ala Gly Leu Leu Leu Leu Ala
1               5                   10                  15

Ala Gln Pro Ala Met Ala Asp Ile Gln Leu Thr Gln Ser Pro Ala Ser
            20                  25                  30

Leu Ser Ala Ser Val Gly Glu Thr Val Thr Ile Thr Cys Arg Ala Ser
        35                  40                  45

Glu Asn Ile Tyr Ser Tyr Leu Ala Trp Tyr Gln Gln Lys Gln Gly Lys
    50                  55                  60

Ser Pro Gln Leu Leu Val Tyr Asn Thr Lys Thr Leu Gly Glu Gly Val
65                  70                  75                  80

Pro Ser Arg Phe Ser Gly Ser Gly Ser Gly Thr Gln Phe Ser Leu Lys
                85                  90                  95

Ile Asn Ser Leu Gln Pro Glu Asp Phe Gly Ser Tyr Tyr Cys Gln His
            100                 105                 110

His Tyr Gly Thr Pro Phe Thr Phe Gly Ser Gly Thr Lys Leu Glu Ile
        115                 120                 125

Lys Arg Ala Asp Ala Ala Pro Thr Val Ser Ile Phe Pro Pro Ser Ser
    130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
        195                 200                 205

Glu Arg His Asn Ser Tyr Thr Cys Glu Ala Thr His Lys Thr Ser Thr
    210                 215                 220

Ser Pro Ile Val Lys Ser Phe Asn Arg Asn Glu Ser
225                 230                 235

<210> SEQ ID NO 54
<211> LENGTH: 738
<212> TYPE: DNA
<213> ORGANISM: Mus musculus

<400> SEQUENCE: 54
gtgaaacaaa gcactattgc actggcactc ttaccgctct tatttacccc tgtggcaaaa      60
gcccaggtcc agctgcagca gtctagggct gaacttgtga tgcctggggc ttcagtgaag     120
atgtcctgca agacttctgg ctacacattc tctgactact gggtacactg ggtgaggcag    180
aggcctggac aaggccttga gtggatcgga cgcattgatg ttctgatac ttttaatgac     240
tacagtcaga agtttaaggg cagggccaca ttgactgtag acgaatcctc cagcacagtc    300
tacatgcaac tcagcagcct gacatctgag gactctgcgg tctattactg tgcaaggggg    360
ggccttcttc agtactgggg ccaaggcacc actctcacag tctcctcagc caaaacgaca    420
cccccatctg tctatccact ggcccctgga tctgctgccc aaactaactc catggtgacc    480
ctgggatgcc tggtcaaggg ctatttccct gagccagtga cagtgacctg aactctgga    540
tccctgtcca gcggtgtgca caccttccca gctgtcctgc agtctgacct ctacactctg    600
agcagctcag tgactgtccc ctccagcacc tggcccagcg agaccgtcac ctgcaacgtt    660
gcccacccgg ccagcagcac caaggtggac aagaaaattg tgcccaggga ttgtcatcat    720
caccatcacc atcactaa                                            738

<210> SEQ ID NO 55
<211> LENGTH: 711
<212> TYPE: DNA
<213> ORGANISM: Mus musculus

<400> SEQUENCE: 55
atgaaatacc tattgcctac ggcagccgct ggattgttat tactcgctgc ccaaccagcc    60
atggccgaca ttcagctgac ccagtctcca gcctccctat ctgcatctgt gggagaaact   120
gtcaccatca catgtcgagc aagtgaaaac atttacagtt atttagcatg gtatcagcag   180
aaacagggaa atctcctca gctcctggtc tataatacaa aaaccttagg agaaggtgtg   240
ccatcaaggt tcagtggcag tggatcgggc acacaatttt ctctgaagat caacagcctg   300
cagcctgaag attttgggag ttattactgt caacatcatt atggtactcc attcacgttc   360
ggctcgggga caaagttgga aataaaacgg gctgatgctg caccaactgt atccatcttc   420
ccaccatcca gtgagcagtt aacatctgga ggtgcctcag tcgtgtgctt cttgaacaac   480 ttctaccccca agacatcaa tgtcaagtgg aagattgatg gcagtgaacg acaaaatggc   540
gtcctgaaca gttggactga tcaggacagc aaagacagca cctacagcat gagcagcacc   600
ctcacgttga ccaaggacga gtatgaacga cataacagct atacctgtga ggccactcac   660
aagacatcaa cttcacccat tgtcaagagc ttcaacagga atgagtctta a             711

<210> SEQ ID NO 56
<211> LENGTH: 11
<212> TYPE: PRT
<213> ORGANISM: Mus musculus

<400> SEQUENCE: 56

Gly Tyr Thr Phe Ser Asp Tyr Trp Val His Trp
1               5                   10

<210> SEQ ID NO 57
<211> LENGTH: 17
<212> TYPE: PRT
<213> ORGANISM: Mus musculus

<400> SEQUENCE: 57

Gly Ala Ile Asp Gly Ser Asp Thr Phe Asn Asp Tyr Ser Gln Lys Phe
1               5                   10                  15

Lys

<210> SEQ ID NO 58
<211> LENGTH: 8
<212> TYPE: PRT
<213> ORGANISM: Mus musculus

<400> SEQUENCE: 58

Ala Arg Gly Gly Leu Leu Gln Tyr
1               5

<210> SEQ ID NO 59
<211> LENGTH: 11
<212> TYPE: PRT
<213> ORGANISM: Mus musculus

<400> SEQUENCE: 59

Arg Ala Ser Glu Asn Ile Tyr Ser Tyr Leu Ala
1               5                   10

<210> SEQ ID NO 60
<211> LENGTH: 7
<212> TYPE: PRT
<213> ORGANISM: Mus musculus

<400> SEQUENCE: 60

Asn Thr Lys Thr Leu Gly Glu
1               5

<210> SEQ ID NO 61
<211> LENGTH: 9
<212> TYPE: PRT
<213> ORGANISM: Mus musculus

<400> SEQUENCE: 61

Gln His His Tyr Gly Thr Pro Phe Thr
1               5

<210> SEQ ID NO 62
<211> LENGTH: 33
<212> TYPE: DNA
<213> ORGANISM: Mus musculus

<400> SEQUENCE: 62
ggctacacat tctctgacta ctgggtacac tgg                            33

<210> SEQ ID NO 63
<211> LENGTH: 51
<212> TYPE: DNA
<213> ORGANISM: Mus musculus

<400> SEQUENCE: 63
ggagcgattg atggttctga tacttttaat gactacagtc agaagtttaa g        51

<210> SEQ ID NO 64
<211> LENGTH: 24
<212> TYPE: DNA
<213> ORGANISM: Mus musculus

<400> SEQUENCE: 64 gcaaggggggg gccttcttca gtac                                     24

<210> SEQ ID NO 65
<211> LENGTH: 33
<212> TYPE: DNA
<213> ORGANISM: Mus musculus

<400> SEQUENCE: 65
cgagcaagtg aaaacattta cagttattta gca                            33

<210> SEQ ID NO 66
<211> LENGTH: 21
<212> TYPE: DNA
<213> ORGANISM: Mus musculus

<400> SEQUENCE: 66
aatacaaaaa ccttaggaga a                                         21

<210> SEQ ID NO 67
<211> LENGTH: 27
<212> TYPE: DNA
<213> ORGANISM: Mus musculus

```
<400> SEQUENCE: 67
caacatcatt atggtactcc attcacg                                          27

<210> SEQ ID NO 68
<211> LENGTH: 33
<212> TYPE: DNA
<213> ORGANISM: Mus musculus

<400> SEQUENCE: 68
ggctacacct tcaccagcta ctggatgcac tgg                                   33

<210> SEQ ID NO 69
<211> LENGTH: 51
<212> TYPE: DNA
<213> ORGANISM: Mus musculus

<400> SEQUENCE: 69
ggagagattg atccttctga tagttatact aactacaatc aaaagttcaa g               51

<210> SEQ ID NO 70
<211> LENGTH: 33
<212> TYPE: DNA
<213> ORGANISM: Mus musculus

<400> SEQUENCE: 70
cgagcaagtg agaatattta cagttattta gca                                   33

<210> SEQ ID NO 71
<211> LENGTH: 21
<212> TYPE: DNA
<213> ORGANISM: Mus musculus

<400> SEQUENCE: 71
aatgcaaaaa ccttagcaga a                                                21

<210> SEQ ID NO 72
<211> LENGTH: 23
<212> TYPE: DNA
<213> ORGANISM: Mus musculus

<400> SEQUENCE: 72
caacatcatt atggtactcc tcc                                              23
```